(12) United States Patent
Bhatia et al.

(10) Patent No.: US 12,409,249 B2
(45) Date of Patent: Sep. 9, 2025

(54) COMPOSITIONS AND METHODS FOR IMMUNE TOLERANCE

(71) Applicants: Massachusetts Institute of Technology, Cambridge, MA (US); The General Hospital Corporation, Boston, MA (US)

(72) Inventors: Sangeeta N. Bhatia, Lexington, MA (US); Arnav Chhabra, Cambridge, MA (US); Marcela V. Maus, Lexington, MA (US)

(73) Assignees: Massachusetts Institute of Technology, Cambridge, MA (US); The General Hospital Corporation, Boston, MA (US)

( * ) Notice: Subject to any disclaimer, the term of this patent is extended or adjusted under 35 U.S.C. 154(b) by 814 days.

(21) Appl. No.: 16/696,947

(22) Filed: Nov. 26, 2019

(65) Prior Publication Data

US 2020/0164105 A1    May 28, 2020

Related U.S. Application Data

(60) Provisional application No. 62/873,017, filed on Jul. 11, 2019, provisional application No. 62/771,457, filed on Nov. 26, 2018.

(51) Int. Cl.
| | |
|---|---|
| *A61L 27/36* | (2006.01) |
| *A61K 35/12* | (2015.01) |
| *A61K 35/33* | (2015.01) |
| *A61K 35/407* | (2015.01) |
| *A61K 35/44* | (2015.01) |
| *A61L 27/22* | (2006.01) |
| *A61L 27/38* | (2006.01) |
| *A61L 27/52* | (2006.01) |
| *C12N 5/071* | (2010.01) |
| *C12N 5/077* | (2010.01) |

(52) U.S. Cl.
CPC .......... *A61L 27/3604* (2013.01); *A61K 35/33* (2013.01); *A61K 35/407* (2013.01); *A61K 35/44* (2013.01); *A61L 27/225* (2013.01); *A61L 27/3683* (2013.01); *A61L 27/3804* (2013.01); *A61L 27/3808* (2013.01); *A61L 27/3886* (2013.01); *A61L 27/52* (2013.01); *C12N 5/0656* (2013.01); *C12N 5/067* (2013.01); *C12N 5/069* (2013.01); *A61K 2035/122* (2013.01); *A61L 2430/40* (2013.01); *C12N 2502/1323* (2013.01); *C12N 2502/14* (2013.01); *C12N 2502/28* (2013.01); *C12N 2510/00* (2013.01); *C12N 2533/56* (2013.01)

(58) Field of Classification Search
None
See application file for complete search history.

(56) References Cited

U.S. PATENT DOCUMENTS

2015/0139994 A1    5/2015   Xu

FOREIGN PATENT DOCUMENTS

| JP | 2015-500810 A | 1/2015 |
|---|---|---|
| WO | 00/06204 A2 | 2/2000 |
| WO | 2006/116357 A1 | 11/2006 |
| WO | 2013/082543 A1 | 6/2013 |
| WO | 2018/165547 A1 | 9/2018 |

OTHER PUBLICATIONS

Ben Nasr et al, Sci Transl Med, (2017), 9:eeam7543 (Year: 2017).*
Dudler et al, Transplantation (2006) 82:1733-1737. (Year: 2006).*
Ghannam et al, Stem Cell Research & Therapy (2010), 1:2 (7 pages) (Year: 2010).*
Ghazizadeh et al, Mol Ther (2012):20(1):196-203. (Year: 2012).*
Stevens et al, Sci Transl Med, Jul. 9, 2017: eaah5505 (10 pages) (Year: 2017).*
International Search Report and Written Opinion, PCT/US2019/063450, dated Feb. 26, 2020, 15 pages.
Keir, M. et al., "Tissue expression of PD-L1 mediates peripheral T cell tolerance," The Journal of Experimental Medicine, vol. 203(4): 883-895 (2006).
Tanaka, K. et al., "PDL1 Is Required for Peripheral Transplantation Tolerance and Protec-tion from Chronic Allograft Rejection," The Journal of Immunology, vol. 179(8):5204-5210 (2007).

* cited by examiner

*Primary Examiner* — Allison M Fox
(74) *Attorney, Agent, or Firm* — McCarter & English, LLP; Jill Ann Mello

(57) ABSTRACT

Immunotolerant engineered human tissue constructs are provided that are suitable for implantation into subjects. In some embodiments, the immunotolerance is controllable by an inducible system. Methods of making and using the immunotolerant engineered tissue constructs are provided.

21 Claims, 21 Drawing Sheets
(6 of 21 Drawing Sheet(s) Filed in Color)

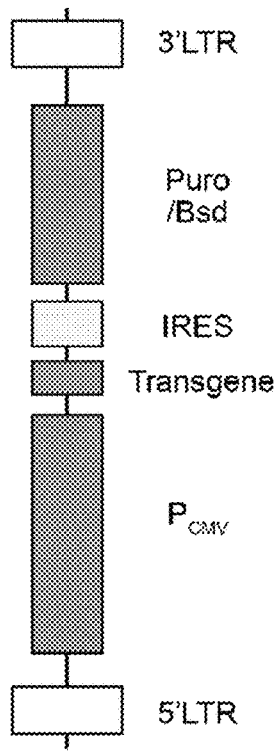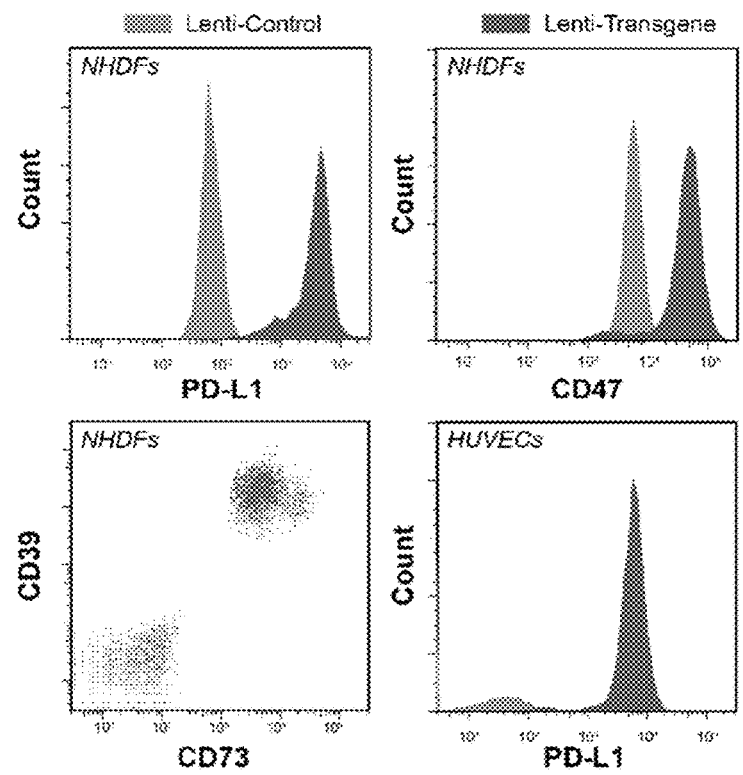
FIG. 1A
FIG. 1B

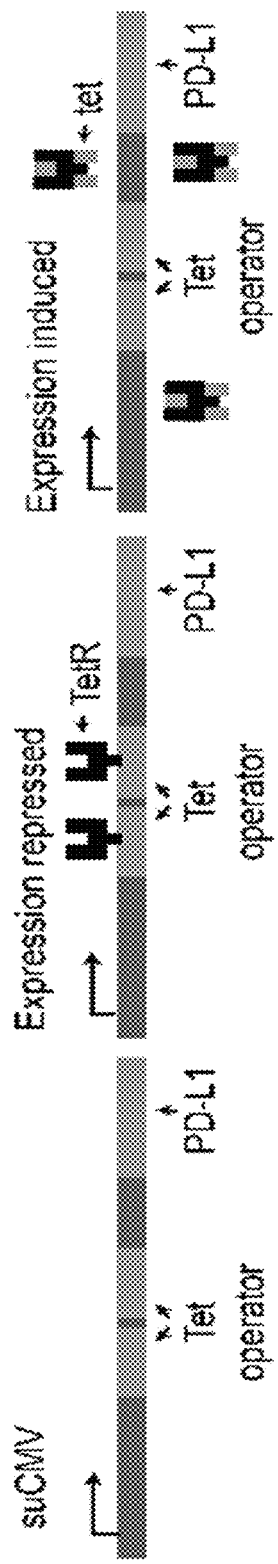
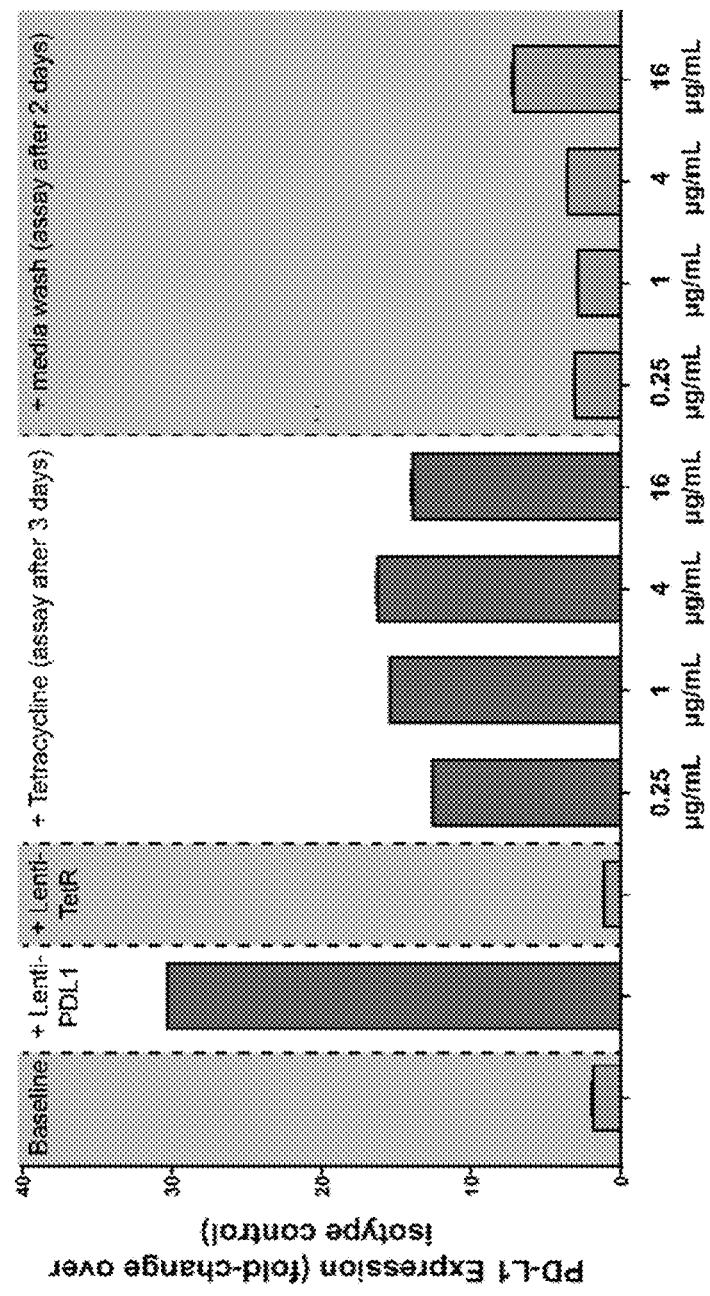
FIG. 6A
FIG. 6B

Lenti-Control

Lenti-PDL1

COMPOSITIONS AND METHODS FOR IMMUNE TOLERANCE

CROSS REFERENCE TO RELATED APPLICATIONS

This application claims the benefit of U.S. Provisional Patent Application Ser. No. 62/771,457, filed on Nov. 26, 2018, and U.S. Provisional Patent Application Ser. No. 62/873,017, filed on Jul. 11, 2019, the entire contents of each of which are herein incorporated by reference in their entireties.

BACKGROUND

Organ transplantation gives thousands of people each year a renewed chance at living full and active lives. For example, in the case of end-stage liver, lung and heart disease, transplantation is generally the only available therapeutic option. Improvements in immunosuppressive drugs and ancillary care have led to outstanding short-term (1-3 year) patient and graft survival rates. This success is mitigated by several problems, including poor long-term (>5 year) graft survival rates, the need for continual immunosuppressive medication and the discrepancy between supply and demand of organs. For example, the demand for organs and tissue far outweighs their supply. For example, in 2017, there were 114,605 candidates on a transplant waitlist (UNOS http://unos.org/), and only 34,770 transplants were performed in 2017. This translates to approximately 20 people who die each day waiting for a transplant. Moreover, Accompanying the problem of late graft loss are the complications of continual immunosuppressive therapy, which include markedly increased risks for cardiovascular disease, opportunistic infections and malignancy.

Allotransplantations have been developed to increase the supply of donor tissue. However, limiting the allogeneic response is a major challenge. Allogeneic transplants do not succeed unless the recipient's immune system, specifically the proliferation and activity of T cells, is downregulated. Furthermore, as with whole organ transplantation, downregulation of the immune response to allotransplantations must be maintained on a lifelong basis. While suppressing the function of T cells is necessary for allogeneic graft acceptance, there is a potential for unintended clinical side effects secondary to recipient immunomodulation. For example, the current clinical standard is the use of systemic immunosuppressive medications, which reduce the efficacy of the graft and substantially increase the risk of infections.

Current modalities which are under development to provide local immunosuppression are mostly centered on modified forms of biomaterials or genetic manipulation of the cells that need to be shielded (cis-mediated). However, parenchymal cells are already limited in number and challenging to manipulate and integrating localized immunosuppression into biomaterials also carries other downsides. For example, Vegas et al. (Nature Medicine 22(3):306, 2016) showed that stem-cell derived β cells encapsulated in chemically modified alginate hydrogels ameliorate the foreign body response. Headen et al. (Nature Materials 17(8):732, 2018), on the other hand, illustrated that microgels coated with an apoptotic form of the Fas ligand resulted in prolonged survival of allogeneic islet grafts in diabetic mice. However, such biomaterials often remodel and/or degrade expeditiously in vivo.

Some groups have attempted a cell-based approach. Gornalusse et al. (Nature Biotechnology 35(8):765, 2017) created universally compatible pluripotent stem cells by eliminating surface expression of all Human Leukocyte Antigen (HLA) class I molecules and adeno-associated virus (AAV)-mediated expression of HLA-E. This strategy, however, depends on pluripotent cell differentiation which is a major limitation for several cell types.

Moreover, a problem that a lot of the current localized immunotolerance strategies suffer from is that their immunomodulation effect deteriorates over time (Vegas et al., supra; Headen et al., supra). Clinically, this can lead to graft rejection since the graft is recognized by the recipient immune system as non-self.

Accordingly, the development of methods to induce transplant tolerance, as a means to improve graft outcomes, eliminate the requirement for continual immunosuppression, and expand the pool of organs for transplantation, remains a major challenge. There is still a need for a universally compatible solution for patients who do not have access to an HLA-matched organ.

SUMMARY OF THE DISCLOSURE

This disclosure is based, as least in part, on the discovery that supporting cells (e.g., fibroblasts and endothelial cells) engineered to express immunomodulatory proteins (e.g., PD-L1) improve the function of transplanted cells, tissues and organs. It has also been demonstrated the expression of an immunomodulatory protein in a genetically engineered support cell is controllable when generated in an inducible format. Without being bound by theory, it is believed when implanted in vivo, mixtures (e.g., suspensions, aggregates, organoids, etc.) containing at least two cell populations, wherein at least one population is genetically engineered to express an immunomodulatory protein, provide inhibitory signals to the host immune system and enable localized immunotolerance, which in some embodiments is controllable.

The disclosure is also based, at least in part, on the discovery that fibroblasts and endothelial cells engineered to express PD-L1 are less susceptible to T cell mediated cytotoxicity. In addition, it was demonstrated that constructs comprising fibroblasts engineered to express PD-L1 and human hepatocytes are protected against immune-mediated elimination, e.g., CAR T cell mediated cytotoxicity. It was also shown that implantable grafts comprising fibroblasts genetically engineered to express PD-L1 were more viable in vivo two weeks after implantation into immunocompetent mice compared to grafts comprising unmodified fibroblasts.

Further, the disclosure is based on the discovery that PD-L1 expression was controllable on fibroblasts by using an inducible expression system. Specifically, administration of tetracycline allowed for expression of PD-L1 on fibroblasts transfected with a promoter comprising a Tet operator region.

Because suppressing the function of T cells is necessary for allogeneic graft acceptance but also provides for the potential for unintended clinical side effects secondary to recipient immunomodulation, it is believed incorporation of an inducible promoter into an implantable cell therapy provides physicians the opportunity to turn off immunomodulation if side effects arise.

The immunomodulation effect provided by current localized immunotolerance strategies deteriorates over time, which can lead to graft rejection due to recognition by the recipient immune system as non-self. Without being bound by theory, it is believed that because the implantable cell therapy provided herein comprises self-replicating populations of cells as opposed to biomaterials or to intravenously infused biologics, this therapy provides a persistent source of inhibitory signals to immune cells throughout the life of the graft. Moreover, patients who receive cell-based therapies with HLA mismatches are prescribed systemic lifelong immunosuppressants, which have a myriad of side-effects such as increased susceptibility to malignancies like cancer and infection, hypertension, neurotoxicity, osteoporosis and many others. Without wishing to be bound by theory, it is believed that by enabling localized immunosuppression that does not affect cells outside of the graft, the compositions and methods provided herein can ameliorate these problems.

It is further believed that the implantable grafts described herein are compatible with a variety of cell-based therapies. As demonstrated herein, genetically modified cells have been shown to promote the function of parenchymal cells. As modifying parenchymal cells for each clinical scenario is inefficient, time-consuming and cost-prohibitive, de-coupling the source of immunotolerance from the parenchymal cells allows for the approach to be integrated with a variety of allogenic transplants to provide a universally compatible solution.

Accordingly, the disclosure provides compositions and implantable grafts containing engineered cell populations which provide an alternative to cell, tissue or whole organ transplantation, or for support during medical intervention of other conditions such as autoimmune disorders and fibrosis.

In one aspect, the present disclosure provides compositions that are suitable for implantation into a subject comprising (a) a first cell population comprising parenchymal cells, endothelial cells, or a combination thereof; and (b) a second cell population comprising genetically engineered immunomodulatory cells which inhibit an immune response to the first cell population.

In some aspects, the present disclosure provides a composition comprising (a) a first cell population comprising parenchymal cells, endothelial cells, or a combination thereof; and (b) a second cell population comprising genetically engineered immunomodulatory cells which inhibit an immune response to the first cell population. In other aspects, the disclosure provides a composition comprising (a) a first cell population comprising parenchymal cells, endothelial cells, or a combination thereof, wherein the cells of the first population are not genetically engineered; and (b) a second cell population comprising genetically engineered immunomodulatory cells which inhibit an immune response to the first cell population.

In one aspect, the present disclosure provides compositions that are suitable for implantation into a subject comprising (a) a first cell population comprising parenchymal cells, endothelial cells, or a combination thereof, wherein the cells of the first population are not genetically engineered; and (b) a second cell population comprising genetically engineered immunomodulatory cells which inhibit an immune response to the first cell population.

In other aspects, the present disclosure provides compositions that are suitable for implantation into a subject comprising (a) a first cell population comprising parenchymal cells, endothelial cells, or a combination thereof; and (b) a second cell population comprising genetically engineered immunomodulatory cells which inhibit an immune response to the first cell population, wherein the first and second cell populations are encapsulated in an extracellular matrix.

In other aspects, the present disclosure provides compositions that are suitable for implantation into a subject comprising (a) a first cell population comprising parenchymal cells, endothelial cells, or a combination thereof, wherein the cells of the first population are not genetically engineered; and (b) a second cell population comprising genetically engineered immunomodulatory cells which inhibit an immune response to the first cell population, wherein the first and second cell populations are encapsulated in an extracellular matrix.

In another aspect, the present disclosure provides implantable grafts comprising (a) a first cell population comprising parenchymal cells, endothelial cells, or a combination thereof; and (b) a second cell population comprising genetically engineered immunomodulatory cells which inhibit an immune response to the first cell population, wherein the first and second cell populations are encapsulated in an extracellular matrix In another aspect, the present disclosure provides implantable grafts comprising (a) a first cell population comprising parenchymal cells, endothelial cells, or a combination thereof, wherein the cells of the first population are not genetically engineered; and (b) a second cell population comprising genetically engineered immunomodulatory cells which inhibit an immune response to the first cell population, wherein the first and second cell populations are encapsulated in an extracellular matrix.

In any of the foregoing or related aspects, the cells of the first cell population are primary hepatocytes, vascular endothelial cells.

In any of the foregoing or related aspects, the cells of the second cell population are genetically engineered to express a protein (e.g., an immune checkpoint protein) which activates one or more checkpoint pathways to induce immune cell exhaustion and anergy to the cells present in the first cell population. In some aspects, the immune checkpoint protein is PD-1, PD-L1, PDL-2, CD47, CD39, CD73, CD200, HVEC, CEACAM1, CD155TIM-3, LAG-3, CTLA-4, A2AR, B7-H3, B7-H4, HLA-E, BTLA, IDO, KIR, VISTA or a combination thereof. In certain aspects, the immune checkpoint protein is PD-L1, CD47, HLA-E, CD39, CD73 or a combination thereof.

In any of the foregoing or related aspects, the genetically engineered second cell population is endothelial cells, fibroblasts, or pericytes. In some aspects, the genetically engineered second cell population is genetically engineered human dermal fibroblasts (HDFs).

In some aspects, the disclosure provides a composition suitable for transplantation into a subject comprising (a) a first cell population comprising primary hepatocytes; and (b) a second cell population comprising genetically engineered human dermal fibroblasts (HDFs) expressing an immune checkpoint protein controlled by an inducible promoter, wherein the immune checkpoint protein is PD-L1, CD47, HLA-E, CD39, CD73 or a combination thereof, wherein the genetically engineered HDFs inhibit an immune response to the first cell population.

In some aspects, the disclosure provides an implantable graph comprising (a) a first cell population comprising primary hepatocytes; and (b) a second cell population comprising genetically engineered human dermal fibroblasts (HDFs) expressing an immune checkpoint protein controlled by an inducible promoter, wherein the immune checkpoint protein is PD-L1, CD47, HLA-E, CD39, CD73 or a combination thereof, wherein the genetically engineered HDFs inhibit an immune response to the first cell population, and wherein (a) and (b) are encapsulated in an extracellular matrix to form an implantable graft.

In some aspects, the disclosure provides a composition suitable for transplantation into a subject comprising (a) a first cell population comprising vascular endothelial cells; and (b) a second cell population comprising genetically engineered human dermal fibroblasts (HDFs) expressing an immune checkpoint protein controlled by an inducible promoter, wherein the immune checkpoint protein is PD-L1, CD47, HLA-E, CD39, CD73 or a combination thereof, wherein the genetically engineered HDFs inhibit an immune response to the first cell population.

In some aspects, the disclosure provides an implantable graph comprising (a) a first cell population comprising vascular endothelial cells; and (b) a second cell population comprising genetically engineered human dermal fibroblasts (HDFs) expressing an immune checkpoint protein controlled by an inducible promoter, wherein the immune checkpoint protein is PD-L1, CD47, HLA-E, CD39, CD73 or a combination thereof, wherein the genetically engineered HDFs inhibit an immune response to the first cell population, and wherein (a) and (b) are encapsulated in an extracellular matrix to form an implantable graft.

In any of the foregoing or related aspects, the cells of the second cell population comprise a vector which expresses the protein. In some aspects, the vector is a viral vector, for example, a lentiviral or adenoviral, or adenoviral-associated vector. In some aspects, expression of the protein is under the control of a constitutively active promoter, an inducible promoter, a tissue specific promoter, a cell-type specific promoter or a temporally restricted promoter. In certain aspects, expression of the protein expressed by the second population of cells is under the control of a chemically inducible promoter, light inducible promoter, temperature inducible promoter or a spatially restricted promoter. In some aspects, the second population of cells further comprises a repressor or activator component.

In some aspects, the disclosure provides a composition suitable for implantation in a subject comprising (i) a first cell population comprising parenchymal cells; and (ii) a second cell population comprising non-parenchymal cells genetically engineered to express an immune checkpoint protein, wherein expression of the immune checkpoint protein is under the control of an inducible promoter.

In some aspects, the disclosure provides a composition suitable for implantation in a subject comprising (i) a first cell population comprising endothelial cells; and (ii) a second cell population comprising non-parenchymal cells genetically engineered to express an immune checkpoint protein, wherein expression of the immune checkpoint protein is under the control of an inducible promoter.

In some aspects, the disclosure provides a composition suitable for implantation in a subject comprising (i) a first cell population comprising hepatocytes; and (ii) a second cell population comprising stromal cells genetically engineered to express an immune checkpoint protein, wherein expression of the immune checkpoint protein is under the control of an inducible promoter.

In some aspects, the disclosure provides a composition suitable for implantation in a subject comprising (i) a first cell population comprising endothelial cells; and (ii) a second cell population comprising stromal cells genetically engineered to express an immune checkpoint protein, wherein expression of the immune checkpoint protein is under the control of an inducible promoter.

In any of the foregoing or related aspects, the compositions and grafts provided herein are in a suspension, in an aggregate, or encapsulated in an extracellular matrix which can be a natural matrix, for example, produced by stromal cells. In other aspects, the matrix is a synthetic matrix, for example, polyethylene glycol (PEG) hydrogel, poly(lactic-co-glycolic acid) (PLGA), hydroxyethyl methacrylate (HEMA), peptide-based self-assembling gels, thermo-responsive poly(NIPAAm), Poly-D, L-lactide (PDLLA), Poly-e-caprolactone (PCL), hydroxyapatite or ceramic-based biomaterials.

In another aspect, the disclosure provides a method of producing the compositions and implantable grafts described herein. In some aspects, the methods comprise mixing the first cell population and the second cell population in cell culture medium under conditions sufficient to maintain viability of the cells. In some aspects, the methods further comprise co-culturing the cell mixture until extracellular matrix synthesized by the stromal cells encapsulates the cell mixture to form cell aggregates and suspending the aggregates in a solution comprising fibrinogen and thrombin under conditions which promote formation of fibrin for a time sufficient to form the implantable graft.

In some aspects, the disclosure provides a method of producing an implantable graft, the method comprising:
(i) mixing (a) a first cell population of cells comprising parenchymal cells, endothelial cells or a combination thereof and (b) a second cell population comprising genetically engineered immunomodulatory cells which inhibit an immune response to the first cell population, in cell culture medium under conditions to maintain viability of the cells;
(ii) co-culturing the cell mixture until extracellular matrix synthesized by the stromal cells encapsulates the cell mixture to form cell aggregates; and
(iii) suspending the aggregates in a solution comprising fibrinogen and thrombin under conditions which promote formation of fibrin for a time sufficient to form the implantable graft.

In another aspect, the disclosure provides methods of inhibiting immune rejection of a graft by administering the compositions or implantable grafts provided herein.

In another aspect, the invention provides methods of reducing immune activation, for example, in response to transplantation of cells, tissues or organs into a subject, by administering the compositions or implantable grafts provided herein.

In another aspect, the invention provides a method of promoting immune tolerance in a subject by administering by administering the compositions or implantable grafts provided herein.

In another aspect, the invention provides methods of promoting immune tolerance, for example, in response to transplantation of cells, tissues or organs into a subject, by administering the compositions or implantable grafts provided herein.

In some aspects, the invention provides compositions and implantable grafts for use in inhibition of immune rejection by administering the compositions or implantable grafts provided herein.

In some aspects, the invention provides compositions and implantable grafts for use in inhibition of immune activation by administering the compositions or implantable grafts provided herein.

In some aspects, the invention provides compositions and implantable grafts for use in promoting immune tolerance by administering the compositions or implantable grafts provided herein.

In some aspects, the methods provided herein reduce, inhibit or ameliorate an immune response, or promote immune tolerance in the subject to allogeneic cells, tissues or organs. In some aspects, the methods provided herein reduce, inhibit or ameliorate an immune response, or promote immune tolerance in the subject to xenogeneic cells, tissues or organs. In other aspects, the methods provide herein inhibit, reduce or ameliorate an immune response, or promote immune tolerance to homogeneic molecules, for example, in an autoimmune disorder.

In some aspects, the compositions and implantable grafts provided herein reduce, inhibit or ameliorate an immune response, or promote immune tolerance in the subject to allogeneic cells, tissues or organs. In some aspects, the compositions and implantable grafts provided herein reduce, inhibit or ameliorate an immune response, or promote immune tolerance in the subject to xenogeneic cells, tissues or organs. In other aspects, the compositions and implantable grafts provide herein inhibit, reduce or ameliorate an immune response, or promote immune tolerance to homogeneic molecules, for example, in an autoimmune disorder.

These and other aspects and embodiments will be described in greater detail herein.

Each of the limitations of the invention can encompass various embodiments of the invention. It is therefore anticipated that each of the limitations of the invention involving any one element or combinations of elements can be included in each aspect of the invention. This invention is not limited in its application to the details of construction and/or the arrangement of components set forth in the following description or illustrated in the drawings.

BRIEF DESCRIPTION OF THE DRAWINGS

The accompanying drawings are not intended to be drawn to scale. For purposes of clarity, not every component may be labeled in every drawing. The patent or application file contains at least one drawing executed in color. Copies of this patent or patent application publication with color drawing(s) will be provided by the Office upon request and payment of the necessary fee.

FIG. 1A is a schematic description of lentiviral construct harboring the various transgenes. FIG. 1B depicts flow-cytometry analysis of HDFs or HUVECs (labeled) with tagged antibodies targeting the various molecules.

FIG. 3A is a schematic description of CAR-T challenge, whereby the CAR targets EGFR on HDFs. FIG. 3B depicts a flow-cytometry analysis of HDFs and primary human hepatocytes (PHHs) (labeled) with tagged antibodies targeting EGFR. FIG. 3C is a bar graph depicting viability of modified or control HDFs challenged with EGFR CAR-Ts, at various doses and at various timepoints (n=4; mean±SEM). FIG. 3D depicts pro-inflammatory cytokine concentrations in the supernatants of the HDF cultures after challenge with EGFR CAR-Ts or untransduced T cells (controls) (n=4). Pro-inflammatory cytokine concentrations in the HDF and PD-L1 Tg culture supernatants are depicted in FIG. 3E (GM-CSF), FIG. 3F (IFN-γ), FIG. 3G (IL-2), and FIG. 3H (TNF-α) (n=4; mean±SEM).

FIG. 4A is a schematic description of T cell challenge, whereby HUVECs provide co-stimulation and an exogenously supplied anti-CD3 IgG (clone OKT3) activates TCR signaling. FIG. 4B depicts immunofluorescence analysis of fabricated vessels lined with WT and PD-L1 Tg HUVECs. Vessels are challenged with human T cells in the presence of an activating α-CD3 IgG at 30 ng/mL (representative images; maximum intensity projection; scale bar=50 μm). FIG. 4C is a graph depicting barrier permeability of the fabricated vessels lined with WT or PD-L1 Tg HUVECs, and challenged with T cells.

FIG. 5A depicts the experimental timeline. FIG. 5B is a schematic of the two-step layered fabrication approach which allows HDFs to form a protective barrier around a core of human hepatocytes. FIG. 5C depicts immunofluorescence analysis of the implantable constructs generated via two-step fabrication. Cytokeratin 18 (CK18) is a hepatocyte marker (representative images; maximum intensity projection; scale bar=100 μm). FIG. 5D is a graph depicting albumin concentrations in the supernatants of various conditions with and without EGFR CAR-Ts (n=3; mean±SEM).

FIGS. 6A-6B show that PD-L1 expression can be inducibly expressed on HDFs. FIG. 6A is a schematic depicting inducible expression of PD-L1. (Left) PD-L1 and an upstream Tet operator region are expressed under a super CMV (suCMV) promoter. (Middle) Upon co-expression of TetR which binds to the Tet operator region, expression of PD-L1 is repressed. (Right) Exogenous administration of tetracycline (tet) blocks binding of TetR with Tet operator, thus allowing for expression of PD-L1. FIG. 6B depicts flow-cytometry analysis of PD-L1 expression on the surface of HDFs. (From left to right) (i) Baseline HDFs, (ii) HDFs with expression of PD-L1 and upstream Tet operator under suCMV, (iii) co-expression of TetR, (iv) addition of various concentrations of tet to the HDF cultures (flow analysis performed after 3 days of tet induction), and (v) wash out of tet (flow analysis performed after 2 days of media wash).

In FIG. 7A engineered stromal support cells are aggregated with parenchymal cells using pyramid-shaped microwells to create organoids. In FIG. 7B the organoids are embedded in an implantable biomaterial. In FIG. 7C the graft is implanted into the intraperitoneal space of the animal. In FIG. 7D the stromal support cells provide inhibitory signals to suppress the activity of T cells surveying the graft.

FIG. 8A is an image showing PHHs aggregated with HDFs in microwells compacted over a period of two days to form organoids. FIG. 8B is a graph showing PHHs aggregated with HDFs depict better albumin synthesis than PHHs aggregated without HDFs.

FIG. 9A is a schematic description of lentiviral particles with a PD-L1 and RFP vector used to transduce HDFs with transgenic PD-L1. FIG. 9B is a graph showing infection with lentiviral particles lead to a pure population of PD-L1$^{hi}$ HDFs, after the transduced cells are sorted and expanded.

FIG. 12A is a schematic depicting hepatic organoids embedded in an implantable cylindrical fibrin gel. FIG. 12B is an image of hepatic organoids that survived in the graft.

DETAILED DESCRIPTION

Figure 2A:
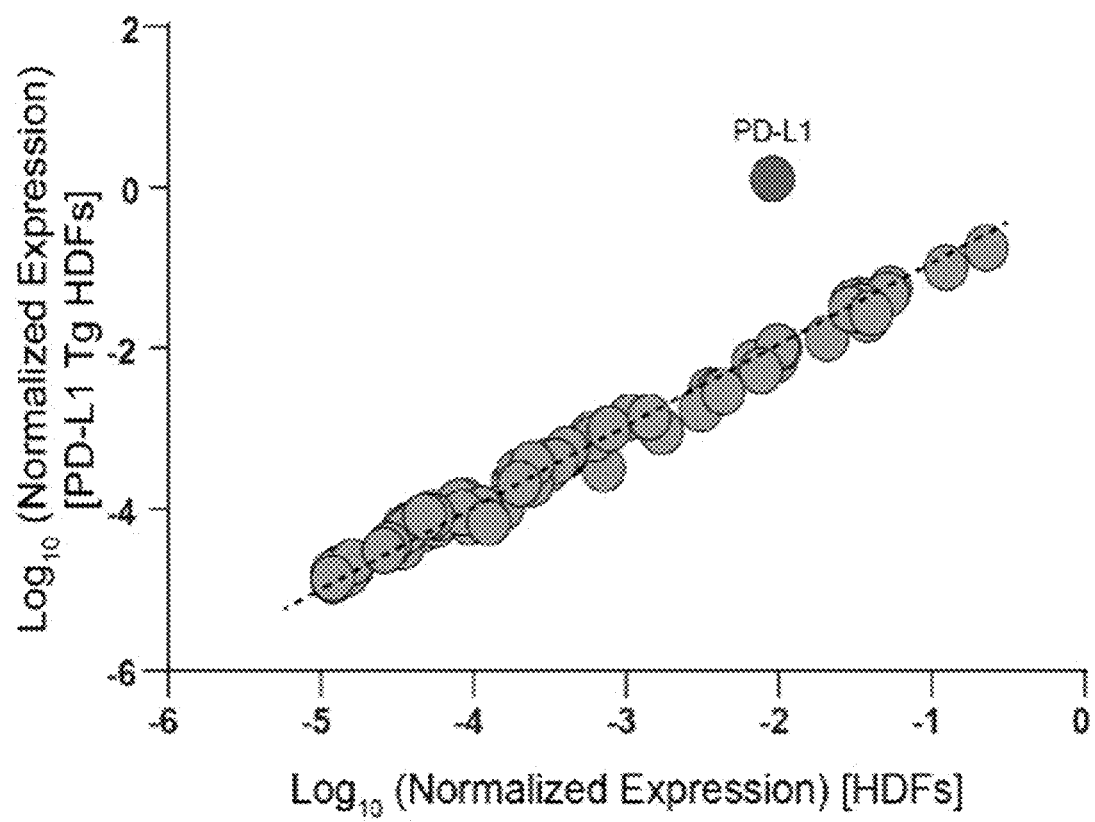
FIG. 2A is a graph depicting the transcriptional comparison of PD-L1 between transduced and control HDF populations (n=3 independent lines; 84 genes relevant to T and B cell activation).

The disclosure relates to methods and compositions for implantation which contain a population of genetically engineered cells which elicit immunotolerance in the host. Such engineered cell mixtures or aggregates are particularly suited for implantation in a host, for example a human or non-human, animal host.

As described herein, the compositions and methods provide herein have the advantage of allowing for controllable expression of proteins that induce localized immunotolerance and, thus, provide physicians the opportunity to turn off immunomodulation of transplanted cells and tissues if side effects arise. In addition, by decoupling the source of immunotolerance from the transplanted parenchymal or endothelial cells, the disclosure provides "off-the-shelf" allogeneic and/or xenogeneic cell therapies. For example, the genetically engineered second population of cells in the composition disclosed herein (e.g., support cells) can be integrated with a variety of allogeneic transplants to provide a universally compatible cell therapy.

In addition, the engineered cell mixtures as described herein are useful to produce an animal (e.g., a mouse) having an engineered human tissue. In such fashion, these animals are made having a host of uses, in particular, in pharmaceutical development and as animal models of disease. Accordingly, the compositions and methods described herein are suitable for routine laboratory research, as well as large scale industrial and clinical applications.

I. Definitions

All technical and scientific terms used herein, unless otherwise defined below, are intended to have the same meaning as commonly understood by one of ordinary skill in the art. Mention of techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

As used herein, "about" will be understood by persons of ordinary skill and will vary to some extent depending on the context in which it is used. If there are uses of the term which are not clear to persons of ordinary skill given the context in which it is used, "about" will mean up to plus or minus 10% of the particular value.

As used herein and in the appended claims, the singular forms "a," "and," and "the" include plural referents unless the context clearly dictates otherwise. Thus, for example, reference to "a cellular aggregate" includes a plurality of such cellular aggregates and reference to "the cell" includes reference to one or more cells known to those skilled in the art, and so forth.

As used herein, the term "and/or" when used in the context of a list of entities, refers to the entities being present singly or in any possible combination or subcombination.

The term "comprising" or "comprises" is used in reference to compositions, methods, and respective component(s) thereof, that are essential to the present disclosure, yet open to the inclusion of unspecified elements, whether essential or not.

The term "consisting essentially of" refers to those elements required for a given aspect. The term permits the presence of additional elements that do not materially affect the basic and novel or functional characteristic(s) of that aspect of the present disclosure.

The term "consisting of" refers to compositions, methods, and respective components thereof as described herein, which are exclusive of any element not recited in that description of the aspect.

An "immune response" refers to a biological response within a vertebrate against foreign agents, which response protects the organism against these agents and diseases caused by them. An immune response is mediated by the action of a cell of the immune system (for example, a T lymphocyte, B lymphocyte, natural killer (NK) cell, macrophage, eosinophil, mast cell, dendritic cell or neutrophil) and soluble macromolecules produced by any of these cells or the liver (including antibodies, cytokines, and complement) that results in selective targeting, binding to, damage to, destruction of, and/or elimination from the vertebrate's body of invading pathogens, cells or tissues infected with pathogens, cancerous or other abnormal cells, or, in cases of autoimmunity or pathological inflammation, normal human cells or tissues. An immune response or reaction includes, e.g., activation or inhibition of a T cell, e.g., an effector T cell or a Th cell, such as a CD4+ or CD8+ T cell, or the inhibition of a Treg cell.

As used herein, "immune cell" is a cell of hematopoietic origin and that plays a role in the immune response. Immune cells include lymphocytes (e.g., B cells and T cells), natural killer cells, and myeloid cells (e.g., monocytes, macrophages, eosinophils, mast cells, basophils, and granulocytes).

As used herein, the term "T cell-mediated response" refers to a response mediated by T cells, including effector T cells (e.g., CD8+ cells) and helper T cells (e.g., CD4+ cells). T cell mediated responses include, for example, T cell cytotoxicity and proliferation. As used herein, the term "cytotoxic T lymphocyte (CTL) response" refers to an immune response induced by cytotoxic T cells. CTL responses are mediated primarily by CD8+ T cells.

The term "Major Histocompatibility Complex" or "MHC" refers to genomic locus containing a group of genes that encode the polymorphic cell-membrane-bound glycoproteins known as MHC classical class I and class II molecules that regulate the immune response by presenting peptides of fragmented proteins to circulating cytotoxic and helper T lymphocytes, respectively. In humans this group of genes is also called the "human leukocyte antigen" or "HLA" system. Human MHC class I genes encode, for example, HLA-A, HL-B and HLA-C molecules. HLA-A is one of three major types of human MHC class I cell surface receptors. The others are HLA-B and HLA-C. The HLA-A protein is a heterodimer and is composed of a heavy a chain and smaller β chain. The α chain is encoded by a variant HLA-A gene, and the β chain (β2-microglobulin) is an invariant β2 microglobulin molecule. The β2 microglobulin protein is coded for by a separate region of the human genome. HLA-A*02 (A*02) is a human leukocyte antigen serotype within the HLA-A serotype group. The serotype is determined by the antibody recognition of the α2 domain of the HLA-A α-chain. For A*02, the α chain is encoded by the HLA-A*02 gene and the β chain is encoded by the B2M locus. Human MHC class II genes encode, for example, HLA-DPA1, HLA-DPB1, HLA-DQA1, HLA-DQB1, HLA-DRA and HLA-DRB1. The complete nucleotide sequence and gene map of the human major histocompatibility complex is publicly available (e.g., The MHC sequencing consortium, Nature 401:921-923, 1999).

An "immunomodulatory protein" or "immunomodulatory polypeptide" is a protein that modulates immunological activity. By "modulation" or "modulating" an immune response is meant that immunological activity is either enhanced or suppressed. An immunomodulatory protein can be a single peptide, polypeptide chain or a multimer (dimers or higher order multimers). Secretable immunomodulatory proteins are a type of immunomodulatory protein.

An "immunomodulatory cell" is a cell expressing an immunomodulatory protein as described herein. In some embodiments, a cell is genetically engineered to express or overexpress an immunomodulatory protein. In some embodiments, a cell is genetically engineered to express or overexpress an immunomodulatory protein such that an immune response to the engineered cell or nearby cells is reduced or inhibited. In some embodiments, a cell is genetically engineered to express or overexpress an immunomodulatory protein such that an immune response to the engineered cell or nearby cells is not triggered. In some embodiments, an immunomodulatory cell expresses an immune checkpoint protein.

As used herein, the term "immune checkpoints," "immune checkpoint proteins," "immune checkpoint molecules," or "immune checkpoint regulators" refers to a group of molecules associated with signaling pathways in cells of the immune system which down-modulate or inhibit an immune response. Immune checkpoint regulators are known in the art and include, without limitation, CTLA-4, PD-1, PDL-1, PDL-2, LAG-3, TIM-3, B7-H2, B7-H3, B7-H4, B7-H6, 2B4, ICOS, HVEM, PD-L2, CD160, gp49B, PIR-B, KIR family receptors, TIM-1, TIM-3, TIM-4, LAG-3, BTLA, SIRPalpha (CD47), CD48, 2B4 (CD244), B7.1, B7.2, ILT-2, ILT-4, TIGIT, BTLA, and A2aR.

As used herein the term "transplant" refers to the replacement of an organ, for example, a kidney, in a human or non-human animal recipient. The purpose of replacement is to remove a diseased organ or tissue in the host and replace it with a healthy organ or tissue from the donor. Where the donor and the recipient are the same species the transplant is known as an "allograft". Where the donor and the recipient are dissimilar species the transplant is known as a "xenograft". The techniques necessary for transplantation are varied and depend to a large extent on the nature of the organ being transplanted. The success of the transplant as a therapeutic modality depends on a number of possible physiological outcomes. For example, the host may reject the new organ via antibody-dependent hyperacute rejection mechanisms, cell-mediated acute rejection or chronic degenerative processes.

The terms "allograft", "homograft" and "allogeneic graft" refer to the transplant of an organ or tissue from one individual to another of the same species with a different genotype, including transplants from cadaveric, living related, and living unrelated donors. A graft transplanted from one individual to the same individual is referred to as an "autologous graft" or "autograft". A graft transplanted between two genetically identical or syngeneic individuals is referred to as a "syngeneic graft". A graft transplanted between individuals of different species is referred to as a "xenogeneic graft" or "xenograft".

As used herein, the term "rejection" refers to the process or processes by which the immune response of an organ transplant recipient mounts a reaction against the transplanted organ, cell or tissue, sufficient to impair or destroy normal function of the organ. The immune system response can involve specific (antibody and T cell-dependent) or non-specific (phagocytic, complement-dependent, etc.) mechanisms, or both.

Hyperacute transplant rejection occurs immediately by the action of pre-formed antibodies against the donor tissue. It is generally caused by ABO blood type incompatibility and presents while still in surgery with thrombosis and occlusion of grafted tissues.

Acute transplant rejection is the most common type of Host v. Graft rejection and occurs within weeks to months following transplantation. It is characterized by a T-cell mediated response against the foreign MHC of the transplanted tissues causing inflammation and leukocyte infiltration of grafted tissues.

Chronic transplant rejection may occur months to years following the transplant. It is a T-cell mediated process resulting from the foreign MHC of the transplanted tissues "looking like" a self MHC carrying an antigen, and results in intimal thickening and fibrosis of grafted vessels or tissues, as well as graft atrophy.

Graft v. Host Transplant Rejection occurs when donor T-cells within the graft tissue proliferate and attack the recipient's tissue, and most commonly occurs in bone marrow transplants resulting in diarrhea, rash and jaundice.

As used herein, "proliferating" and "proliferation" refers to an increase in the number of cells in a population (growth) by means of cell division. Cell proliferation is generally understood to result from the coordinated activation of multiple signal transduction pathways in response to the environment, including growth factors and other mitogens. Cell proliferation may also be promoted by release from the actions of intra- or extracellular signals and mechanisms that block or negatively affect cell proliferation.

As used herein, the term "tissue regeneration" or "organ regeneration" refers to the expansion, growth, and increase in volume of the tissue or organ. Regeneration can occur with replacement of tissue loss with phenotypic fidelity of cell types (i.e., each cell type of the tissue or organ enters into proliferation to replace its own cellular compartment). In certain embodiments, tissue or organ regeneration is deemed to have occurred by an increase in cell number, an increase in cell size, an increase in tissue or organ volume, and/or an increase in size of the tissue and/or by an increase in production of a tissue derived factor(s). See e.g., Michalopoulos (*Comprehensive Physiology* (2013), Vol. 3: 485-513), herein incorporated by reference.

The term "expand" as used herein, refers to an increase in size, volume or area of a tissue graft. In certain embodiments, the implanted genetically engineered cell mixture expands, as determined by volume, weight, and area.

The term "isolated population" with respect to a population of cells as used herein refers to a population of cells that has been removed and separated from a mixed or heterogeneous population of cells. In some embodiments, an isolated population is a substantially pure population of cells as compared to the heterogeneous population from which the cells were isolated or enriched from.

The term "clonal population", as used herein, refers to a population of cells that is derived from the outgrowth of a single cell. That is, the cells within the clonal population are all progeny of a single cell that was used to seed the clonal population.

As used herein, the term "co-culture" refers to a collection of cells cultured in a manner such that more than one population of cells are in association with each other. Co-cultures can be made such that cells exhibit heterotypic interactions (i.e., interaction between cells of populations of different cell types), homotypic interactions (i.e., interaction between cells of the same cell types) or co-cultured to exhibit a specific and/or controlled combination of heterotypic and homotypic interactions between cells.

As used herein, the term "parenchymal cells" refers to cells of, or derived from, the parenchyma of an organ or gland, e.g., a mammalian organ or gland. The parenchyma of an organ or gland is the functional tissue of the organ or gland, as distinguished from surrounding or supporting or connective tissue. As such, parenchymal cells are attributed with carrying out the particular function, or functions, of the organ or gland, often referred to in the art as "tissue-specific" function. Parenchymal cells include, but are not limited to, hepatocytes, pancreatic cells (alpha, beta, gamma, delta), myocytes, e.g., smooth muscle cells, cardiac myocytes, and the like, enterocytes, renal epithelial cells and other kidney cells, brain cell (neurons, astrocytes, glia cells), respiratory epithelial cells, stem cells, and blood cells (e.g., erythrocytes and lymphocytes), adult and embryonic stem cells, blood-brain barrier cells, adipocytes, splenocytes, osteoblasts, osteoclasts, and other parenchymal cell types known in the art.

Certain precursor cells can also be included as "parenchymal cells", in particular, if they are committed to becoming the more differentiated cells described above, including but not limited to liver progenitor cells, oval cells, adipocytes, osteoblasts, osteoclasts, myoblasts, stem cells (e.g., embryonic stem cells, hematopoietic stem cells, mesenchymal stem cells, endothelial stem cells, and the like). In some embodiments stem cells can be encapsulated and/or implanted under specified conditions such that they are induced to differentiate into a desired parenchymal cell type. It is also contemplated that parenchymal cells derived from cell lines can be used in the methodologies of the disclosure.

The term "non-parenchymal cells" as used herein, refers to the cells of or derived from the tissue surrounding or supporting parenchymal tissue in an organ or gland, for example, in a mammalian (e.g., human) organ or gland, or the connective tissue of such an organ or gland. Exemplary non-parenchymal cells include, but are not limited to, stromal cells (e.g., fibroblasts), endothelial cells, stellate cells, cholangiocytes (bile duct cells), Kupffer cells, pit cells, and the like. The choice of non-parenchymal cells used in the constructs described herein will depend upon the parenchymal cell types used.

The term "stromal cells" as used herein, refers to connective tissue cells of any organ which form the functionally supportive framework of a biological cell, tissue or organ. The most common stromal cells include endothelial cells, fibroblasts and pericytes. Stromal cells can be multipotent. Multipotent stromal cells, which include mesenchymal stem cells, can differentiate into a variety of cell types including, but not limited to, osteoblasts, chondrocytes, myocytes and adipocytes. For example, the term encompasses multipotent cells derived from other non-marrow tissues, such as placenta, umbilical cord blood, adipose tissue, adult muscle, corneal stroma or the dental pulp of deciduous baby teeth The term "endothelial cell" as used herein, refers to cells which form the lining of all parts of the circulatory system, such as the heart, arteries, veins, capillaries and lymph vessels. Endothelial cells form the endothelium, a single layer of squamous cells.

As used herein, "modulation of gene expression" refers to changes in the induction or repression of a gene. Mechanisms that are involved with the gene regulation include structural and chemical changes to the genetic material, binding of proteins to specific DNA elements to regulate transcription, or mechanisms that modulate translation of mRNA.

Polypeptide," "peptide", and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. The terms "isolated protein" and "isolated polypeptide" are used interchangeably to refer to a protein (e.g., a soluble, multimeric protein) which has been separated or purified from other components (e.g., proteins, cellular material) and/or chemicals. Typically, a polypeptide is purified when it constitutes at least 60 (e.g., at least 65, 70, 75, 80, 85, 90, 92, 95, 97, or 99) % by weight of the total protein in the sample.

As used herein, the phrases "expression vector" and "recombinant expression vector" refer to genetically-modified oligonucleotide and/or polynucleotide constructs that permit the expression of an mRNA, protein, polypeptide, and/or peptide by a host cell, when the construct comprises a nucleotide sequence encoding the mRNA, protein, polypeptide, and/or peptide, and the vector is contacted with the cell under conditions sufficient to have the mRNA, protein, polypeptide, and/or peptide expressed within the cell. Expression vectors can comprise any type of nucleotides, including, but not limited to DNA and RNA, which can be single-stranded or double-stranded, synthesized or obtained in part from natural sources, and which can contain natural, non-natural, and/or altered nucleotides.

As used herein, a "promoter sequence" is a DNA regulatory region capable of binding RNA polymerase and initiating transcription of a downstream (3' direction) coding or non-coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate transcription of a non-coding sequence (e.g., guide RNA) or a coding sequence (e.g., site-directed modifying polypeptide, or Cas9 polypeptide) and/or regulate translation of an encoded polypeptide.

An "expression cassette" comprises a DNA coding sequence operably linked to a promoter. "Operably linked"

refers to a juxtaposition wherein the components so described are in a relationship permitting them to function in their intended manner. For instance, a promoter is operably linked to a coding sequence if the promoter affects its transcription or expression. The terms "recombinant expression vector," or "DNA construct" are used interchangeably herein to refer to a DNA molecule comprising a vector and at least one insert. Recombinant expression vectors are usually generated for the purpose of expressing and/or propagating the insert(s), or for the construction of other recombinant nucleotide sequences. The nucleic acid(s) can or cannot be operably linked to a promoter sequence and can or cannot be operably linked to DNA regulatory sequences.

A cell has been "genetically modified" or "genetically engineered" or "transformed" or "transfected" by exogenous DNA, e.g. a recombinant expression vector, when such DNA has been introduced inside the cell. The presence of the exogenous DNA results in permanent or transient genetic change.

As used herein, the "extracellular matrix" refers to a complex non-cellular three-dimensional macromolecular network composed of collagens, proteoglycans/glycosaminoglycans, elastin, fibronectin, laminins, and several other glycoproteins. These molecules are secreted locally by cells and remain closely associated with them to provide structural, adhesive and biochemical signaling support.

As used herein, the term "encapsulation" refers to the confinement of a cell or population of cells within a material, for example, within a biocompatible hydrogel. The term "co-encapsulation" refers to encapsulation of more than one cell or cell type or population or populations of cells within the material, e.g., the hydrogel.

As used herein, the term "hydrogel" refers to a network of polymer chains that are hydrophilic in nature, such that the material absorbs a high volume of water or other aqueous solution. Hydrogels can include, for example, at least 70% v/v water, at least 80% v/v water, at least 90% v/v water, at least 95%, 96%, 97%, 98% and even 99% or greater v/v water (or other aqueous solution). Hydrogels can comprise natural or synthetic polymers, the polymeric network often featuring a high degree of crosslinking. Hydrogels also possess a degree of flexibility very similar to natural tissue, due to their significant water content. Hydrogels are particularly useful in tissue engineering applications as scaffolds for culturing cells. In certain embodiments, the hydrogels are made of biocompatible polymers.

As used herein, the term "preventing" when used in relation to a condition, refers to administration of a composition which reduces the frequency of, or delays the onset of, symptoms of a medical condition in a subject relative to a subject which does not receive the composition.

The term "ameliorating" refers to any therapeutically beneficial result in the treatment of a disease state, e.g., immune disorder, including prophylaxis, lessening in the severity or progression, remission, or cure thereof.

As used herein, the term "subject" or "patient" includes any human or non-human animal that receive treatment. The term "non-human animal" includes all vertebrates, e.g., mammals and non-mammals, such as non-human primates, sheep, dog, cow, chickens, amphibians, reptiles, etc.

As used herein, a subject "in need of prevention," "in need of treatment," or "in need thereof," refers to one, who by the judgment of an appropriate medical practitioner (e.g., a doctor, a nurse, or a nurse practitioner in the case of humans; a veterinarian in the case of non-human mammals), would reasonably benefit from a given treatment (such as treatment with a composition comprising a fusion protein described herein).

As used herein the term "reducing" refers to a decrease by a statistically significant amount. For example, in one embodiment, reducing refers to either partially or completely inhibiting an activity or decreasing or lowering an activity. In one embodiment, "reducing" means a decrease by at least 10% compared to a reference level, for example a decrease by at least about 15%, or at least about 20%, or at least about 25%, or at least about 30%, or at least about 35%, or at least about 40%, or at least about 45%, or at least about 50%, or at least about 55%, or at least about 60%, or at least about 65%, or at least about 70%, or at least about 75%, or at least about 80%, or at least about 85%, or at least about 90%, or at least about 95%, or up to and including a 100% decrease compared to a reference sample, or any decrease between about 10-100% compared to a reference level.

As used herein, the term "orthotopic" means occurring at the expected place in the body. As a non-limiting example, a hepatic graft can be implanted at the liver.

As used herein, the term "ectopic" means occurring in an abnormal position or place. Accordingly, "implantation at an ectopic site" means implantation at an abnormal site or at a site displaced from the normal site. Ectopic sites of implantation can also be within an organ, i.e., an organ different than that of the source cells of the construct being implanted (e.g., implanting a human liver construct into the spleen of an animal). Ectopic sites of implantation can also include other body cavities capable of housing a construct described herein. In some embodiments, ectopic sites include, for example, lymph nodes. The term "ectopic" and "heterotropic" can be used interchangeably herein.

As used herein, "local administration" or "local delivery," refers to delivery that does not rely upon transport of the composition or agent to its intended target tissue or site via the vascular system. For example, the composition may be delivered by injection or implantation of the composition by injection or implantation of a device containing the composition. Following local administration in the vicinity of a target tissue or site, the composition or agent, or one or more components thereof, may diffuse to the intended target tissue or site.

The term "sample" refers to a collection of fluids, cells or tissues isolated from a subject. Biological fluids are typically liquids at physiological temperatures and may include naturally occurring fluids present in, withdrawn from, expressed or otherwise extracted from a subject or biological source. Examples of biological fluids include blood, serum, serosal fluids, plasma, lymph, urine, cerebrospinal fluid, saliva, ocular fluids, cystic fluid, tear drops, feces, sputum, mucosal secretions, vaginal secretions, gynecological fluids, ascites fluids such as those associated with non-solid tumors, fluids of the pleural, pericardial, peritoneal, abdominal and other body cavities, fluids collected by bronchial lavage and the like.

The term "control sample", as used herein, refers to any clinically relevant control sample, including, for example, a sample from a healthy subject or a sample made at an earlier timepoint from the subject to be assessed.

II. Compositions

In one aspect, the present disclosure provides compositions that are suitable for implantation into a subject comprising a first cell population comprising parenchymal cells, endothelial cells, or a combination thereof; and a second cell population comprising genetically engineered immunomodulatory cells which inhibit an immune response to the first cell population.

The present disclosure provides a composition suitable for implantation into a host comprising a first cell population comprising parenchymal cells, endothelial cells, or a combination thereof, wherein the cells of the first population are not genetically engineered; and a second cell population comprising genetically engineered immunomodulatory cells which inhibit an immune response to the first cell population.

It is understood that the cell compositions disclosed herein may contain parenchymal cells with one, or two or more types of non-parenchymal cells such as, for example, stromal cells, endothelial cells, stellate cells, cholangiocytes (bile duct cells), Kupffer cells, pit cells, etc. In some embodiments, the parenchymal cells (e.g., hepatocytes) are cultured in heterotypic contact with a second population of non-parenchymal cells. In some embodiments, the cellular composition may contain more than one non-parenchymal cell population. In some embodiments, the composition contains an additional (e.g., third) non-parenchymal cell population that is not genetically modified. In some embodiments, the composition contains an additional (e.g., third) genetically engineered non-parenchymal cell population. One of skill in the art will appreciate that particular patterns of non-parenchymal cells surrounding the parenchymal cells may be desired in some cases, e.g., when it is desired to mimic certain in vivo environments. It is understood that any support or accessory cells may be included in the cell compositions and implantable grafts disclosed herein.

Further cell types which can be included in the cellular compositions and implantable grafts disclosed herein include pancreatic cells (alpha, beta, gamma, delta), enterocytes, renal epithelial cells, astrocytes, muscle cells, brain cells, neurons, glia cells, respiratory epithelial cells, lymphocytes, erythrocytes, blood-brain barrier cells, kidney cells, cancer cells, normal or transformed fibroblasts, liver progenitor cells, oval cells, adipocytes, osteoblasts, osteoclasts, myoblasts, beta-pancreatic islets cells, stem cells (e.g., embryonic stem cells, hematopoietic stem cells, mesenchymal stem cells, endothelial stem cells, etc.), cells described, for example, in US 2006/0258000, which is incorporated herein by reference, myocytes, keratinocytes, and indeed any cell type that adheres to a substrate.

A. Cell Populations

In some aspects, the first cell population in the compositions and implantable grafts described herein is composed of human parenchymal cells, endothelial cells, or a combination thereof. In some aspects, the first cell population in the compositions and implantable grafts described herein is composed of human parenchymal cells, vascular cells, or a combination thereof.

In some aspects, the first cell population comprises parenchymal cells. In some aspects, the first population of cells contains parenchymal cells having a specific morphology, phenotype and/or highly differentiated function. Exemplary parenchymal cells include, but are not limited to hepatocytes, chondrocytes, adipocytes, myocytes, pancreatic cells (e.g., pancreatic exocrine cells, pancreatic islet cells), splenocytes, kidney cells, enterocytes, neurons, biliary cells, Kupffer cells, stellate cells, cardiac muscle cells, alveolar cells, bronchiolar cells, club cells, urothelial cells, mucous cells, parietal cells, chief cells, G cells, goblet cells, enteroendocrine cells, Paneth cells, M cells, tuft cells, glial cells, gall bladder cells, keratinocytes, melanocytes, Merkel cells, Langerhans cells, osteocytes, osteoclasts, esophageal cells, photoreceptor cells, corneal epithelial cells and other parenchymal cells described herein.

In certain embodiments, parenchymal cells are optimized to maintain the appropriate morphology, phenotype and cellular function conducive to use in the methods of the disclosure. Primary parenchymal cells can be isolated and/or pre-cultured under conditions optimized to ensure that the parenchymal cells of choice (e.g., hepatocytes) initially have the desired morphology, phenotype and cellular function and, thus, are poised to maintain said morphology, phenotype and/or function in the compositions and implantable grafts described herein, and in vivo upon implantation.

In some aspects, the first cell population comprises primary hepatocytes, vascular endothelial cells, or genetically engineered cells thereof that support the specific morphology, phenotype and/or highly differentiated function and/or viability of the first population of parenchymal cells.

In other aspects, the first cell population comprises endothelial cells. In some embodiments, the endothelial cells in the first cell population are umbilical vein endothelial cells, liver endothelial cells, brain endothelial cells, lung endothelial cells, kidney endothelial cells, cardiac endothelial cells, spleen endothelial cells, testis endothelial cells, lymphatic endothelial cells or bone marrow endothelial cells.

In some aspects, the compositions and implantable grafts of the disclosure comprises a second population of cells which are genetically engineered to modulate the immune response to the first population of cells following transplantation into a host.

In some aspects, the second cell population comprises genetically engineered non-parenchymal cells. In some embodiments, the second population of cells comprises genetically engineered non-parenchymal cells which support the specific morphology, phenotype and/or highly differentiated function and/or viability of the first population of parenchymal cells.

In some embodiments, the genetically engineered non-parenchymal cells are stromal cells. In some embodiments, the genetically engineered stromal cells are multipotent stromal cells. In some embodiments, the multipotent stromal cells are derived from bone-marrow. In some embodiments, the genetically engineered multipotent stromal cells are derived from non-marrow tissues.

In some embodiments, the genetically engineered cells are endothelial cells, fibroblasts or pericytes. In some embodiments, the genetically engineered endothelial cells are umbilical vein endothelial cells, liver endothelial cells, brain endothelial cells, lung endothelial cells, kidney endothelial cells, cardiac endothelial cells, spleen endothelial cells, testis endothelial cells, lymphatic endothelial cells or bone marrow endothelial cells. Endothelial cells can be obtained as disclosed above.

In some aspects, the second cell population is genetically engineered to express a molecule (e.g., protein, peptide) which suppresses or inhibits activation of an immune response pathway including, but not limited to, an innate immune response, adaptive immune response, antigen presentation and antibody production.

In some aspects, the second cell population is genetically engineered to activate an immune checkpoint pathway. In some embodiments, the second cell population contains stromal cells genetically engineered to express a molecule (e.g., peptide, protein) which activates an immune checkpoint pathway. In some embodiments, the second cell population contains endothelial cells genetically engineered to express a molecule (e.g., peptide, protein) which activates an immune checkpoint pathway. In some embodiments, the second cell population contains stromal cells and endothelial cells wherein one or both cell types have been genetically engineered to activate an immune checkpoint pathway.

In "not triggering" or "suppressing" the immune response, it will be understood by those of ordinary skill in the art that this does not require that the immune system of the host lies absolutely dormant, but merely that any activity of the immune system with respect to the transplanted cells does not rise to a level that prevents, suppresses, or negates the regeneration of tissue (e.g., a level of activity that would be seen with non-engineered xenogeneic cells). In other words, a state of immunotolerance (cell anergy) is provided. In some embodiments, the compositions and implantable grafts disclosed provided herein can be engineered to express at least one gene (i.e., a gene or genes) that serves to suppress or prevent the stimulation of an immune response by the host (once the cell or cells are transplanted into the host). Many such candidate genes are known to those of ordinary skill in the art.

The term "immunological activity" as used herein in the context of mammalian lymphocytes refers to one or more cell survival, cell proliferation, cytokine production (e.g. interferon-gamma), or T-cell cytotoxicity activities. Methods to assay the immunological activity of engineered cells, including to evaluate the activity of the immunomodulatory protein, are known in the art and include, but are not limited to, the ability to expand T cells following antigen stimulation, sustain T cell expansion in the absence of re-stimulation, and anti-cancer activities in appropriate animal models. Assays also include assays to assess cytotoxicity, including a standard $^{51}$Cr-release assay (see e.g. Milone et al., (2009) Molecular Therapy 17: 1453-1464) or flow based cytotoxicity assays, or an impedance based cytotoxicity assay (Peper et al. (2014) Journal of Immunological Methods, 405:192-198). Assays to assess immunological activity of engineered cells can be compared to control non-engineered cells or to cells containing one or more other engineered recombinant receptors (e.g. antigen receptor) with a known activity.

In some aspects, the second cell population is genetically engineered to activate one or more checkpoint pathways to induce immune cell exhaustion and anergy to the cells present in the first cell population. For example, in some embodiments, the second cell population imparts inhibitory signals to immune cells surveying the grafted cells, such that the grafted cells are not rejected by Human Leukocyte Antigen (HLA)-mismatched T cells. In some embodiments, the presence of the second cell population results in expression of exhaustion markers on T cells. In some embodiments, the exhaustion markers are PD-1, LAG-3 and TIM-3.

In some aspects, the second cell population can also secrete or produce factors, e.g., soluble factors, or biochemical cues that support said morphology, phenotype, function or viability. For example, the second population of cells in the composition can secrete, e.g., growth factors and/or cytokines that promote vascularization of the constructs in vivo. In some embodiments, the non-parenchymal cells in the second cell population enhance vascular recruitment to the site of the implanted cell mixture or cell aggregate. For example, non-parenchymal cells within the second cell population of the compositions disclosed herein can be selected based on their ability to secrete one or more pro-angiogenic factors. Exemplary pro-angiogenic factors include, but are not limited to, vascular endothelial growth factor (VEGF), including isoforms A, B, C, and D, basic fibroblast growth factor (bFGF), interleukin-6 (IL-6), and other inflammatory cytokines, tumor necrosis factor alpha (TNF a), hepatocyte growth factor (HGF) and the like. Non-parenchymal cells can be selected that secret such factors, or can be engineered (e.g., recombinantly engineered) to secrete such factors.

Cells useful in the engineered cell mixtures and methods of the disclosure are available from a number of sources including commercial sources. For example, parenchymal cells can be obtained from a variety of sources including, but not limited to, liver, skin, pancreas, neuronal tissue, muscle (e.g., heart and skeletal), stem cells, and the like. Parenchymal cells can be obtained from parenchymal tissue using any one of a host of art-described methods for isolating cells from a biological sample, e.g., a human biological sample. Parenchymal cells. (e.g., human parenchymal cells), can be obtained by biopsy or from cadaver tissue. In certain embodiments, parenchymal cells are derived from lung, kidney, nerve, heart, fat, bone, muscle, thymus, salivary gland, pancreas, adrenal, spleen, gall bladder, liver, thyroid, parathyroid, small intestine, uterus, ovary, bladder, skin, testes, prostate, or mammary gland. In general, cells also may be obtained by perfusion methods or other methods known in the art, such as those described in U.S. Application No. 20060270032. Cells useful in the engineered cell mixtures and methods of the disclosure also are available from a number of sources including commercial sources. For example, hepatocytes may be isolated by conventional methods (Berry and Friend, 1969, J. Cell Biol. 43:506-520) which can be adapted for human liver biopsy or autopsy material.

Cells can be from established cell lines or they can be primary cells, where "primary cells", "primary cell lines", and "primary cultures" are used interchangeably herein to refer to cells and cells cultures that have been derived from a and allowed to grow in vitro for a limited number of passages, i.e. splittings, of the culture. For example, primary cultures can be cultures that have been passaged 0 times, 1 time, 2 times, 4 times, 5 times, 10 times, or 15 times, but not enough times go through the crisis stage. Primary cell lines can be maintained for fewer than 10 passages in vitro. Target cells can be in many examples unicellular organisms or can be grown in culture.

If the cells are primary cells, such cells can be harvested from an individual by any convenient method. For example, cells from tissues such as skin, muscle, bone marrow, spleen, liver, pancreas, lung, intestine, stomach, etc. are most conveniently harvested by biopsy. An appropriate solution can be used for dispersion or suspension of the harvested cells. Such solution will generally be a balanced salt solution, e.g. normal saline, phosphate-buffered saline (PBS), Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc. The cells can be used immediately, or they can be stored, frozen, for long periods of time, being thawed and capable of being reused. In such cases, the cells will usually be frozen in 10% DMSO, 50% serum, 40% buffered medium, or some other such solution as is commonly used in the art to preserve cells at such freezing temperatures and thawed in a manner as commonly known in the art for thawing frozen cultured cells.

B. Production of Genetically Engineered Cells

In some aspects, the compositions and implantable grafts described herein comprise genetically engineered cells. For example, in some embodiments, cells are genetically engineered to express or overexpress an immunomodulatory protein.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

Methods of introducing a nucleic acid into a host cell also are known in the art, and any known method can be used to introduce a nucleic acid (e.g., an expression construct) into a cell. Nucleotides encoding a guide RNA (introduced either as DNA or RNA) and/or a site-directed modifying polypeptide (introduced as DNA or RNA) and/or a donor polynucleotide can be provided to the cells using well-developed transfection techniques; see, e.g. Angel and Yanik (2010) PLoS ONE 5(7): e 11756, and the commercially available TransMessenger® reagents from Qiagen, Stemfect™ RNA Transfection Kit from Stemgent, and TransIT®-mRNA Transfection Kit from Mims Bio LLC (See, also Beumer et al. (2008) Efficient gene targeting in Drosophila by direct embryo injection with zinc-finger nucleases. PNAS 105(50): 19821-19826).

In some embodiments, the nucleic acid encoding the immunomodulatory molecule can be packaged into or on the surface of delivery vehicles for delivery to cells. Delivery vehicles contemplated include, but are not limited to, nanospheres, liposomes, quantum dots, nanoparticles, polyethylene glycol particles, hydrogels, and micelles. As described in the art, a variety of targeting moieties can be used to enhance the preferential interaction of such vehicles with desired cell types or locations.

Introduction of the complexes, polypeptides, and nucleic acids of the disclosure into cells can occur by viral or bacteriophage infection, transfection, conjugation, protoplast fusion, lipofection, electroporation, nucleofection, calcium phosphate precipitation, polyethyleneimine (PEI)-mediated transfection, DEAE-dextran mediated transfection, liposome-mediated transfection, particle gun technology, calcium phosphate precipitation, direct micro-injection, nanoparticle-mediated nucleic acid delivery, and the like.

Alternatively, nucleic acids can be provided in an expression vector. Many vectors, e.g. plasmids, cosmids, minicircles, phage, viruses, etc., useful for transferring nucleic acids into target cells are available. The vectors comprising the nucleic acid(s) can be maintained episomally, e.g. as plasmids, minicircle DNAs, viruses such cytomegalovirus, adenovirus, etc., or they can be integrated into the target cell genome, through homologous recombination or random integration, e.g. retrovirus-derived vectors such as MMLV, HIV-1, ALV, etc.

i. Immunomodulatory Molecules

In some embodiments, the compositions and implantable grafts described herein comprise cells genetically engineered to express or overexpress at least one immunomodulatory molecule. Immunomodulatory molecules which may be utilized to genetically engineer cells (e.g., nucleic acid molecules such as DNA, RNA, mRNA, RNAi) are well known in the art and exemplary targets for such molecules are also well known in the art and exemplary such molecules are disclosed herein. When expressing proteins (e.g., using mRNA), such proteins can be a full-length protein or, alternatively, a functional fragment thereof (e.g., a fragment of the full-length protein that includes one or more functional domains such that the functional activity of the full-length protein is retained). Furthermore, in certain embodiments, the protein encoded by a nucleic acid in the genetically engineered cells can be a modified protein, e.g., can comprise one or more heterologous domains, e.g., the protein can be a fusion protein that contains one more domains that do not naturally occur in the protein such that the function of the protein is altered.

In some aspects, the immunomodulatory molecule modulates a naturally-occurring target (e.g., up- or down-regulates the activity of a naturally-occurring target) of an immune cell (e.g., a T cell, B cell, myeloid cell, dendritic cell) to suppress immune activation. The immunomodulatory molecule may itself encode the naturally-occurring target or may function to modulate a naturally-occurring target (e.g., in a cell in vivo, such as in a subject). The naturally-occurring target can be a full-length target, such as a full-length protein, or can be a fragment or portion of a naturally-occurring target, such as a fragment or portion of a protein. The agent that modulates a naturally-occurring target (e.g., by encoding the target itself or by functioning to modulate the activity of the target) can act in an autocrine fashion, i.e., the agent exerts an effect directly on the cell into which the agent is delivered. Additionally, or alternatively, the agent that modulates a naturally-occurring target can function in a paracrine fashion, i.e., the agent exerts an effect indirectly on a cell other than the cell into which the agent is delivered (e.g., delivery of the agent into one type of cell results in secretion of a molecule that exerts effects on another type of cell, such as bystander cells). Agents that modulate naturally-occurring targets include nucleic acid molecules that induce (e.g., enhance, stimulate, upregulate) protein expression, such as mRNAs and DNA. Agents that modulate naturally-occurring targets also include nucleic acid molecules that reduce (e.g., inhibit, decrease, downregulate) protein expression, such as siRNAs, miRNAs and antagomirs. Non-limiting examples of naturally-occurring targets include soluble proteins (e.g., secreted proteins), intracellular proteins (e.g., intracellular signaling proteins, transcription factors) and membrane-bound or transmembrane proteins (e.g., receptors).

In some aspects, immune tolerance observed in the setting of allogeneic and xenogeneic cell, tissue or organ transplantation suggests that T cells continuously exposed to antigen become progressively inactivated through a process termed "exhaustion." Exhausted T cells are characterized by the expression of T cell negative regulatory receptors, predominantly CTLA-4, PD-1, LAG-3 and TIM-3, whose action is to limit the ability of immune cells to proliferate, produce cytokines, and kill target cells and/or to increase Treg activity. Crespo, J., et al. (2013) Curr. Opin. Immunol. 25(2): 214-22.

Accordingly, in some aspects, the cells of the second cell population are genetically engineered to express a protein which activates one or more checkpoint pathways to induce immune cell exhaustion and anergy to the cells present in the first cell population. In some embodiments, the second cell population are genetically engineered to express an immune checkpoint protein. Suitable immune checkpoint proteins include, but are not limited to, PD-1, PD-L1, PDL-2, CD47, CD39, CD73, CD200, HVEC, CEACAM1, CD155TIM-3, LAG-3, CTLA-4, A2AR, B7-H3, B7-H4, HLA-E, BTLA, IDO, KIR, VISTA or a combination thereof. In some embodiments, the immune checkpoint protein is PD-L1, CD47, HLA-E, CD39, CD73, or a combination thereof. The nucleic acid and amino acid sequences of immune checkpoint proteins are known in the art, and many are commercially available (e.g., G&P Bio).

In certain embodiments, the cells in the second cell population are genetically engineered to express a molecule in the PD-1 signaling pathway. Programmed Cell Death 1 (PD-1) is a member of the CD28 family of T cell co-stimulatory receptors and is primarily expressed on activated T cells, B cells, myeloid cells and natural killer (NK) cells (Dong H, et al., Nat Med. 1999; 5:1365-1369; Terme M, et al., Cancer Res. 2011; 71:5393-5399). The nucleic acid and amino acid sequences of a human PD-1 are publicly available (GenBank Accession Nos. NM_005018.2 and NP_005009.2; U.S. Pat. No. 5,698,520). PD-1 ligands, PD-L1 (also known as B7-H1 and CD274; Freeman et al. (2000) J. Exp. Med. 192: 1027) and PD-L2 (also known as B7-DC and CD273; Latchman et al. (2001) Nat. Immunol. 2:261), are members of the B7 family of polypeptides. Binding of PD-1 by its ligands results in down-regulation of T cell activation and PD-1 plays a critical role in the regulation of T cell activation and tolerance (Keir M E, et al., Annu Rev Immunol 2008; 26:677-704).

In other embodiments, the cells in the second cell population are genetically engineered to express PD-L2 (Accession: NP_079515.2; Accession: XP_005251657.1). PD-L2 is a ligand for the PD-1 receptor. Engagement of PD-1 by PD-L2 dramatically inhibits T cell receptor (TCR)-mediated proliferation and cytokine production by CD4+ T cells. At low antigen concentrations, PD-L2-PD-1 interactions inhibit strong B7-CD28 signals. In contrast, at high antigen concentrations, PD-L2-PD-1 interactions reduce cytokine production but do not inhibit T cell proliferation. (Latchman et al. Nat. Immunol. 2:261-268, 2001).

In other embodiments, the cells in the second cell population are genetically engineered to express CD47 (Cluster of Differentiation 47). CD47 belongs to the immunoglobulin superfamily and partners with membrane integrins and also binds the ligands thrombospondin-1 (TSP-1) and signal-regulatory protein alpha (SIRP α), a membrane protein which is involved in the increase in intracellular calcium concentration that occurs upon cell adhesion to extracellular matrix (Accession NP_001317657.1).

In other embodiments, the cells in the second cell population are genetically engineered to express CD73, an Ecto-5-prime-nucleotidase which catalyzes the conversion at neutral pH of purine 5-prime mononucleotides to nucleosides, the preferred substrate being AMP. (Accession NP_002517.1). CD73 is the rate-limiting enzyme in the production of extracellular adenosine from ATP and has been associated to play a key role in driving immune evasion, e.g., in cancer cells.

In other embodiments, the cells in the second cell population are genetically engineered to express CD39, a cell surface-located ectonucleotidase that catalyzes the hydrolysis of γ- and β-phosphate residues of triphospho- and diphosphonucleosides to the monophosphonucleoside derivative (Accession NP_001157651.1)

In some embodiments, the cells are genetically engineered to express CD200, a type I membrane glycoprotein containing two extracellular immunoglobulin domains, a transmembrane and a cytoplasmic domain. This gene is expressed by various cell types, including B cells, a subset of T cells, thymocytes, endothelial cells, and neurons. The encoded protein plays an important role in immunosuppression and regulation of anti-tumor activity. Alternative splicing results in multiple transcript variants encoding different isoforms. (Accession NP_001305755.1)

In some embodiments, the cells are genetically engineered to express B7-H3 (Accession NP_001019907). B7-H3 is a member of the B7/CD28 superfamily of costimulatory molecules serving as an accessory modulator of T-cell response. B7-H3 protein is found on osteoblasts, fibroblasts, fibroblast-like synoviocytes, and epithelial cells as well as in human liver, lung, bladder, testis, prostate, breast, placenta, and lymphoid organs.

In other embodiments, the cells are genetically engineered to express B7-H4, a member of the B7 family of proteins and is involved in T cell signaling pathways. B7-H4 is a negative regulator of T cell responses. Human and mouse B7-H4 share 87% amino acid identity suggesting an important evolutionarily conserved function. Human and mouse B7-H4 mRNAs are expressed broadly in both lymphoid (spleen and thymus) and nonlymphoid organs (including lung, liver, testis, ovary, placenta, skeletal muscle, pancreas, and small intestine), however B7-H4 protein is not detected in normal human tissues by immunohistochemistry. B7-H4 peptides are described, for example, in WO 2011/026132.

In some embodiments, the cells in the second cell population are genetically engineered to express cytotoxic T-lymphocyte-associated antigen 4 (CTLA-4; also known as CD152). CTLA4 is a receptor expressed exclusively on T cells where it regulates the amplitude of the early stages of T cell activation by counteracting the activity of the T cell co-stimulatory receptor, CD28 (Schwartz et al., Cell (1992) 71:1065-1068; Rudd et al., Immunol. Rev. (2009) 229:12-26). The amino acid and nucleotide sequence of human CTLA-4 are publicly available (U.S. Pat. Nos. 5,811,097 and 5,434,131). CD28 and CTLA4 share identical ligands: CD80 (also known as B7.1) and CD86 (also known as B7.2). The major physiological role of CTLA4 seems to be through distinct effects on the two major subsets of $CD4^+$ T cells: downmodulation of helper T cell activity and enhancement of regulatory T ($T_{Reg}$) cell immunosuppressive activity (Peggs et al., J. Exp. Med (2009) 206:1717-1725).

In some embodiments, the cells in the second cell population are genetically engineered to express lymphocyte activation gene-3 (LAG-3; CD223). LAG-3 is a type I transmembrane protein that is expressed on the cell surface of activated CD4+ and CD8+ T cells and subsets of NK and dendritic cells (Triebel F, et al., J. Exp. Med. (1990) 171: 1393-1405; Workman C J, et al., J. Immunol. (2009) 182 (4):1885-91; US 2011/0180892). Nucleic acid and polypeptide sequences of human LAG-3 are well known in the art and are publicly available (GenBank Accession Nos. NM_002286.5 and NP_002277.4). LAG-3 has been shown to have a role in enhancing the function of Treg cells (Huang et al, Immunity (2004) 21:503-513; Goldberg et al., Curr. Top. Microbiol. Immuno. (2011) 344:269-278) and to inhibit CD8+ effector T cell functions (Grosso et al., J. Clin. Invest. (2007) 117:3383-3392). The only known ligand for LAG3 is MHC class II molecules.

In other embodiments, cells in the second cell population are genetically engineered to express TIM3. TIM3 is a member of the T cell/transmembrane, immunoglobulin, and mucin (TIM) gene family. Nucleic acid and polypeptide sequences of human TIM-3 are well known in the art and are publicly available (GenBank Accession Nos. NM_032782.4 and NP_116171.3; US 2013/0156774). TIM-3 is expressed on a subset of activated CD4+ T cells, on differentiated Th1 cells, on some CD8+ T cells, and at lower levels on Th2 cells (Hastings et al., Eur. J. Immunol. (2009) 39:2492-2501).

Binding of the ligand, galectin 9, inhibits T helper 1 ($T_H1$) cell response (Zhu et al., Nature Immunol. (2005) 6:1245-1252).

Additional immunomodulatory proteins for use in the genetically engineering the second population also include but are not limited to HLA-E (Accession NP_005507.3), Herpesvirus entry mediator (HVEM) (Accession NP_003811.2); Carcinoembryonic antigen-related cell adhesion molecule 1 (biliary glycoprotein) (CEACAM1) (Accession: NP_001703.2); and/or CD155 (Accession: NP_001129241.1).

ii. Vectors

In another aspect, provided is a recombinant expression vector comprising a nucleic acid encoding an immunomodulatory protein under the operable control of a signal sequence for secretion and the encoded immunomodulatory protein is secreted when expressed from a cell. In some embodiments, the signal sequence for secretion encodes a secretory signal peptide.

In another aspect, the genetically engineered immunomodulatory cells of the second cell population comprise a vector which expresses the protein. In some aspects, the expression vectors are capable of expressing the immunomodulatory proteins in an appropriate cell under conditions suited to expression of the protein. In some aspects, the expression vector comprises the DNA molecule that encodes the immunomodulatory protein operatively linked to appropriate expression control sequences. Methods of affecting this operative linking, either before or after the DNA molecule is inserted into the vector, are well known. Expression control sequences include promoters, activators, enhancers, operators, ribosomal binding sites, start signals, stop signals, cap signals, polyadenylation signals, and other signals involved with the control of transcription or translation.

In some embodiments, the vector further comprises nucleotide sequence that encodes a secretory or signal peptide operably linked to the nucleic acid encoding the immunomodulatory protein, thereby allowing for secretion of the immunomodulatory protein.

The term "operably linked" means that the nucleotide sequence of interest is linked to regulatory sequence(s) in a manner that allows for expression of the nucleotide sequence. The term "regulatory sequence" is intended to include, for example, promoters, enhancers and other expression control elements (e.g., polyadenylation signals). Such regulatory sequences are well known in the art and are described, for example, in Goeddel; Gene Expression Technology: Methods in Enzymology 185, Academic Press, San Diego, CA (1990). Regulatory sequences include those that direct constitutive expression of a nucleotide sequence in many types of host cells, and those that direct expression of the nucleotide sequence only in certain host cells (e.g., tissue-specific regulatory sequences). It will be appreciated by those skilled in the art that the design of the expression vector can depend on such factors as the choice of the target cell, the level of expression desired, and the like.

Expression vectors contemplated include, but are not limited to, viral vectors (e.g. based on vaccinia virus; poliovirus; adenovirus; adeno-associated virus; SV40; herpes simplex virus; herpes papilloma virus; human immunodeficiency virus; a retrovirus (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, mammary tumor virus; and other recombinant vectors.

Other vectors contemplated for eukaryotic target cells include, but are not limited to, the vectors: pXT1, pSG5, pSVK3, pBPV, pMSG, and pSVLSV40 (Pharmacia). Other vectors can be used as long as they are compatible with the host cell.

In some embodiments, the vector is a viral vector. In some embodiments, the recombinant expression vector is a viral vector, including but not limited both integrating and non-integrating viral vectors. Exemplary viral vectors include, but are not limited to adenoviral vectors, lentiviral vectors, retroviral vectors, adeno-associated virus, SV40, herpes simplex virus, a herpes papilloma virus, episomal vectors, and non-episomal vectors, and are disclosed for example, in U.S. Pat. Nos. 8,119,772; 8,552,150; 6,277,633 and 6,521,457; and U.S. Patent Application Publication Nos. 2012/0135034 and 2008/0254008. Lentiviral vector systems are also commercially available from, e.g., Cell Biolabs, Inc. of San Diego, Calif., United States of America and OriGene Technologies, Inc. of Rockville, Md., United States of America. In some embodiments, a vector is a viral episomal vector, optionally based on adenovirus and/or adeno-associated virus (AAV), for example, as described in WO 2002/085287. One example of a suitable non-viral episomal vector is disclosed in WO 1998/007876.

In some embodiments, the viral vector is a lentivirus, a vaccinia virus, poliovirus, adenovirus, adeno-associated virus, SV40, herpes simplex virus, a herpes papilloma virus, or a retrovirus. In certain embodiments, the vector is a lentiviral vector.

In some embodiments, expression of the immunomodulatory protein is controlled by a promoter to enhance to control or regulate expression. The promoter is operably linked to the portion of the nucleic acid molecule encoding the immunomodulatory protein. In some embodiments, expression of the protein is under the control of a constitutively active promoter, an inducible promoter, a tissue specific promoter, a cell-type specific promoter or a temporally restricted promoter. In some embodiments, the immunomodulatory protein is expressed and secreted by the engineered cell after the engineered cell is contacted with an inducing agent. In some embodiments, the immunomodulatory protein is expressed and secreted by the engineered cell upon T cell activation signaling.

A promoter can be a constitutively active promoter (i.e., a promoter that is constitutively in an active/"ON" state), it can be an inducible promoter (i.e., a promoter whose state, active/"ON" or inactive/"OFF", is controlled by an external stimulus, e.g., the presence of a particular temperature, compound, or protein.), it can be a spatially restricted promoter (i.e., transcriptional control element, enhancer, etc.) (e.g., tissue specific promoter, cell type specific promoter, etc.), and it can be a temporally restricted promoter (i.e., the promoter is in the "ON" state or "OFF" state during specific stages of embryonic development or during specific stages of a biological process, e.g., hair follicle cycle in mice).

In some embodiments, the promoter can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., Nature Biotechnology (2002) 20:497-500), an enhanced U6 promoter (e.g., Xia et al., Nucleic Acids Res. (2003) September 1, 31(17)), a human H1 promoter (H1), and the like.

Non-limiting examples of suitable eukaryotic promoters (i.e., promoters functional in a eukaryotic cell) include those from cytomegalovirus (CMV) immediate early, herpes simplex virus (HSV) thymidine kinase, early and late SV40, long terminal repeats (LTRs) from retrovirus, human elongation factor-1 promoter (EF1), a hybrid construct comprising the cytomegalovirus (CMV) enhancer fused to the chicken beta-actin promoter (CAG), murine stem cell virus promoter (MSCV), phosphoglycerate kinase-1 locus promoter (PGK), and mouse metallothionein-I.

Exemplary constitutive promoters include the Simian vacuolating virus 40 (SV40) promoter, the cytomegalovirus (CMV) promoter, the ubiquitin C (UbC) promoter, and the EF-1 alpha (EF1a) promoter. In some embodiments, the constitutive promoter is tissue specific. For example, in some embodiments, the promoter allows for constitutive expression of the immunomodulatory protein in specific tissues, such as immune cells, lymphocytes, or T cells. Exemplary tissue-specific promoters are described in U.S. Pat. No. 5,998,205, including, for example, a fetoprotein, DF3, tyrosinase, CEA, surfactant protein, and ErbB2 promoters.

Examples of inducible promoters include, but are not limited to T7 RNA polymerase promoter, T3 RNA polymerase promoter, Isopropyl-beta-D-thiogalactopyranoside (IPTG)-regulated promoter, lactose induced promoter, heat shock promoter, Tetracycline-regulated promoter (e.g., Tet-ON, Tet-OFF, etc.), Steroid-regulated promoter, Metal-regulated promoter, estrogen receptor-regulated promoter, etc. Inducible promoters can therefore be regulated by molecules including, but not limited to, doxycycline; RNA polymerase, e.g., T7 RNA polymerase; an estrogen receptor; an estrogen receptor fusion; etc.

In some embodiments, the promoter is a chemically inducible promoter, e.g., which is tetracycline-dependent, lac-dependent, pBad-dependent, AlcA-dependent, or LexA-dependent. In some embodiments, the promoter is a temperature inducible promoter, for example, a Hsp70- or Hsp90-derived promoter.

In some embodiments, the promoter is a spatially restricted promoter. In some embodiments, the spatially restricted promoter is a liver-specific promoter, a cardiomyocyte-specific promoters, a smooth muscle-specific promoter, or a photoreceptor-specific promoter.

Spatially restricted promoters can also be referred to as enhancers, transcriptional control elements, control sequences, etc. Any convenient spatially restricted promoter can be used and the choice of suitable promoter (e.g., a liver-specific promoter, a brain specific promoter, a promoter that drives expression in a subset of neurons, a promoter that drives expression in the germline, a promoter that drives expression in the lungs, a promoter that drives expression in muscles, a promoter that drives expression in islet cells of the pancreas, etc.) will depend on the organism. For example, various spatially restricted promoters are known for plants, flies, worms, mammals, mice, etc. Thus, a spatially restricted promoter can be used to regulate the expression of a nucleic acid encoding a site-directed polypeptide in a wide variety of different tissues and cell types, depending on the organism. Some spatially restricted promoters are also temporally restricted such that the promoter is in the "ON" state or "OFF" state during specific stages of embryonic development or during specific stages of a biological process (e.g., hair follicle cycle in mice).

Examples of spatially restricted promoters include, but are not limited to, liver-specific promoters, neuron-specific promoters, adipocyte-specific promoters, cardiomyocyte-specific promoters, smooth muscle-specific promoters, photoreceptor-specific promoters, etc.

Cardiomyocyte-specific spatially restricted promoters include, but are not limited to, control sequences derived from the following genes: myosin light chain-2, a-myosin heavy chain, AE3, cardiac troponin C, cardiac actin, and the like. Franz et al., Cardiovasc. Res. (1997) 35:560-566; Robbins et al., Ann. N.Y. Acad. Sci. (1995) 752:492-505; Linn et al., Circ. Res. (1995) 76:584591; Parmacek et al., Mol. Cell. Biol. (1994) 14:1870-1885; Hunter et al., Hypertension (1993) 22:608-617; and Sartorelli et al., Proc. Natl. Acad. Sci. USA (1992) 89:4047-4051.

Smooth muscle-specific spatially restricted promoters include, but are not limited to, an SM22a promoter (see, e.g., Akyilrek et al. *Mol. Med.* (2000) 6:983; and U.S. Pat. No. 7,169,874); a smoothelin promoter (see, e.g., WO 2001/018048); an a-smooth muscle actin promoter; and the like. For example, a 0.4 kb region of the SM22a promoter, within which lie two CArG elements, has been shown to mediate vascular smooth muscle cell-specific expression (see, e.g., Kim, et al., Mol. Cell. Biol. (1997) 17: 2266-2278; Li, et al., J. Cell Biol. (1996) 132:849-859; and Moessler, et al., Development (1996) 122:2415-2425).

Photoreceptor-specific spatially restricted promoters include, but are not limited to, a rhodopsin promoter; a rhodopsin kinase promoter (Young et al., *Ophthalmol. Vis. Sci.* (2003) 44:4076); a beta phosphodiesterase gene promoter (Nicoud et al., *J. Gene Med.* (2007) 9:1015); a retinitis pigmentosa gene promoter (Nicoud et al. (2007), supra); an interphotoreceptor retinoid-binding protein (IRBP) gene enhancer (Nicoud et al. (2007), supra); an IRBP gene promoter (Yokoyama et al. *Exp. Eye Res.* (1992) 55:225); and the like.

Other promoters which can be used include an SV40 early promoter, a mouse mammary tumor virus long terminal repeat (LTR) promoter, an adenovirus major late promoter (Ad MLP), a herpes simplex virus (HSV) promoter, a cytomegalovirus (CMV) promoter, a rous sarcoma virus (RSV) promoter, a human U6 small nuclear promoter (U6), an enhanced U6 promoter, a human H1 promoter (H1).

In further embodiments, an inducible promoter is operatively linked to the nucleic acid molecule encoding the immunomodulatory protein such that expression of the nucleic acid is controllable by controlling the presence or absence of the appropriate inducer of transcription. For example, the promoter can be a regulated promoter and transcription factor expression system, such as the published tetracycline-regulated systems or other regulatable systems (see, e.g. published International PCT Appl. No. WO 01/30843), to allow regulated expression of the encoded polypeptide. An exemplary regulatable promoter system is the Tet-On (and Tet-Off) system available, for example, from Clontech (Palo Alto, CA). This promoter system allows the regulated expression of the transgene controlled by tetracycline or tetracycline derivatives, such as doxycycline. Other regulatable promoter systems are known (see e.g., published U.S. Application No. 2002-0168714, entitled "Regulation of Gene Expression Using Single-Chain, Monomeric, Ligand Dependent Polypeptide Switches," which describes gene switches that contain ligand binding domains and transcriptional regulating domains, such as those from hormone receptors).

In some embodiments, the promotor is responsive to an element responsive to T-cell activation signaling. Solely by way of example, in some embodiments, an engineered T cell comprises an expression vector encoding the immunomodulatory protein and a promotor operatively linked to control expression of the immunomodulatory protein. The engineered T cell can be activated, for example by signaling through an engineered T cell receptor (TCR) or a chimeric antigen rector (CAR), and thereby triggering expression and secretion of the immunomodulatory protein through the responsive promotor expressed in response to a nuclear factor of activated T-cells (NFAT) or nuclear factor kappa-light-chain enhancer of activated B cells (NF-κB). For example, in some embodiments, the inducible promoter comprises a binding site for NFAT or NF-κB. For example, in some embodiments, the promoter is an NFAT or NF-κB promoter or a functional variant thereof. Thus, in some embodiments, the nucleic acids make it possible to control the expression of immunomodulatory protein while also reducing or eliminating the toxicity of the immunomodulatory protein. In particular, engineered immune cells comprising the nucleic acids of the invention express and secrete the immunomodulatory protein only when the cell (e.g., a T-cell receptor (TCR) or a chimeric antigen receptor (CAR) expressed by the cell) is specifically stimulated by an antigen and/or the cell (e.g., the calcium signaling pathway of the cell) is non-specifically stimulated by, e.g., phorbol myristate acetate (PMA)/Ionomycin.

Prokaryotic and insect inducible promoter systems have been adapted for regulated expression in mammalian cells. See, for example, Gossen et al. (1993) TIBS 18:471-475 and No et al. (1996) Proc. Natl. Acad. Sci. USA 93:3346-3351). The insect ecdysone-inducible promoter is tightly regulated with no detectable background expression in the absence of inducer. Ecdysone is suitable for use in vivo because it is a naturally occurring lipophilic steroid that can penetrate tissues, is inert in mammals and exhibits rapid clearance kinetics (No et al.). Gupta et al. (PNAS (2004) 101:1927-1932) discloses retroviral delivery of an ecdysone-inducible gene expression system under the control of a modified RNA polymerase III-specific U6 promoter.

The prokaryotic repressors from the lac and tet operons have been incorporated in eukaryotic inducible expression systems. Repression of expression is mediated by the repressor bound to operator sites placed downstream of the minimal promoter in the absence of inducer and repression is relieved on the addition of the inducer. (Brown et al., Cell (1987) 49:603-612; Hu and Davidson, Cell (1987) 48:555-566; Blau and Rossi, Proc. Natl. Acad. Sci. USA (1999) 96:797-799; and Gossen et al., Science (1995) 268:1766-1769). For example, The RheoSwitch® Mammalian Inducible Expression System (New England Biolabs) allows induction and adjustable control of gene expression in mammalian cells. The promoter is tightly regulated, giving negligible levels of basal expression in the absence of inducer and greater than 10,000 fold induction when the inducer, RSL1 ligand is present. RSL1 ligand is a synthetic compound shown to be inert within all cell lines tested. Methods for construction of expression cassettes containing an inducible promoter operatively linked to a coding sequence of any polypeptide are known to those of skill in the art, as are methods for introducing such expression cassettes and vectors containing such expression cassette into homing cells.

The expression vector can also contain a ribosome binding site for translation initiation and a transcription terminator. The expression vector can also comprise appropriate sequences for amplifying expression. The expression vector can also include nucleotide sequences encoding non-native tags (e.g., histidine tag, hemagglutinin tag, green fluorescent protein, etc.). The non-native tags can be fused to the site-directed polypeptide, thus resulting in a fusion protein.

In some embodiments, an expression vector of the disclosure can also include one or more marker genes, which allow for selection of transformed or transfected hosts. Marker genes can include biocide resistance, e.g., resistance to antibiotics, heavy metals, etc., complementation in an auxotrophic host to provide prototrophy, and the like. Suitable marker genes for an expression vectors can include, for example, neomycin/G418 resistance genes, hygromycin resistance genes, histidinol resistance genes, tetracycline resistance genes, and ampicillin resistance genes.

Further, expression vectors can in some embodiments be made to include a suicide gene. As used herein, the phrase "suicide gene" refers to a nucleotide sequence that causes a cell expressing the nucleotide sequence to die. A suicide gene can in some embodiments be a nucleotide sequence that confers sensitivity upon a cell expressing the nucleotide sequence as a transcription product and/or as a translation product to an agent (such as but not limited to a drug) such that when the cell is contacted with and/or exposed to the agent, the agent directly or indirectly causes the cell to die. Suicide genes are known in the art and include, for example, the Herpes Simplex Virus (HSV) thymidine kinase (TK) gene, cytosine daminase, purine nucleoside phosphorylase, and nitroreductase (see e.g., Springer, 2004).

Accordingly, the expression and secretion of immunomodulatory protein can be controlled to occur only when and where it is needed (e.g., in the presence of an infectious disease-causing agent, cancer, or at a tumor site), which can decrease or avoid undesired immunomodulatory protein interactions.

Vectors can be provided directly to the cells. In other words, the cells are contacted with vectors comprising the nucleic acid encoding guide RNA and/or a site-directed modifying polypeptide and/or a chimeric site-directed modifying polypeptide and/or a donor polynucleotide such that the vectors are taken up by the cells. Methods for contacting cells with nucleic acid vectors that are plasmids, including electroporation, calcium chloride transfection, microinjection, and lipofection are well known in the art. For viral vector delivery, the cells can be contacted with viral particles comprising the nucleic acid encoding a guide RNA and/or a site-directed modifying polypeptide and/or a chimeric site-directed modifying polypeptide and/or a donor polynucleotide. Retroviruses, for example, lentiviruses, are suitable to the method of the invention. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid can be packaged into viral capsids by a packaging cell line. Different packaging cell lines provide a different envelope protein (ecotropic, amphotropic or xenotropic) to be incorporated into the capsid, this envelope protein determining the specificity of the viral particle for the cells (ecotropic for murine and rat; amphotropic for most mammalian cell types including human, dog and mouse; and xenotropic for most mammalian cell types except murine cells). The appropriate packaging cell line can be used to ensure that the cells are targeted by the packaged viral particles. Methods of introducing the retroviral vectors comprising the nucleic acid encoding the reprogramming factors into packaging cell lines and of collecting the viral particles that are generated by the packaging lines are well known in the art.

C. Cell Mixtures

The cellular compositions disclosed herein can be provided as a suspension containing the first and second cell populations.

The cells produced by the methods described herein can be used immediately. Alternatively, the cells can be frozen at liquid nitrogen temperatures and stored for long periods of time, being thawed and capable of being reused. For example, the cells can be frozen in 10% dimethylsulfoxide (DMSO), 50% serum, 40% buffered medium, or some other such solution as is commonly used in the art to preserve cells at such freezing temperatures and thawed in a manner as commonly known in the art for thawing frozen cultured cells.

The cells can be cultured in vitro under various culture conditions. The cells can be expanded in culture, i.e. grown under conditions that promote their proliferation. Culture medium can be liquid or semi-solid, e.g. containing agar, methylcellulose, etc. The cell population can be suspended in an appropriate nutrient medium, such as Iscove's modified DMEM or RPMI 1640, normally supplemented with fetal calf serum (about 5-10%), L-glutamine, a thiol, particularly 2-mercaptoethanol, and antibiotics, e.g. penicillin and streptomycin. The culture can contain growth factors to which the regulatory T cells are responsive. Growth factors, as defined herein, can be molecules capable of promoting survival, growth and/or differentiation of cells, either in culture or in the intact tissue, through specific effects on a transmembrane receptor. Growth factors include polypeptides and non-polypeptide factors.

Cell mixtures of the disclosure engraft in situ and are likely respond to multicellular paracrine signaling loops existing between the cells in the local environment including, for example, parenchymal cells, endothelial cells, and stromal cells. In addition to local signals from neighboring cell types, the engineered cell mixtures of the disclosure respond to systemic regenerative signals (e.g., growth factors) following implantation in a host, such as regenerative signals due to injury, disease or infection. Signals mediating this interaction include growth factors which control cell proliferation and tissue regeneration and development.

Accordingly, in other aspects, the compositions provided herein can contain additional components, including but not limited to, growth factors, ligands, cytokines, drugs, etc. In some embodiments, the cell mixtures can include molecules which elicit additional microenvironmental cues such as small molecules or growth factors which stimulate or enhance proliferation and expansion of the first cell population.

In some embodiments, one or more soluble factors is included in the genetically engineered cell mixtures disclosed herein, for example, in drug delivery vehicle (e.g., encapsulated in a drug delivery particle, for example, a time-released delivery particle).

D. Aggregates and Implantable Grafts

In another aspect, the cellular compositions are provided in the form of an aggregate of the first and second cell populations. In some embodiments, the first and second cell populations are admixed under conditions which cause the two cell populations to form aggregates. In some embodiments, the first and second cell populations are admixed using tissue fabrication techniques. In some embodiments, the first and second cell populations are co-cultured. In some embodiments, the first and second cell populations are cocultured by hanging drop, microwell molding or non-adhesive surfaces.

The properties of the cell aggregates of the present disclosure can be varied to suit a particular application. In certain embodiments, the density of the cell aggregates can be changed. In certain embodiments, cell aggregates of different diameters can be fabricated. In certain embodiments, the overall network organization of the one or more cell aggregates can be defined, for example, by the number, three-dimensional organization, alignment, diameters, density, and the like.

In certain embodiments, the width and/or diameter of the one or more cell aggregates of the present disclosure can be greater 1 µm, 2 µm, 4 µm, 5 µm, 8 µm, 10 µm, 15 µm, 20 µm, 25 µm, 30 µm, 40 µm, 50 µm, 80 µm, 100 µm, 150 µm, 200 µm, 250 µm, 300 µm, 500 µm, 700 µm, 900 µm, 1 mm, 2 mm, 5 mm, 10 mm, or 20 mm or a combination thereof.

In certain embodiments, the number of cell aggregates contained within the cell mixture can vary. In certain embodiments, the engineered cell mixture includes at least 1, 2, 3, 4, 5, 10, 15, 20, 25, 30, 35, 50, 100, 150, 200, 300, 400, 500, 1000, 10,000, 100,000, or 1,000,000 organized cell aggregates.

In certain embodiments, the engineered cell composition can contain one or more bioactive substances. Examples of bioactive substance(s) include, but are not limited to, hormones, neurotransmitters, growth factors, hormone, neurotransmitter or growth factor receptors, interferons, interleukins, chemokines, cytokines, colony stimulating factors, chemotactic factors, extracellular matrix components, and adhesion molecules, ligands and peptides; such as growth hormone, parathyroid hormone (PTH), bone morphogenetic protein (BMP), transforming growth factor-alpha (TGF-alpha.), TGF-beta1, TGF-beta2, fibroblast growth factor (FGF), granulocyte/macrophage colony stimulating factor (GMCSF), epidermal growth factor (EGF), platelet derived growth factor (PDGF), insulin-like growth factor (IGF), scatter factor/hepatocyte growth factor (HGF), fibrin, collagen, fibronectin, vitronectin, hyaluronic acid, an RGD-containing peptide or polypeptide, an angiopoietin and vascular endothelial cell growth factor (VEGF).

In certain embodiments, the engineered cell mixtures disclosed herein include one or more adherence materials to facilitate maintenance of the desired phenotype of the grafted cells in vivo. The term "adherence material" is a material incorporated into the cell mixture disclosed herein to which a cell or microorganism has some affinity, such as a binding agent. The material can be incorporated, for example, into a hydrogel prior to implantation of the engineered cell mixture. The material and a cell or microorganism interact through any means including, for example, electrostatic or hydrophobic interactions, covalent binding or ionic attachment. The material may include, but is not limited to, antibodies, proteins, peptides, nucleic acids, peptide aptamers, nucleic acid aptamers, sugars, proteoglycans, or cellular receptors.

The type of adherence material(s) (e.g., extra-cellular matrix materials (ECM), sugars, proteoglycans etc.) will be determined, in part, by the cell type or types to be cultured. ECM molecules found in the parenchymal cell's native microenvironment are useful in maintaining the function of both primary cells, and precursor cells and/or cell lines.

i. Extracellular Matrix

In some aspects, the cell mixture contains extracellular matrix which promotes the formation of cell aggregates. In some embodiments, the extracellular matrix is a natural matrix. In some embodiments, the extracellular matrix is produced by the genetically engineered stromal cells in the second cell population. In some embodiments, the extracellular matrix comprises collagen, alginate, agarose, matrigel, silk, gelatin, hyaluronan, chitosan, fibrin, or derivatives thereof.

In some embodiments, the extracellular matrix is a synthetic matrix. In some embodiments, the synthetic matrix is polyethylene glycol (PEG) hydrogel, poly(lactic-co-glycolic acid) (PLGA), hydroxyethyl methacrylate (HEMA), peptide-based self-assembling gels, thermo-responsive poly(NIPAAm), Poly-D, L-lactide (PDLLA), Poly-e-caprolactone (PCL), hydroxyapatite or ceramic-based biomaterials.

In some embodiments, where the engineered cell mixture is used to aid vascularization, fibrin can be used as the ECM scaffold material. Other suitable ECM materials can be used as a scaffold, depending on the specific purpose for the implant and based on the properties of the ECM material, including but not limited to, the degradation properties of the ECM materials. For example, in some embodiments, the ECM scaffold can be degradable upon exposure to environmental conditions. For example, the ECM scaffold can be degraded by the presence of hydrolytic enzymes, presence of proteasomal enzymes, pH lower than 5 and reducing conditions.

In some embodiments, the naturally-derived or synthetic scaffolding used to form the cell aggregates can release bioactive substances compared to the ECM scaffold. For example, naturally-derived or synthetic scaffolding used to form cell aggregates can release pro-angiogenic factors.

ii. 3D-Scaffolds

In some aspects, the compositions comprise a three-dimensional scaffold or matrix. The term "three-dimensional matrix" or "scaffold" or "matrices" as used herein refers in the broad sense to a composition comprising a biocompatible matrix, scaffold, or the like. The three-dimensional matrix may be liquid, gel, semi-solid, or solid at 25° C. The three-dimensional matrix may be biodegradable or non-biodegradable. In some embodiments, the three-dimensional matrix is biocompatible, or bioresorbable or bioreplacable. Exemplary three-dimensional matrices include polymers and hydrogels comprising collagen, fibrin, chitosan, MATRIGEL™, polyethylene glycol, dextrans including chemically crosslinkable or photocrosslinkable dextrans, processed tissue matrix such as submucosal tissue and the like. In certain embodiments, the three-dimensional matrix comprises allogeneic components, autologous components, or both allogeneic components and autologous components. In certain embodiments, the three-dimensional matrix comprises synthetic or semi-synthetic materials. In certain embodiments, the three-dimensional matrix comprises a framework or support, such as a fibrin-derived scaffold.

In some aspects, the implantable grafts of the present disclosure can be formed by a process described herein. In certain embodiments, the method for fabricating implantable grafts containing the cell mixtures and embedding these structures in extracellular matrix includes (1) generating 3D templates that have been defined with channels or trenches, (2) suspending endothelial cells in liquid collagen and centrifuging these cells into the channels of the template, (3) removing excess cell/collagen suspension to allow cell aggregates to form, and (4) removing aggregates from templates via encapsulation in an extracellular matrix scaffold.

In some embodiments, the method for fabricating the patterned biomaterials is provided in Raghavan et al. (*Tissue Engineering Part A* (2010), Vol. 16(7): 2255-2263), the disclosure of which is incorporated herein by reference.

In some embodiments, the method for fabricating the implantable graft includes (1) suspending the first and second population of cells in a naturally-derived and/or synthetic scaffolding, (2) placing the suspended cells into the channels of a 3D template, and (3) allowing the cells to form one or more aggregates at least partially embedded in the naturally-derived and/or synthetic scaffolding. In certain embodiments, the method for fabricating the engineered implantable grafts as described herein can include the removal of the grafts from the 3D template via encapsulation in an extracellular matrix scaffold.

In other embodiments, organizing cells and material into spatial arrangements, such as cell aggregates, can be accomplished by physically constraining the placement of cells/material by the use of wells or grooves, or injecting cells into microfluidic channels or oriented void spaces/pores. In certain embodiments, the cells can be organized by physically positioning cells with electric fields, magnetic tweezers, optical tweezers, ultrasound waves, pressure waves, or micromanipulators. In certain embodiments, cells can be organized by patterning the attachment of cells into specific arrangements by seeding them onto fibers. In certain embodiments, cells can be organized by novo fabrication such as by layer-by-layer or 3D printing.

In some embodiments, the 3D templates can include naturally-derived and/or synthetic material. For example, the template can be composed of silicone or PDMS. In certain embodiments, the template can contain one or more channels. For example, the template can contain at least 1, 2, 3, 4, 5, 6, 7, 8, 9, 10, 15, 20, 30, or 40 channels. In certain embodiments, the one or more channels can be arranged in parallel formation. In certain embodiments, the one or more channels can be arranged in a non-parallel formation. In certain embodiments, the one or more channels can be organized with specific branch patterns such as rectilinear grids, bifurcated trees, in 2D or 3D organizations, with certain spacings of less than about 1 µm, greater than about 1 µm, 2, 4, 5, 8, 10, 15, 20, 25, 30, 40, 50, 80, 100, 150, 200, 250, 300, 500, 700, or 900 µm. The width of each line, groove and/or structure can be less than about 1 µm, greater than about 1 µm, 2, 4, 5, 8, 10, 15, 20, 25, 30, 40, 50, 80, 100, 150, 200, 250, 300, 500, 700, 900 µm, 1 mm, 2 mm, 5 mm, 10 mm, or 20 mm.

In some embodiments, the template can contain one or more wells and/or grooves to form one or more cell aggregates. For example, the template can contain at least 1, 2, 3, 4, 5, 6, 7, 8, 9, 10, 15, 20, 30, or 40 wells. In certain embodiments, the one or more wells can be organized with certain spacings of less than about 1 µm, greater than about 1 µm, 2, 4, 5, 8, 10, 15, 20, 25, 30, 40, 50, 80, 100, 150, 200, 250, 300, 500, 700, 900 µm, 1 mm, 2 mm, 5 mm, 10 mm, or 20 mm.

In some embodiments, the 3D template can be generated by molding, templating, photolithography, printing, deposition, sacrificial molding, stereolithography, or a combination thereof.

In some embodiments, a patterned biomaterial can be fabricated through the use a custom 3D printer technology to extrude lattices of carbohydrate glass filaments with pre-defined diameters, spacings and orientations. For example, in some embodiments, soluble (clinical-grade, sterile) fibrinogen and thrombin are combined and poured over the lattice. After the solution has polymerized into insoluble fibrin, the carbohydrate filaments are dissolved, leaving behind channels within the fibrin. The channels can then be filled with a suspension of cells in a naturally-derived or synthetic scaffolding (e.g., soluble type I collagen) that subsequently is polymerized to trap the cells within the channels.

iii. Encapsulation

Biopolymers suitable for use include any polymer that is gellable in situ, i.e., one that does not require chemicals or conditions (e.g., temperature, pH) that are not cytocompatible. In certain embodiments, polymers are synthetic or natural biopolymers (i.e., are biocompatible.) This includes both stable and biodegradable biopolymers. Biodegradable polymers are useful, for example, where proliferation of one or more populations of the encapsulated cells is desired. Polymers that can be used in the methods and constructs described herein include, but are not limited to, PEG hydrogels, poly(lactic-co-glycolic acid) (PLGA), hydroxyethyl methacrylate (HEMA), gelatin, fibrin, matrigel, alginate, agarose, polysaccharides, collagen, hyaluronic acid (HA), peptide-based self-assembling gels, thermo-responsive poly (NIPAAm). A number of biopolymers are known to those skilled in the art (Bryant and Anseth, J. Biomed. Mater. Res. (2002) 59(1):63-72; Mann et al., Biomaterials (2001) 22 (22): 3045-3051; Mann et al., Biomaterials (2001) 22 (5): 439-444, and Peppas et al., Eur. J. Pharm. Biopharm. (2000) 50(1), 27-46; all incorporated by reference).

Polymers for use herein are preferably crosslinked, for example, ionically crosslinked. In certain embodiments, the methods and constructs described herein use polymers in which polymerization can be promoted photochemically (i.e., photo crosslinked), by exposure to an appropriate wavelength of light (i.e., photopolymerizable) or a polymer which is weakened or rendered soluble by light exposure or other stimulus. Although some of the polymers listed above are not inherently light sensitive (e.g. collagen, HA), they may be made light sensitive by the addition of acrylate or other photosensitive groups.

In certain embodiments, the method utilizes a photoinitiator. A photoinitiator is a molecule that is capable of promoting polymerization of hydrogels upon exposure to an appropriate wavelength of light as defined by the reactive groups on the molecule. In the context of the disclosure, photoinitiators are cytocompatible. A number of photoinitiators are known that can be used with different wavelengths of light. For example, 2,2-dimethoxy-2-phenyl-acetophenone, HPK 1-hydroxycyclohexyl-phenyl ketone and Irgacure 2959 (hydroxyl-1-[4-(hydroxyethoxy)phenyl]-2methyl-1propanone) are all activated with UV light (365 nm). Other crosslinking agents activated by wavelengths of light that are cytocompatible (e.g. blue light) can also be used with the methods described herein.

In other embodiments, the method involves the use of polymers bearing non-photochemically polymerizable moieties. In certain embodiments, the non-photochemically polymerizable moieties are Michael acceptors. Non-limiting examples of such Michael acceptor moieties include α,β-unsaturated ketones, esters, amides, sulfones, sulfoxides, phosphonates. Additional non-limiting examples of Michael acceptors include quinines and vinyl pyridines. In some embodiments, the polymerization of Michael acceptors is promoted by a nucleophile. Suitable nucleophiles include, but are not limited to thiols, amines, alcohols and molecules possessing thiol, amine and alcohol moieties. In certain embodiments, the disclosure features use of thermally crosslinked polymers.

In certain embodiments, patterned cells suitable for the constructs and methods described herein are localized in specked locations that may occur in repeating structures within 3-dimensional biopolymer rather than being randomly localized throughout 3-dimensional slab of biopolymer, on the surface of a regularly or irregularly shaped 3-dimensional scaffold or patterned on a 2-dimensional support (e.g. on a glass slide). The cells can be patterned by locating the cells within specific regions of relatively homogeneous slabs of biopolymers (resolution up to about 5 microns) or by creating patterned biopolymer scaffolds of defined patterns wherein the living cells are contained within the hydrogel (resolution up to about 100 microns). Patterning is performed without direct, mechanical manipulation or physical contact and without relying on active cellular processes such as adhesion of the cells.

Relatively homogeneous slab of biopolymer refers to a polymerized biopolymer scaffold that is approximately the same thickness throughout and is essentially the same shape of the casting or DEP chamber in which it was polymerized.

Patterned biopolymer scaffold refers to a biopolymer scaffold that is of a substantially different shape than the casting or DEP chamber in which it was polymerized. The pattern could be in the form of shapes (e.g. circles, stars, triangles) or a mesh or other form. In some embodiments, the biopolymer is patterned to mimic in vivo tissue architecture, such as branching structures.

The methods for use herein can be used for the production of any of a number of patterns in single or multiple layers including geometric shapes or a repeating series of dots with the features in various sizes. Alternatively, multilayer biopolymer gels can be generated using a single mask turned in various orientations. The formation of high-resolution patterned cells in 3-dimensions can be achieved by methods other than photopolymerization, such that the limitations of the method are overcome.

Stereolithography via photopatterning may be used to introduce perfusion channels, thus significantly improving diffusive transport of oxygen and nutrients to photo-encapsulated hepatocytes. In some embodiments, the perfusion channel consists of a single-layer hexagonal branching pattern.

Cells may be patterned within the hydrogel by selective polymerization of the biopolymer or by patterning of the cells using an electrical field or both. Theoretically a single cell can be patterned by locating it in a specific position within a biopolymer; however, in some embodiments a plurality of cells, at least 10, at least 20, at least 100, at least 500 cells, are patterned. Patterning does not require localization of all cells to a single, discrete location within the biopolymer. Cells can be localized, in lines one or two or many cells wide, or in multiple small clusters throughout a relatively homogeneous biopolymer scaffold (e.g. approximately 20,000 clusters of 10 cells each in a single scaffold). The 3-dimensional patterning can also include patterning of cells or other particles in a single plane by DEP as the cells are contained in a three-dimensional scaffold. The cell patterning methods described herein, can also be used for patterning of organelles, liposomes, beads and other particles.

Cell organization can be controlled by photopatterning of the hydrogel structure. The photopolymerizable nature of acrylate-based PEG hydrogels enables the adaptation of photolithographic techniques to generate patterned hydrogel networks. In this process, patterned masks printed on transparencies act to localize the UV exposure of the prepolymer solution, and thus, dictate the structure of the resultant hydrogel.

In certain embodiments, hepatocellular hydrogel constructs with defined cellular configurations may be prepared by photopatterning PEG hydrogels containing the first and second cell populations, resulting in a hydrogel network consisting of 3D cell 'aggregates'. Further control of cell orientation within these patterned domains may be achieved utilizing dielectrophoretic patterning techniques. Dielectrophoresis (DEP) can be used alone for patterning of cells in relatively homogeneous slabs of hydrogel or in conjunction with the photopolymerization method. The methods allow for the formation of three-dimensional scaffolds from hundreds of microns to tens of centimeters in length and width, and tens of microns to hundreds of microns in height. A resolution of up to 100 microns in the photopolymerization method and possible single cell resolution (10 micron) in the DEP method is achievable. Photopolymerization apparatus, DEP apparatus, and other methods to produce 3-dimensional co-cultures are described in U.S. Pat. No. 8,906,684, which is incorporated herein by reference.

In other embodiments, the biopolymers may additionally contain any of a number of growth factors, adhesion molecules, degradation sites or bioactive agents to enhance cell viability or for any of a number of other reasons. Such molecules are well known to those skilled in the art.

In certain embodiments, cells are encapsulated at a concentration or density of about $0.1 \times 10^6$/ml to about $100 \times 10^6$/ml, or about $0.1 \times 10^6$/ml to about $20 \times 10^6$/ml, about $0.5 \times 10^6$/ml, 1, 2, 5, 10 or $15 \times 10^6$/ml. In certain embodiments, genetically engineered non-parenchymal are encapsulated at a ratio (as compared to the cells of the first population) of about 0.1:1, 0.5:1, 1:1, 1.5:1, 2:1, 3:1, 5:1 or 10:1. In some embodiments, the above values or ranges are at the time of encapsulation. In some embodiments, the above values or ranges are at a time following encapsulation or implantation, e.g., at about 1, 2, 5, 12, 24, 36, 48, 72, 96 or more hours after encapsulation or implantation, i.e., the unmodified cells, e.g., the parenchymal cells and/or one or more genetically engineered non-parenchymal cell populations are encapsulated at a lower concentration or density and proliferate to achieve the indicated concentration or density after a certain time in culture or in vivo.

III. Characterization

Where appropriate, in vivo immunosuppression or tolerance to a transplanted cell or tissue may be measured using in vitro assays, such as, for example, in a mixed lymphocyte reaction using cells isolated from a subject. Similarly, tolerance and/or immunosuppression achieved in cells ex vivo may also be measured in ex vivo assays using various types of cells, such as, for example, dendritic cells, T cells, or B cells. If tolerization or tolerance and/or immunosuppression is measured using an ex vivo method, tolerization or tolerance is considered to have occurred if the response of the cells to an immune stimulus is decreased by at least 10%, 20%, 30%, 40%, 50%, 70%, 90% or more in comparison to an appropriate control. Suitable assays directly or indirectly measure immune response and are known in the art; they include, but are not limited to: mixed lymphocyte reaction assays; cytotoxicity assays; antibody titer assays; assays for the production of IL-4 and/or IL-10; assays for the production of TGF-beta.; evaluation of cell surface markers; and assays for the expression of Foxp3.

In Vitro Assays

The level of a specified protein refers to the amount of protein in a cell sample as determined using any method known in the art for measuring protein levels, including electrophoresis, capillary electrophoresis, high performance liquid chromatography (HPLC), thin layer chromatography (TLC), hyperdiffusion chromatography, fluid or gel precipitation reactions, absorption spectroscopy, colorimetric assays, spectrophotmetric assays, flow cytometry, immmunodiffusion, solution phase assay, immunoelectrophoresis, Western blotting, radioimmunoassay (RIA), enzyme-linked immunosorbent assays (ELISAs), immunofluorescent assays and electrochemiluminescence immunoassays.

In Vivo Assays

In some aspects, the cellular compositions or graft is implanted into a subject and expands into a functional engineered issue. Expansion of the engineered tissue can be evaluated by measuring biomarkers. For example, the engineered cellular composition or graft is implanted into a subject and exposed to regeneration cues expresses and/or induces human drug-metabolizing enzymes and other key tissue-specific genes (e.g., transcription factors) when compared to unexpanded cell populations (e.g., endothelial and fibroblast cells).

In some embodiments, the expanded engineered tissue sample contains hepatocytes which are exposed to regeneration cues express Phase I cytochrome P450 enzymes. In some embodiments, the expanded engineered tissue sample is exposed to regeneration cues express CYP3A4 and/or CYP2B6. In some embodiments, the expanded engineered tissue sample exposed to regeneration cues express Phase II enzymes. In some embodiments, the expanded engineered tissue sample is exposed to regeneration cues express sulfotransferase. In some embodiments, the expanded engineered tissue sample exposed to regeneration cues express Phase III anion transporters. In some embodiments, the expanded engineered tissue sample is exposed to regeneration cues express SLCO1A2/1B1. In some embodiments, the expanded engineered tissue sample is exposed to regeneration cues express ATP-binding transporters. In some embodiments, the expanded engineered tissue sample exposed to regeneration cues express ABCB/ABCG.

In some embodiments, the engineered tissue sample implanted in a subject contain red blood cells. In some embodiments, regeneration cues promote expansion of the blood pool in engineered tissue sample implanted in a subject. In some embodiments, regeneration cues promote the formation of vessels in an engineered cellular composition or graft tissue implanted in a subject. In some embodiments, the vessels in an engineered tissue sample contain Ter-119 positive erythroid cells and human CD31-positive endothelial cells.

IV. Use

The compositions and implantable grafts described herein can be used in a number of in vitro, ex vivo, and in vivo applications, and are particularly suited for implantation in a host, for example a human or non-human, animal host.

One aspect of the present invention provides cells that have been engineered such that, once transplanted into a host, they do not trigger an immune response in the host (they suppress an immune response in the host). Another aspect of the present invention provides methods of directly introducing these cells into a host to stimulate regeneration and repair of various tissues.

In some aspects, the compositions and grafts described herein can be used to enhance the survival, function, and expansion of the cells upon implantation. Effective mass transport between the blood stream and the tissue for metabolic needs relies on a precisely-defined microenvironment delineated by the paracrine signaling between hepatocytes and endothelial cells.

In some aspects, the disclosure provides a method of inhibiting immune rejection of graft in a subject by administering to a subject in need thereof a cellular composition or implantable grafts as described herein. In some embodiments, the composition or graft comprises cardiac cells, skin cells, kidney cells, pancreatic cells, liver cells, lung cells or cells from an endocrine organ. In some embodiments, the composition comprises allogeneic cells. In other embodiments, the composition comprises xenogeneic cells.

In some embodiments, the subject is a recipient of a hematopoietic cell or bone marrow transplant, an allogeneic transplant of pancreatic islet cells, or a solid organ transplant selected from the group consisting of heart, skin, liver, lung, heart and lung, kidney, pancreas, or an endocrine organ (e.g., a thyroid gland, parathyroid gland, a thymus, adrenal cortex, or adrenal medulla).

In other aspects, the disclosure provides a method of reducing immune activation in a subject in need thereof, by administering a cellular composition or implantable grafts disclosed described herein. In some embodiments, the method reduces, inhibits or prevents fibrosis.

In other aspects, the disclosure provides a method of promoting immune tolerance in a subject in need thereof, by administering a cellular composition or implantable grafts disclosed described herein. In some embodiments, the method reduces, inhibits or suppresses an immune response to homogeneic molecule, e.g., an autoimmune response.

In another aspect, the disclosure provides methods of promoting immune tolerance, for example, in response to transplantation of cells, tissues or organs into a subject, by administering the compositions or implantable grafts provided herein.

In some aspect, the disclosure provides compositions and implantable grafts for use in inhibition of immune rejection by administering the compositions or implantable grafts provided herein.

In some aspect, the disclosure provides compositions and implantable grafts for use in inhibition of immune activation by administering the compositions or implantable grafts provided herein.

In some aspect, the disclosure provides compositions and implantable grafts for use in promoting tolerance by administering the compositions or implantable grafts provided herein.

The cells used in the methods and compositions described herein may transiently express the immunomodulatory polypeptide (e.g., an immunosuppressive polypeptide) prior to the time of administration, at the time of administration and/or after administration. For example, in embodiments where expression of the immunomodulatory polypeptide is under the control of an inducible promoter, expression of the immunomodulatory polypeptide could be induced in vitro prior to administration and/or in vivo after administration. If expression is induced in vitro prior to administration, transient expression could be either complete or on-going at the time of administration. In cases where transient expression (i.e., de novo translation) of the immunomodulatory polypeptide (e.g., an immunosuppressive polypeptide) is complete at the time of administration, the polypeptide should be stable enough to persist for at least 2, 4, 6, 8, 12, 18, 24 or more hours after administration. Alternatively, or in addition, transient expression can be induced one or more times after administration. Preferably, the cells transiently express (e.g., translated de novo protein) and/or contain the immunomodulatory polypeptide (e.g., immunosuppressive polypeptide) of interest at the time they arrive at a secondary lymphatic tissue at or in the proximate vicinity of an undesired immune response.

In other aspects of the disclosure, regeneration and growth of the first cell population in situ is monitored in the host by detecting the presence of a regenerative factor (or biomarker) expressed by the first cell population, such as a growth factor (e.g., hepatocyte growth factor (HGF)), in a sample (such as a blood sample) from the host. Such biomarkers include, for example, serum albumin, alpha-1 antitrypsin, transferrin, clotting factors, and drug metabolism.

A therapeutically significant reduction in a symptom is, e.g. at least about 10%, at least about 20%, at least about 30%, at least about 40%, at least about 50%, at least about 60%, at least about 70%, at least about 80%, at least about 90%, at least about 100%, at least about 125%, at least about 150% or more in a measured parameter as compared to a control or non-treated subject. Measured or measurable parameters include clinically detectable markers of disease, for example, elevated or depressed levels of a biological marker, as well as parameters related to a clinically accepted scale of symptoms or markers for a disease or disorder. It will be understood, that the total daily usage of the compositions and formulations as disclosed herein will be decided by the attending physician within the scope of sound medical judgment. The exact amount required will vary depending on factors such as the type of disease being treated.

V. Administration

In some aspects, the engineered cellular compositions and implantable grafts described herein can be implanted in a subject. Non-limiting examples of non-human subjects include non-human primates, dogs, cats, mice, rats, guinea pigs, rabbits, fowl, pigs, horses, cows, goats, sheep, etc. In certain embodiments, the subject can be any animal. In certain embodiments, the subject can be any mammal. In certain embodiments, the subject can be a human The composition can be administered in any suitable manner, often with pharmaceutically acceptable carriers. In some aspects, the compositions can be administered subcutaneously, intramuscularly, intravenously, intravascularly, intraportally, intrasplenically or intraperitoneally. In some embodiments, the composition or graft is implanted at the site of a tissue or organ. In some embodiments, the composition or graft is administered at an orthotopic site. In other embodiments, the composition or graft is administered an ectopic site.

In another aspect, cell compositions or genetically engineered vectors expressing an immunomodulatory protein are administered ex vivo, for example, to perfuse a whole organ from an allogeneic donor prior to transplantation.

Autologous, allogenic or xenogenic cells may be used. The cells may be administered in any physiologically acceptable medium. In one embodiment, the cells are cryopreserved in 5-20% DMSO, 5% dextrose and autologous serum. As is familiar to those of skill in the art, dosage of the cells of the present invention to be administered in vivo is determined with reference to various parameters, including the species of the host, the age, weight and disease status. Dosage also depends upon the location to be targeted within the host, e.g. the site of transplantation of tissue from a donor. For example, direct targeting to the site of inserted tissue may require different dosages than administration into the blood stream of a mammalian host. The dosage is preferably chosen so that administration causes an effective result, which can be measured by molecular assays or by monitoring a suitable symptom in the subject.

Alleviation of disease or unwanted immune responses includes instances where expression of immunomodulatory polypeptides by the cells stabilize or improve the clinical symptoms of the patient. A symptom of a disease or disorder is considered to be reduced if an undesired symptom is decreased, or improved, as appropriate, by at least 10%, 20%, 30%, 40%, 50%, 70%, 90% or more in comparison to an appropriate control, such as in comparison to the symptom prior to treatment or in comparison to the expected severity of the symptom, where the treatment is intended to be preventive. One of skill is familiar with techniques and criteria for evaluating changes in symptoms. Symptoms of diseases or disorders caused by the dysfunction or undesired function of an immune response are known to those in the art and include the following: abnormal histology of a transplanted tissue; abnormal function of a transplanted tissue; brief length of survival time following an event such as, for example, diagnosis or transplantation; abnormally or undesirably high or low level or number of indicator protein(s) or other compound(s) in the blood, such as undesired antibodies or undesired cells (e.g., antigen-specific T cells); abnormally or undesirably high or low level or number of indicator cells in the blood or elsewhere in the body, e.g., an undesirably low level or number of regulatory T cells, so that an undesired immune response is initiated or maintained.

In some embodiments, the method further comprises administering an immunosuppressive or immunomodulatory drug. In some embodiments, the immune response is a humoral response or antibody-mediated response. In some embodiments, the method prevents graft rejection or promotes graft survival.

The cell mixtures, cell aggregates and implantable grafts disclosed herein can be administered in combination with one or more additional immunosuppressive therapies including, but not limited to drugs which inhibit T-cell activation (e.g., calcineurin (CaN) inhibitors), systemic immunosuppressants for universal transplant immunotolerance (corticosteroids such as methylprednisolone (Medrol), prednisone or prednisolone), CNI such as tacrolimus (Prograf, Astafraf), cyclosporine (Neoral, Sandimmune, Gengraf), anti-metabolites such as Mycophenolate motefil (Cellcept, Myfortic), Azathioprine (Imuran), mTORI such as Sirolimus (Rapamune), Everolimus (Afinitor), T-cell depleting monoclonal antibodies such as muromonab-CD3 (OKT3), Alemtuzumab (Campath-1H), ATG (Thymoblobulin, ATGAM), IL-2-Ra monoclonal antibodies such as daclizumab (Zenapax), Basiliximab (Simulect), N-Acetyl Cysteine (NAC), Heplisav-B, Mavyret, Vosevi, Ocaliva, Zepatier, Cholbam, Daklinza, Technivie, Olysio, Sovaldi, Incivek, Victrelis, Viread, Tyzeka, Baraclude, Hepsera, Pegasys, Peg-intron, Ribavarin and Twinrix. Additional agents include glitazones and vitamin E.

EXAMPLES

Example 1—Genetic Engineering of Support Cell Populations

In this example, support cell populations (dermal fibroblasts and umbilical vein endothelial cells) of human origin were genetically engineered using lentiviral vectors to over-express immune checkpoint proteins such as PD-L1, CD47, CD39/73 and then co-encapsulated with primary human hepatocytes (PHHs). When co-encapsulated with parenchymal cells the engineered supporting cell population provided inhibitory signals to nearby immune cells, thus protecting the co-encapsulated cells from T cell cytotoxicity.

Inhibitors of various immune effectors were selected and are presented in Table 1. While there are innumerable mix-and-match possibilities, four factors were selected which hit crucial points in the rejection process: PD-L1, CD47, and CD39/73. These four molecules can function in concert to inhibit the innate immune response, antigen presentation by dendritic cells, the adaptive immune response, and any residual immune activity. CD47 can inhibit macrophage and NK cell activity (Ide et al., PNAS (2007) 104(12):5062-5066; Legrand et al. PNAS (2011) 108: 13224-13229) and downregulate dendritic cell activation (Demeure, C E., et al., J. Immunol. (2000) 164(4):2193-2199). PD-L1 is a potent T cell suppressant (Kier, M E, et al., J. Exp. Med. (2006):26(1):104-111; Iwai et al., PNAS (2002) 99(19):12293-12297). CD39 and CD73 also were selected to inhibit any residual T cell-mediated cytotoxicity that will lead to an increase in extracellular ATP concentration resulting from cellular lysis. Hydrolysis of extracellular ATP by membrane-bound ectonucleotidases (CD39 and CD73) generates immunosuppressive adenosine, thus acting as a negative-feedback mechanism to prevent excessive inflammation and graft damage (Deaglio et al., J. Exp. Med. (2007) 204(6):1257-1265).

TABLE 1

Panel of inhibitory molecules that can downregulate the alloimmune response at various points in the rejection process.

| Antigen Presentation | Plasma Cell Differentiation | T Cell Inhibition |
|---|---|---|
| Cathepsin S peptide inhibitors | IL-24 | PD-L1 |
| gp48 | | PD-L2 |
| gp34 | Macrophage Inhibition | CD200 |
| IL-35 | | B7-H3 |
| | CD47 | B7-H4 |
| T helper Polarization | | B7-H7 |
| | NK Cell Inhibition | HVEM |
| TGFβ | | CEACAM1 |
| IL-10 | HLA-E | CD155 |
| PGE2 | HLA-G | CD39/73 |
| | | Stabilin-1 |
| | | IL-1ra |
| | | Gal-9 |
| | | IDO |

Materials and Methods

Fibroblast Culture

Neonatal Human Dermal Fibroblasts (HDFs, Lonza) were purchased commercially. HDFs were cultured at 37° C., 5% CO2 in Dulbeccos Modified Eagles Medium (DMEM, Corning Life Sciences) with high glucose, 10% (v/v) fetal bovine serum (Gemini Bio-Products), and 1% (v/v) penicillin-streptomycin (Corning Life Sciences). During maintenance, fibroblasts were passaged at 80% confluency and kept below passage 6 for all experiments.

Endothelial Cell Culture

Pooled Human Umbilical Vein Endothelial Cells (HUVECs, Lonza) were purchased commercially. Cells were cultured at 37° C., 5% CO2 in EGM-2 media (Lonza). During maintenance, HUVECs were passaged at 80% confluency and kept below passage 5 for all experiments.

Transgenic Overexpression of Inhibitory Molecules

Lentiviral particles for the gene of interest were purchased from G&P Bio. Cells were transduced with lentiviral particles (estimated MOI=5) when they were 40% confluent and in media containing 8 µg/mL Hexadimethrine bromide (Polybrene, Sigma Aldrich). After 48 hours of transduction, wells were refreshed with normal media. 24 hours after the media change, puromycin (Sigma Aldrich) at a concentration of 2 µg/mL or blasticidin (Santa Cruz Biotech) at a concentration of 1 µg/mL was added to the wells. The cells were passaged twice in antibiotic-supplemented media and cryopreserved before further use.

Transcriptional Profiling

Cells in wells were lysed and homogenized in TRIzol (Thermo Fisher Scientific) after media removal. Total RNA was isolated via chloroform extraction and purified using the NucleoSpin RNA kit (Takara Bio). cDNA synthesis was performed using the $RT^2$ first strand synthesis kit (Qiagen) and quantitative PCR was carried out using a $RT^2$ profiler PCR array for human T-cell and B-cell activation (Qiagen) in a BioRad CFX96 Real-Time System according to the manufacturer's instructions. Relative mRNA quantification was calculated with the ΔΔCt method, using on-plate housekeeping genes.

In Vitro Microfluidic Vessel Construction

One-channel microfluidic devices were fabricated and assembled using photo- and soft-lithography as previously described (Polacheck, W J, et al. Nature (2017) 552:258-262; Polacheck, W J, et al., Nature Protocols (2010) 107: 3141-3145). After being plasma-treated for 30 seconds at 100 W, the assembled devices were surface-functionalized with 0.01% poly-L-lysine (Sigma Aldrich) and 1% glutaraldehyde (Sigma Aldrich) at room temperature for 5 minutes each to promote the binding of extracellular matrix (ECM) to the device surface. The devices were then washed in water overnight at room temperature. On the day of cell seeding, each device was washed in 70% ethanol and inserted with a steel acupuncture needle (300 µm diameter, Hwato) followed by 15-minute UV-sterilization. A solution of 2.5 mg/ml bovine fibrinogen (Sigma Aldrich), 1 U/ml bovine thrombin (Sigma Aldrich), and DPBS was added into the ECM chambers of the devices and was allowed to crosslink at room temperature for 10 minutes before media addition. Needles were removed from the devices to form hollow microfluidic channels surrounded in fibrin. A suspension of human umbilical vein endothelial cells (HUVECs, Lonza) was added at 0.5 million cells/ml to the reservoirs connecting the microfluidic channels, and the cells were allowed to adhere to the top and bottom surfaces of the channels for 5 minutes each at 37° C. Devices were then rinsed with fresh media to remove non-adherent cells and maintained at 37° C. on either a tilting rocker (5 rpm) for flow conditions or a flat surface for static conditions. All T cell experiments were conducted in EGM-2 media (Lonza) without hydrocortisone.

3D PHH-Fibroblast Aggregation 24-well polystyrene plates containing pyramidal inserts were passivated using 5% Pluronic (Sigma Aldrich) for 30 minutes. Afterwards, each well was rinsed three times with 500 µL DMEM containing 1% (v/v) penicillin-streptomycin per well. Modified ITS media was prepared from DMEM with L-glutamine supplemented with 1% (v/v) ITS Universal Culture Supplement (Corning Life Sciences), 1% (v/v) penicillin/streptomycin, 10% (v/v) fetal bovine serum, 15.4 mM HEPES (Thermo Fisher Scientific) and 70 ng/mL glucagon (Sigma Aldrich). Even though dexamethasone is part of the usual ITS media cocktail, it was left out as it can suppress T cell activity. Cryopreserved PHHs were thawed, spun down at 60×g for 6 mins in DMEM and resuspended in ITS media. 120,000 PHHs were added to each well of the 24-well polystyrene plate containing pyramidal inserts in 500 µL of modified ITS media. The plate was then spun at 60×g for 6 minutes and incubated at 37° C., 5% CO2 for 24 hours to allow the cells to clump. Next day, the plate was spun down again at 60×g for 6 mins and the media above the PHH clumps was removed. Human dermal fibroblasts (HDFs) were dissociated using TrypLE Express (Thermo Fisher). HDFs were spun down at 1000 rpm for 5 minutes and resuspended in modified ITS media. 360,000 HDFs were then added to each well of the 24-well polystyrene plate containing 120,000 PHHs per well. The plate was then spun at 60×g for 6 mins and incubated at 37° C., 5% CO2 for 24 hours to allow the HDFs to form a barrier around the PHHs.

Immunofluorescence

Microfluidic devices were fixed with 4% paraformaldehyde (PFA, Electron Microscopy Sciences) in PBS for 15 minutes at 37° C. on the rocker. The devices were then washed 3× with PBS and permeabilized with 0.25% Triton X-100 (Sigma Aldrich) for 15 minutes. After another 3× washes with PBS, the cells were blocked with 3% bovine serum albumin (BSA, Sigma Aldrich) in PBS at 4° C. overnight. Primary antibodies were diluted in the blocking solution and incubated in the devices at 4° C. overnight with rocking. The devices were then washed in PBS at 4° C. overnight. Secondary antibodies and Hoechst (Thermo Fisher Scientific) were diluted in the blocking solution and incubated in the devices at 4° C. overnight with rocking, followed by a PBS wash at 4° C. overnight. The stained devices were stored in PBS at 4° C. until imaging. For immunofluorescence imaging, the devices were place on a Yokogawa CSU-21/Zeiss Ax-iovert 200M inverted spinning disk microscope with a 10× air objective or 25× water-immersion objective and an Evolve EMCCD camera (Photometrics). Fluorescence images were adjusted for brightness/contrast and merged using ImageJ (NIH).

Antibodies

Primary antibodies were purchased from the following sources and utilized at the following dilutions: VE-Cadherin (F-8, Santa Cruz Biotechnology, 1:200), Arginase-1 (Sigma Aldrich, 1:400), acetylated a tubulin (Santa Cruz Biotechnology, 1:100), HNF4 α (Santa Cruz Biotechnology, 1:400). Dylight 649 conjugated Ulex Europaeus Agglutinin I lectin (1:200) was purchased from Vector Laboratories. For secondary antibodies, Alexa Fluor 488, 568, 594 and 647 anti-mouse, anti-goat and anti-rabbit IgG secondary antibodies were purchased from Life Technologies.

Gene Expression

Cells in devices were lysed and homogenized in TRIzol (Thermo Fisher Scientific) after media removal. Total RNA was isolated via chloroform extraction and purified using the RNeasy MinElute Cleanup Kit (QIAGEN). cDNA synthesis was performed using the iScript cDNA synthesis kit (Bio-Rad) and quantitative PCR was carried out using the Taqman gene expression assay system (Thermo Fisher Scientific) in a BioRad CFX96 Real-Time System according to the manufacturer's instructions. The FAM-labeled Taqman probes (Thermo Fisher Scientific) used were as follows: KLF2 (Hs00360439 g1), NOS3 (Hs01574659 m1) and COX-2 (Hs00153133 ml). Relative mRNA quantification was calculated with the ΔΔCt method, using a GAPDH probe as housekeeping gene.

Results

Protector Cells Generated Using Lentiviral-Mediated Gene Transfer

For the protector cell population, cells that support function of human hepatocytes were identified, and human dermal fibroblasts (HDFs) and human umbilical vein endothelial cells (HUVECs) were selected. In prior studies, both HUVECs and HDFs have demonstrably improved human hepatocyte functions in vitro (Stevens, K R, et al, Sci. Transl. Med. (2017) 9(399): eaah5505) and in vivo (Stevens, K R, et al., Nat. Comm. (2013) 4:1847).

The identified cell populations were then engineered to overexpress the selected immune checkpoint molecules through the use of lentiviral vectors. Specifically, the surface of these cells exhibit molecules that selectively inhibit the innate immune system and antigen presentation (CD47), the adaptive immune system (PD-L1) and molecules that act as a feedback loop to abrogate any residual immune cell activity (CD39/CD73). This process was accomplished by the use of expression vectors, e.g., lentiviral vectors, as depicted in FIG. 1A. FIG. 1B shows overexpression of PD-L1, CD47 and CD39/73 in NHDFs, and overexpression of PD-L1 in HUVECs.

Figure 2B:
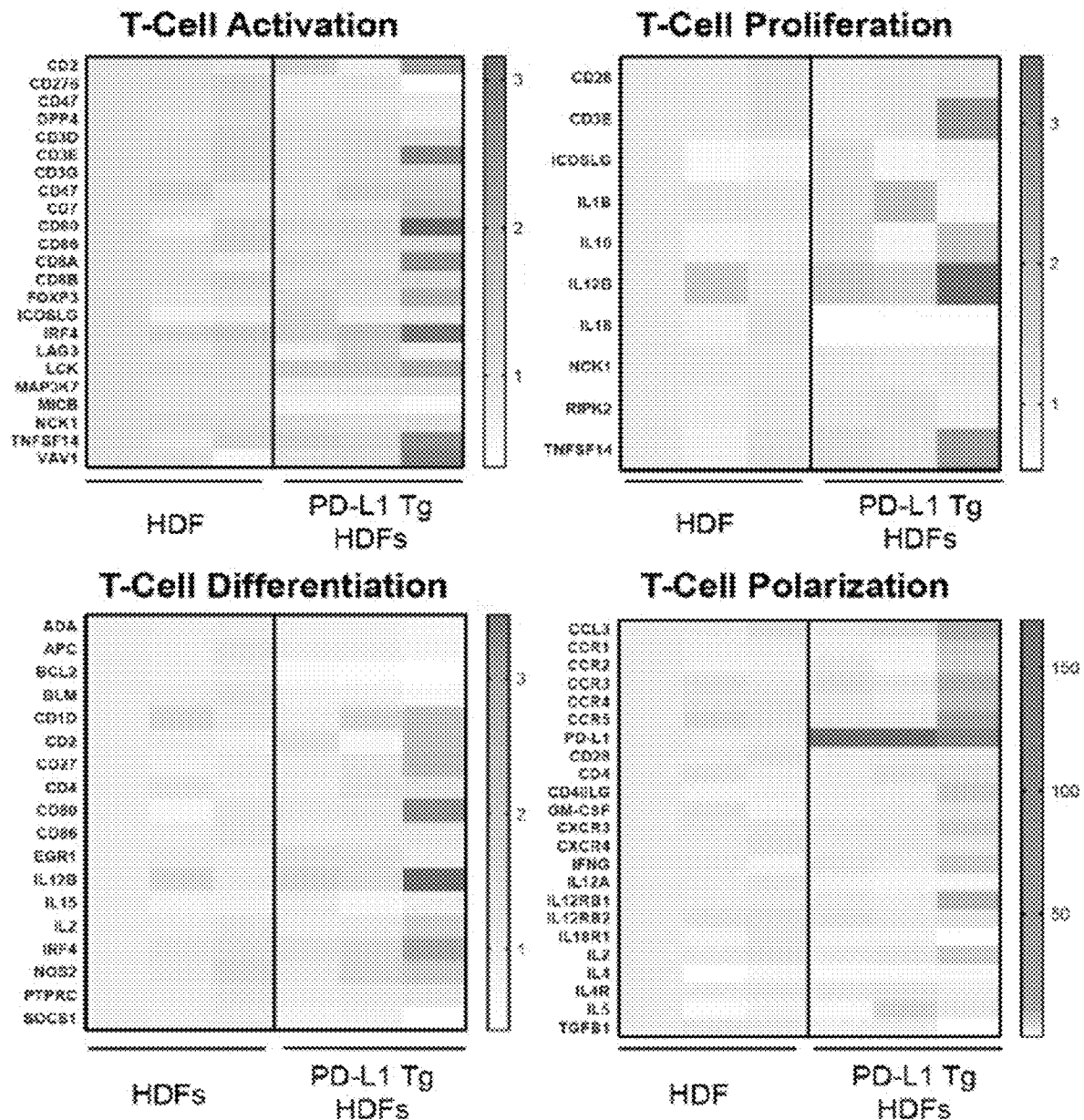
FIG. 2B depicts heatmaps of genes relevant to T cell activation, proliferation, polarization and differentiation. Each column is an independent cell line.

The HDFs transduced with Lenti-PDL1 were transcriptionally confirmed to have increased expression of PD-L1 and not of other immune markers (FIGS. 2A-2B).

Protector Stromal Cells Inhibited T Cell Activity

Figure 3A:
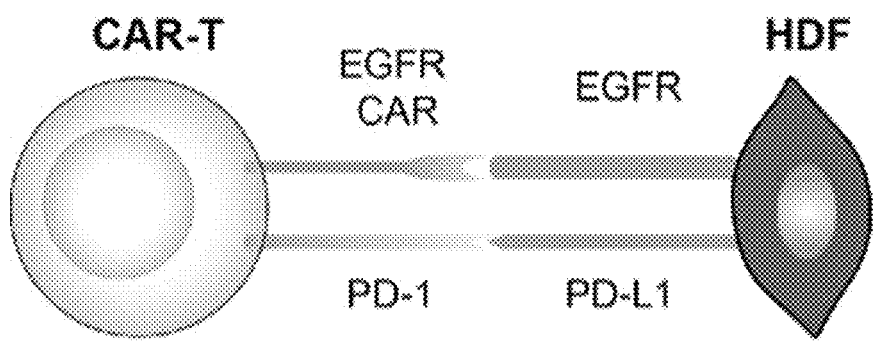
FIGS. 3A-3H show that PD-L1 upregulation on HDFs provides partial protection against CAR-T mediated cytotoxicity.
Figure 3B:
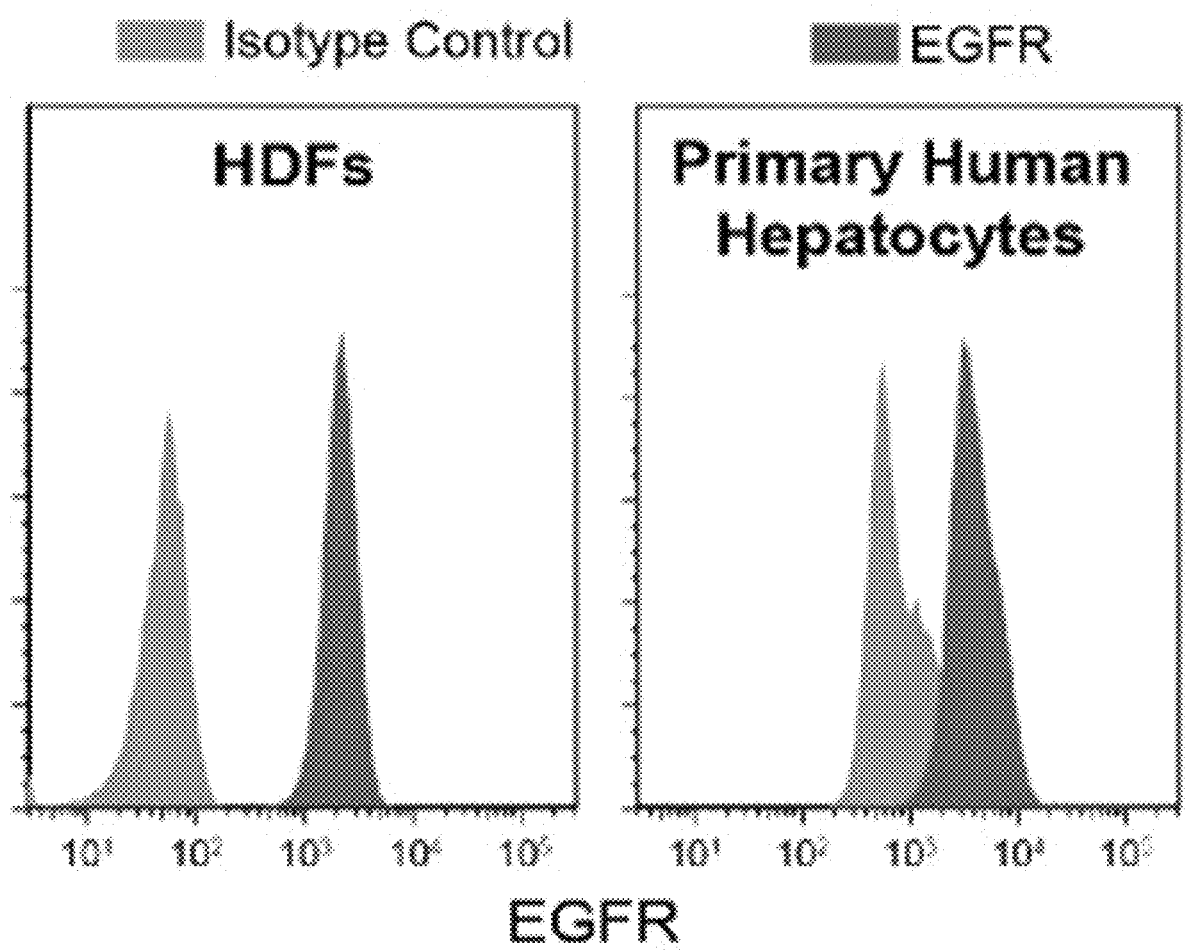
Figure 3C:
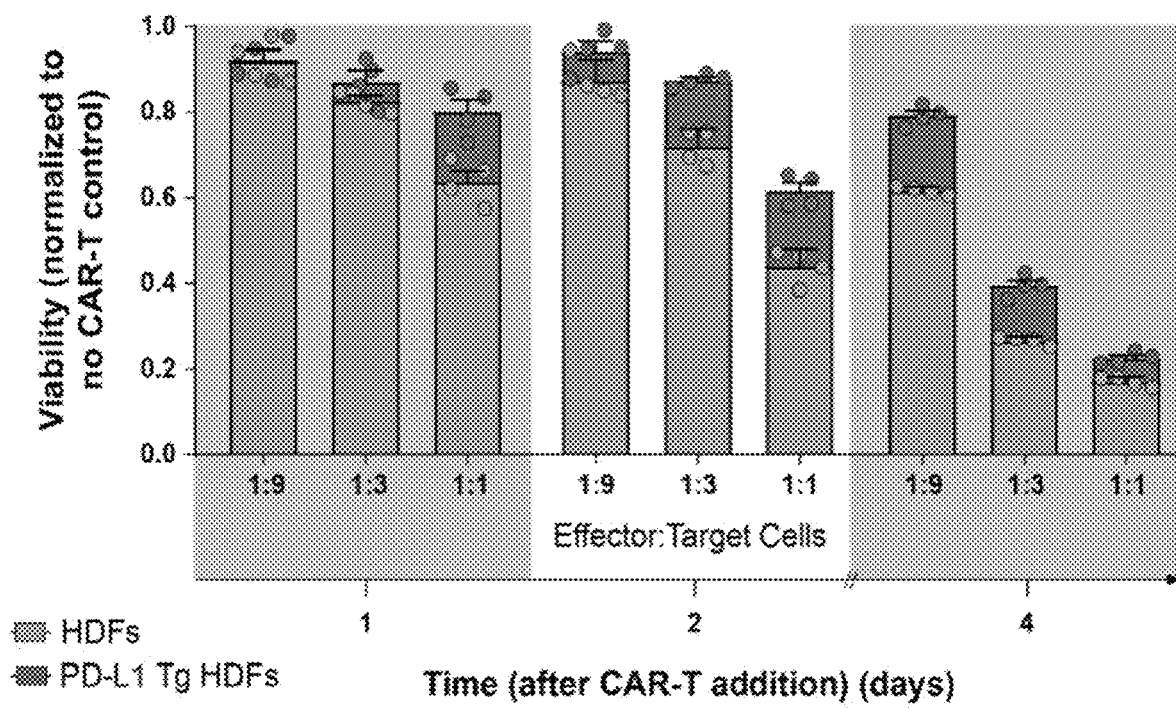
Figure 3D:
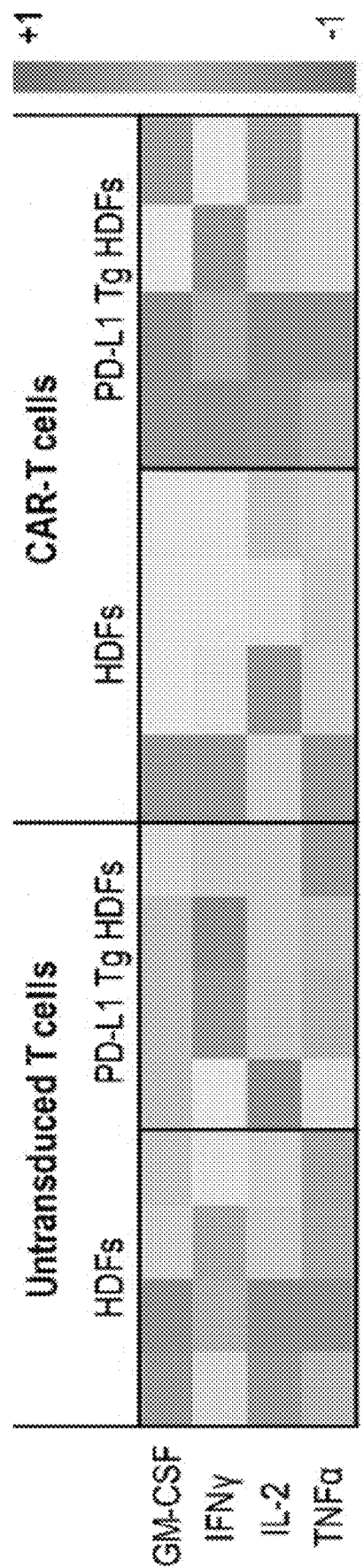
Figure 3E:
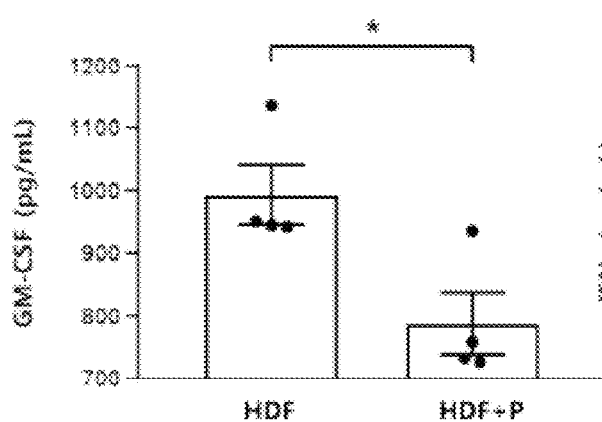
Figure 3F:
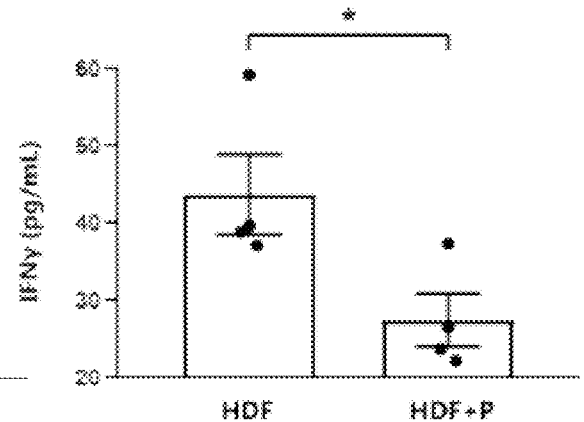
Figure 3G:
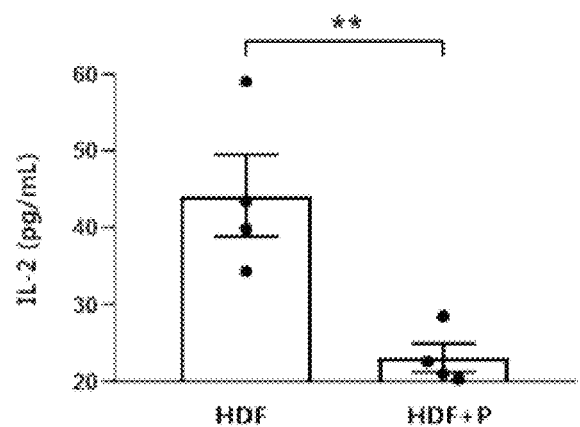
Figure 3H:
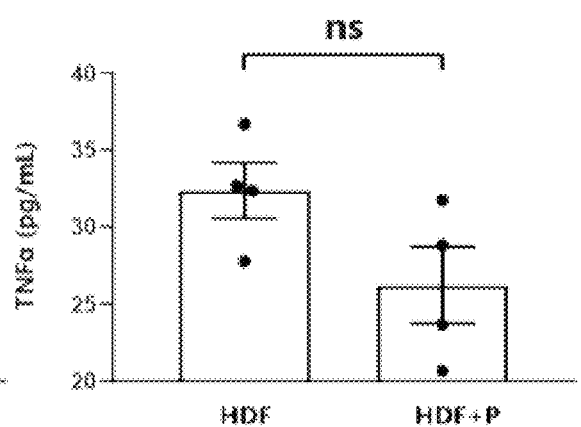

To test whether PD-L1 transgenic (Tg) HDFs provide protection against T cell-mediated cytotoxicity, the cells were challenged in an in vitro assay with human T cells harboring a chimeric antigen receptor (CAR) targeted against epidermal growth factor receptor (EGFR). EGFR targeting CAR-T cells are described in O'Rourke, D. M., et al., Sci. Transl. Med. (2007) 9, eaaa0984, herein incorporated by this reference. FIG. 3A shows a schematic of an anti-EGFR CAR T cell expressing PD-1 interacting with an HDF expressing EGFR and PD-L1. Ten thousand unmodified or PD-L1 Tg HDF target cells were plated in 96-well plates for 24-hours. Anti-EGFR CAR-T cells were then added to the wells at the indicated target-effector ratio. Cell viability was assayed at days 1, 2, and 4 using the CellTiterGlo assay (Promega). Both HDFs and human hepatocytes show positive EGFR expression (FIG. 3B) and can thus be targeted by the CAR-T cells. The challenge assay demonstrated that PD-L1 Tg HDFs consistently displayed improved protection against CAR-T mediated cytotoxicity than wild-type (WT) HDFs (FIG. 3C). HDF culture supernatants were collected and assayed for pro-inflammatory cytokines. A heatmap showing expression levels is shown in FIG. 3D. Production of pro-inflammatory cytokines, specifically that of granulocyte-macrophage colony-stimulating factor (GM-CSF, FIG. 3E), interferon gamma (IFN-γ, FIG. 3F), interleukin-2 (IL-2, FIG. 3G) and tumor necrosis factor alpha (TNFα, FIG. 3H), was reduced in the PD-L1 Tg HDF conditioned supernatant, when compared with WT HDF conditioned supernatant.

Protector Endothelial Cells Inhibited T Cell Activity

Figure 4A:
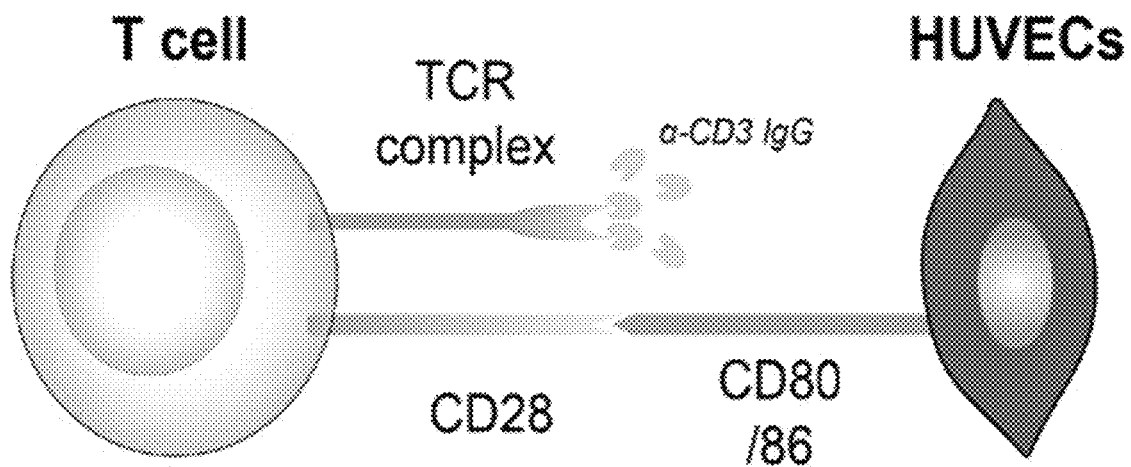
FIGS. 4A-4C show that PD-L1 upregulation on HUVECs provides protection against T cell mediated cytotoxicity.
Figure 4B:
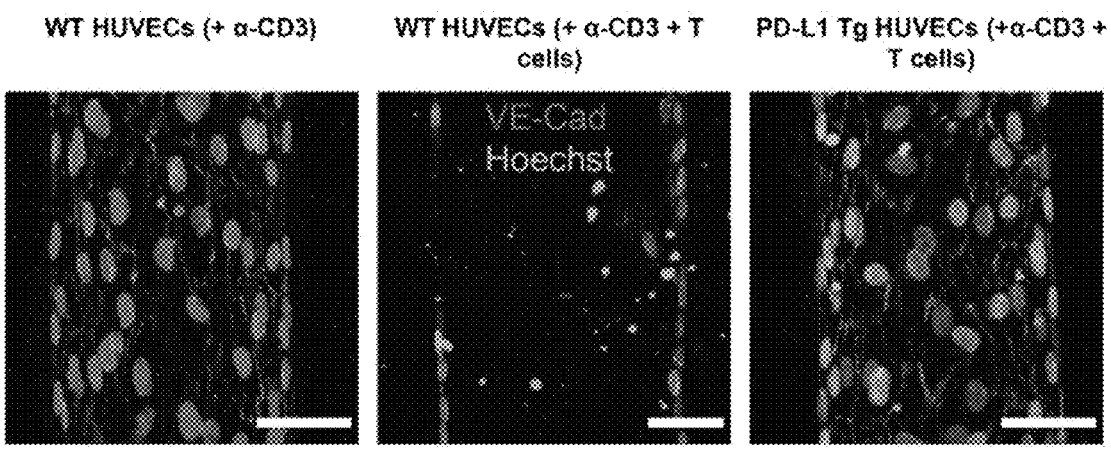

PD-L1 upregulation was then tested to determine whether it could provide a similar protective benefit for HUVECs. FIG. 4A shows a schematic of a T cell expressing TCR complex interacting with anti-CD3 antibodies, and CD28 interacting with a HUVEC expressing CD80/CD86. As described in the methods section, microfluidic blood vessels were fabricated and seeded with WT HUVECs and PD-L1 Tg HUVECs. These vessels were challenged for 24 hours with untransduced human T cells that were activated using an anti-CD3 IgG (clone OKT3) (Kurrle et al., T Cell Activation by CD3 Antibodies BT—Leukocyte Typing II, 137-146 Reinherz, E. L., Haynes, B. F., Nadler, L. M., Bernstein, I. D. (Eds.) (Springer, NY) (1986)) at a concentration of 30 ng/mL. The challenge assay demonstrated that PD-L1 Tg HUVECs are protected against T cell-mediated cytotoxicity, when compared with WT controls. The PD-L1 condition displays intact vessels whereas the barrier is disintegrated in the WT control condition (FIG. 4B).

Figure 4C:
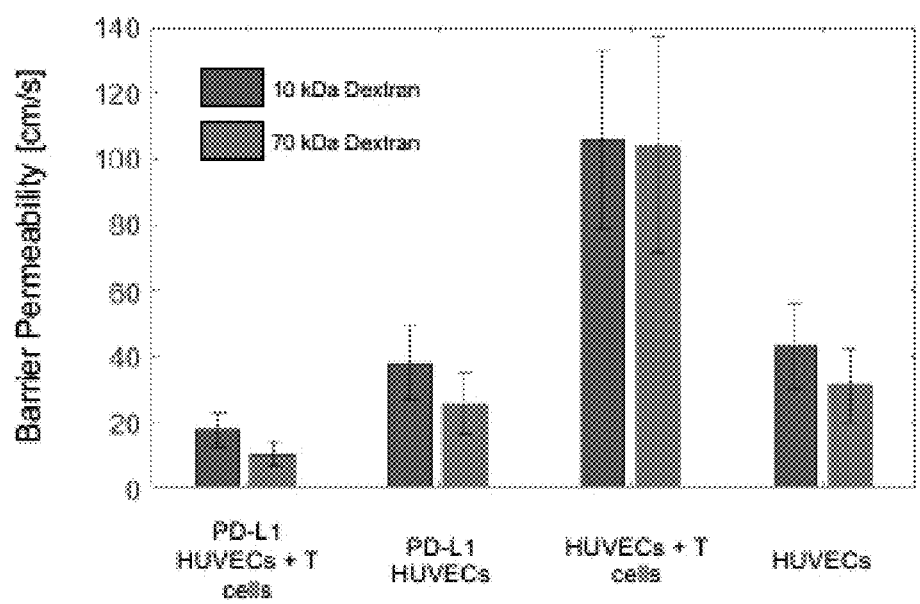

Further, the vascular permeability of the vessels was measured. Specifically, a perfusion medium containing 12.5 μg/mL of fluorescently labeled dextran (10 kDa Texas Red or 79 kDa Texas red to measure diffusion of different size molecules) was introduced into the vessel and diffusion of dextran into the surrounding hydrogel was measured in real time using an inverted spinning-disk microscope and time lapse photography. The resulting diffusion profile was fitted to a dynamic mass-conservation equation to determine diffusive permeability. PD-L1 Tg HUVECs seeded vessels demonstrate better barrier functionality compared to WT HUVECS seeded vessels. FIG. 4C. After challenge with untransduced human T cells+activated anti-CD3 IgG, the integrity of the WT HUVECs was reduced as demonstrated by increased permeability, wherein PD-L1 HUVEC seeded vessels were able to maintain barrier functionality.

Protector Stromal Cells Cloaked Hepatocytes from T Cell Cytotoxicity

Figure 5A:
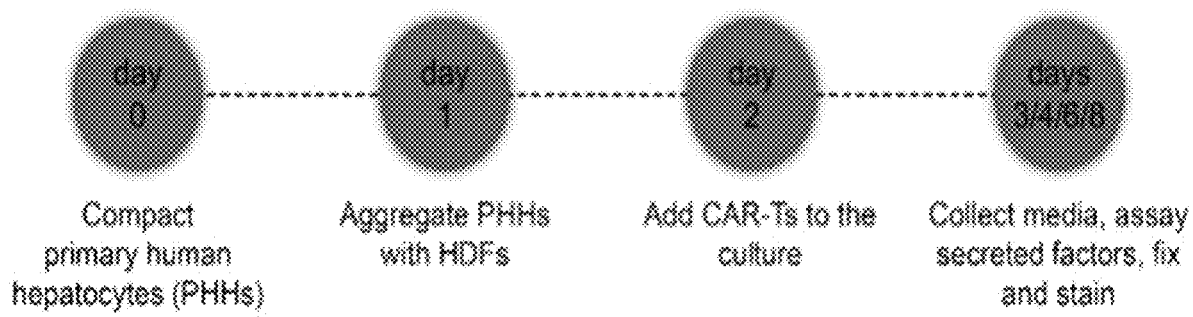
FIGS. 5A-5D show that PD-L1 upregulation on HDFs provides protection for human hepatocytes in a trans-configuration against CAR-T mediated cytotoxicity.
Figure 5B:
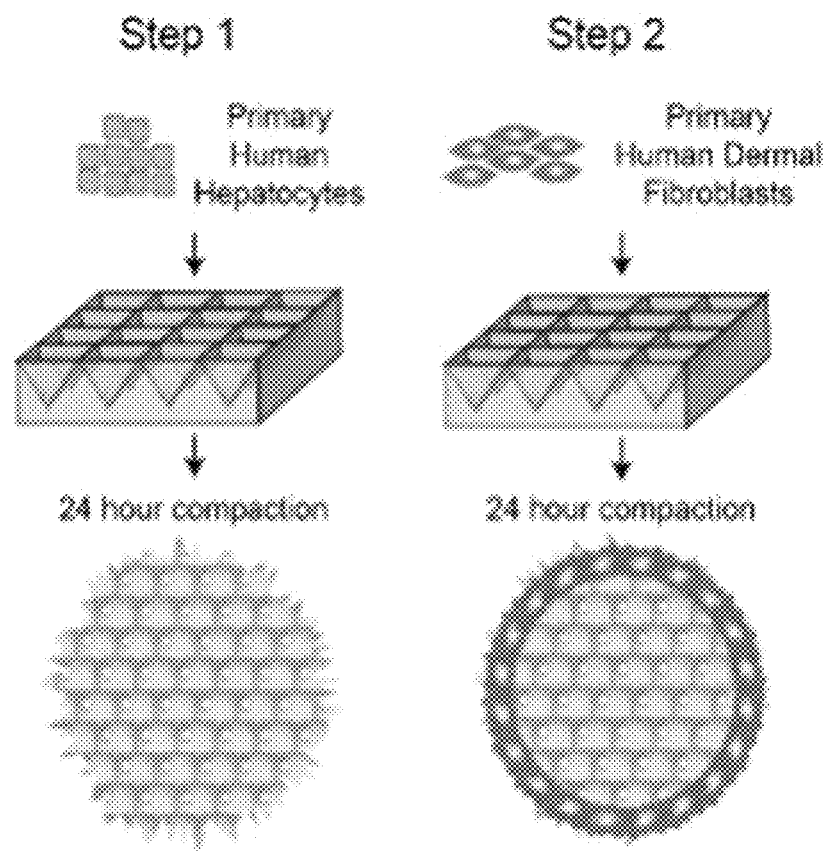
Figure 5C:
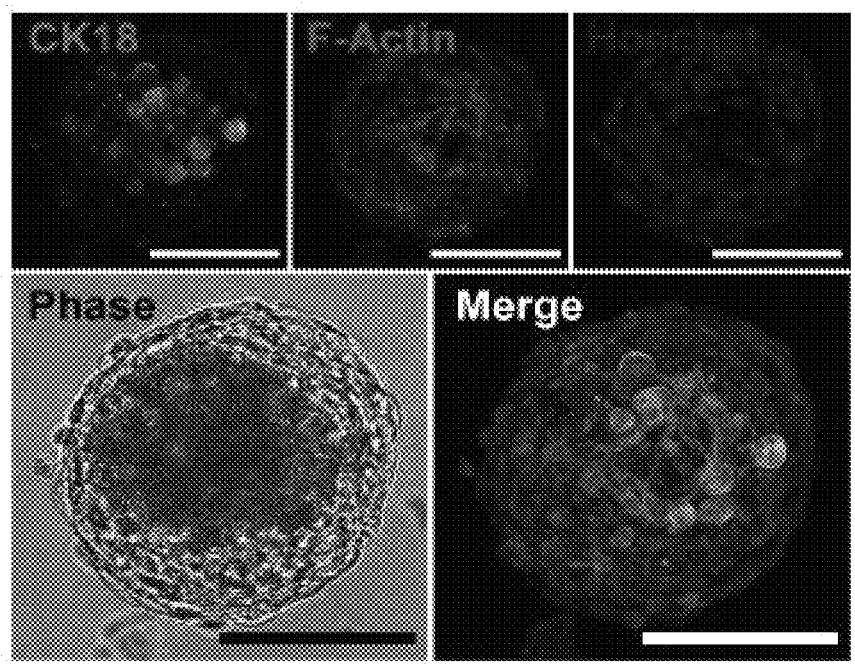

The ability of PD-L1 upregulation to protect unmodified cells was then tested. Specifically, unmodified PHHs were admixed with the genetically modified PD-L1 Tg HDFs to create a barrier around the PHHs using a two-step process (fabrication procedure described in detail in the methods section). FIG. 5A shows a schematic of the experimental timeline, and FIG. 5B shows a schematic of the two-step process. As expected, immunofluorescence indicated that PHHs stay in the core and HDFs form a surrounding barrier (FIG. 5C).

Figure 5D:
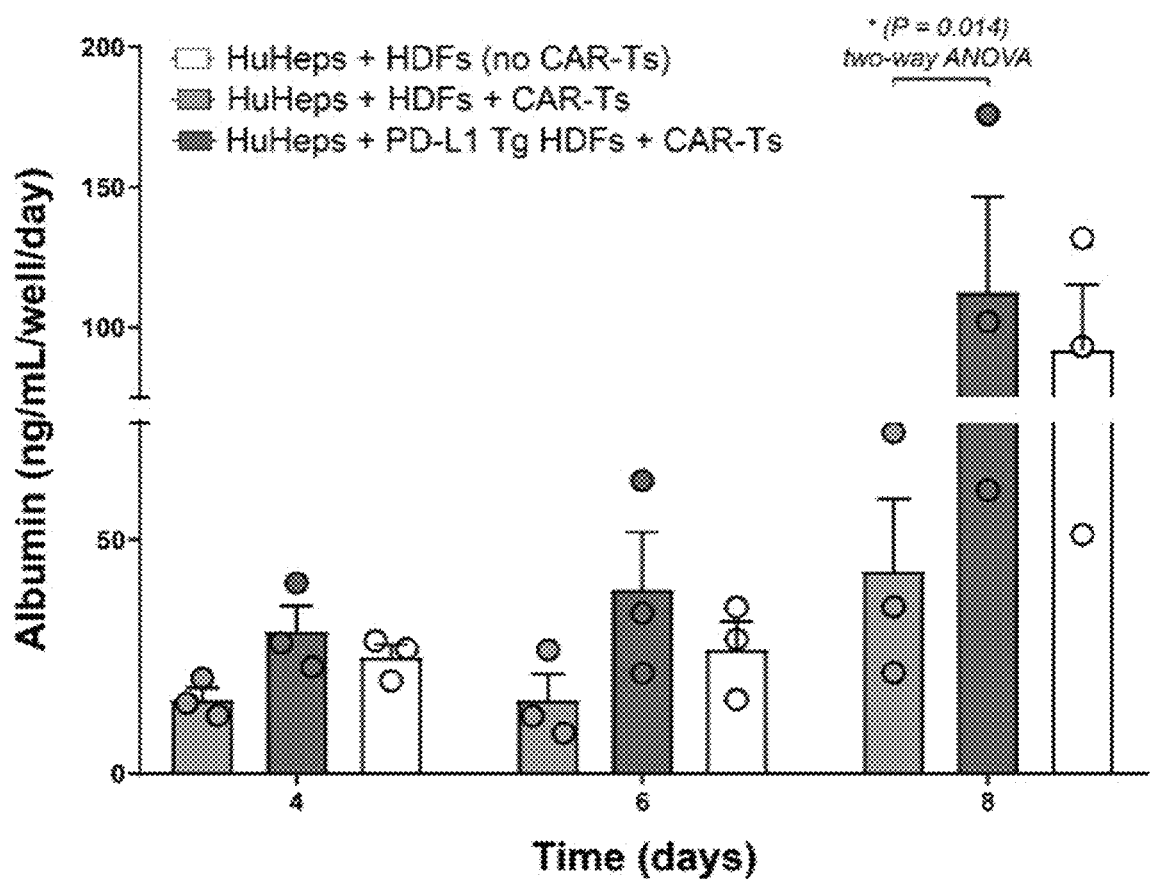

To determine whether this layer of PD-L1 Tg HDFs provide a barrier from infiltrating T cells, the constructs were challenged by adding EGFR CAR-Ts to the culture. As shown in FIG. 3B, both PHHs and HDFs express EGFR on their surface, thus rendering them susceptible to EGFR CAR-T mediated cytotoxicity. After several days in culture, albumin secretion from PHHs began to drop in culture conditions with WT HDFs (FIG. 5D). On the other hand, albumin secretion from culture conditions with PD-L1 Tg HDFs was maintained at levels similar to that from control conditions without any CAR-T cells (FIG. 5D), suggesting that genetic modifications on HDFs can protect PHHs in a trans-configuration.

Protector Stromal Cells were Inducibly Activated

To improve clinical translation of this protective platform, a control switch to PD-L1 expression in HDFs was added using a tetracycline-inducible construct. (GenTarget, San Diego, CA). Forty thousand HDFs/well were plated on 24-well plates for 24 hours. Inducible lentivirus was then added at an MOI of 10 with 8 μg/mL polybrene. The transduction media was replaced with culture media after 48 hours. After a 24-hour rest, the cells were put through 4 rounds of puromycin (2 μg/mL). PD-L1 expression was measure via flow cytometry.

Upon transduction of tetracycline repressor proteins (TetR), PD-L1 expression is repressed. However, exogenous administration of tetracycline (tet) can inhibit binding of TetR to the Tet operator region, thus activating expression. FIG. 6A shows a schematic of the inducible expression of PD-L1. FIG. 6B shows the flow cytometry analysis of PD-L1 expression on the surface of HDFs at various concentrations of tet. This system allows the user to control PD-L1 expression on HDFs with fast kinetics. Furthermore, doxycycline (an analog of tetracycline) is already approved for clinical use.

Discussion

In this study, a novel, controllable, persistent source of immune-tolerance for a wide number of cell-based therapies was demonstrated. Genetically modified stromal cells such as HDFs, which upregulate immune inhibitory factors, inhibited cytotoxicity of targeted T cells towards the HDFs. In addition, these genetically modified cells were able to provide protection for unmodified PHHs. This trans-based bystander protection is valuable as it allows one to store modified cells and utilize them 'off-the-shelf' in order to impart tolerance to any number of cell-based therapies. Parenchymal cells are limited in number and genetic modifications tend to be inefficient. Utilizing banked genetically modified cells and admixing them with the unmodified, parenchymal cells provides a solution to this problem.

For patients who need a transplant but are unable to receive one, the limiting factor is availability of tissue. Cell-based therapies offer an alternative, but their persistence in vivo is hampered by chronic immune rejection. The vast majority of current technologies that provide local immunosuppression to cell-based therapies are based on either a) engineering biomaterials to present inhibitory signals, or b) genetic manipulation of the cells that need protection. While tethering immunosuppressive signals to biomaterials can be localized and effective, it often does not persist for long periods. Biomaterials tend to remodel and degrade in vivo. Cells, on the other hand, can serve as perennial synthetic factories for production and presentation of immunosuppressive signals.

In summary, the utilization of cells engineered to express immunomodulatory proteins provides a controllable, persistent source of immunotolerance in a trans-format for implantable grafts.

Approved cell therapies such as Kymriah are currently listed at ~$500,000. While the clinical benefits offered by a one-time cell-based therapy can be enormous, a large portion of the inordinately high price of such therapies arises from the manufacturing challenges that accompany them. CAR-T cells, for example, need bespoke manufacturing for each patient and thus cannot benefit from economies of scale. By enabling universal compatibility for a wide variety of cell-based therapies, the compositions and methods of the disclosure can provide therapeutic solutions that would exponentially reduce manufacturing challenges.

Example 2—Analysis of Hepatic Organoids Containing Support Cells Expressing PD-L1

In this example, a normal tissue microenvironment was engineered to function in a trans-protective mode by controlled activation of immune checkpoint inhibitory pathways in genetically engineered supporting stromal cells and/or in endothelial cells lining the vasculature to induce immune cell exhaustion and anergy when admixed with parenchymal cells that need protection.

As a prototype, human dermal fibroblasts (HDFs), cells that have been shown to improve the function of hepatocytes in vitro and in vivo (Keir et al., J. Exp. Med. (2006) 203:883-895; Stevens et al., Sci. Transl. Med. (2017) 9:399), were engineered to overexpress PD-L1 on their surface and co-encapsulated with primary human hepatocytes (PHHs), as described in Example 1. The co-encapsulated cells were placed into a fibrin hydrogel to create a functional liver graft.

Figure 7C:
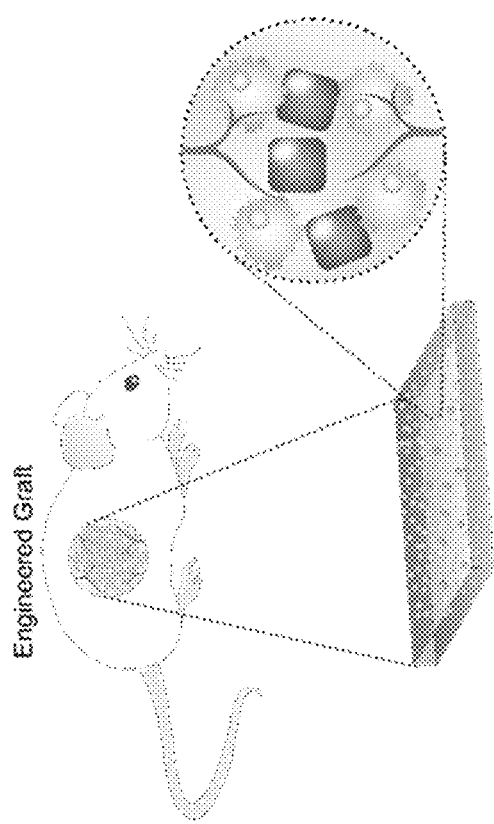
FIGS. 7A-7D show a schematic of universal transplantation strategy.
Figure 7D:
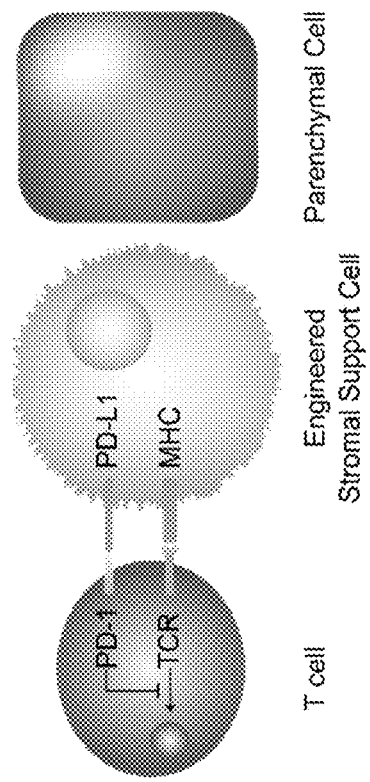
Figure 7A:
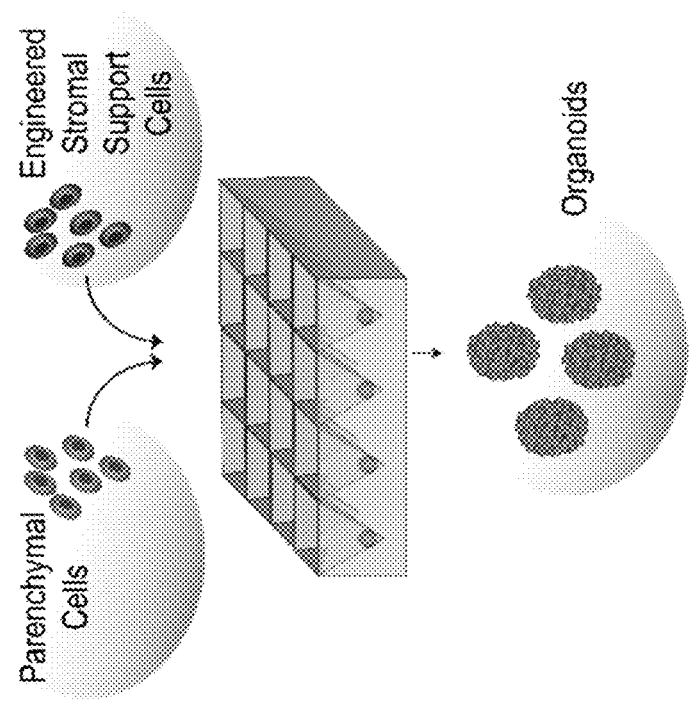

Hepatic organoids were synthesized via a versatile aggregation process that utilized an array of pyramid-shaped microwells (FIG. 7A). Six-well polystyrene plates containing pyramidal inserts were passivated using 5% Pluronic (Sigma Aldrich) for 30 mins. Each well was then rinsed three times with 2 mL DMEM containing 1% (v/v) penicillin-streptomycin per well.

Figure 7B:
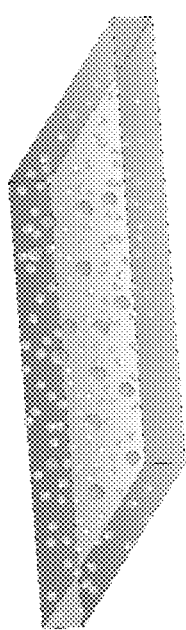
Figure 8A:
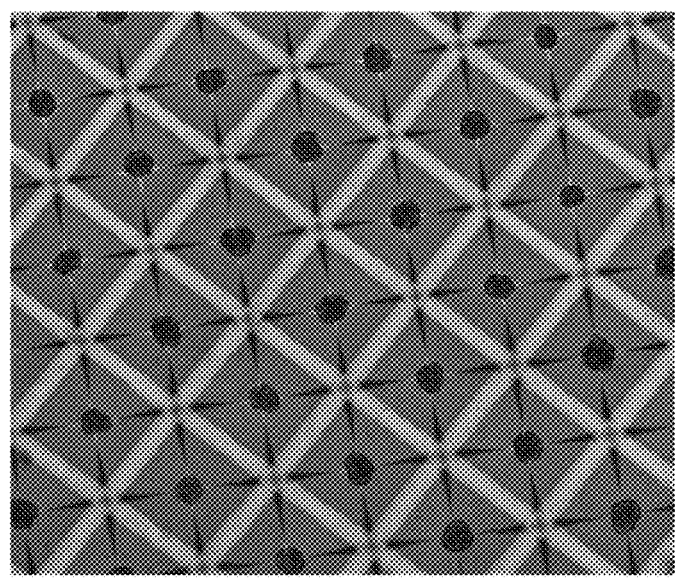
FIGS. 8A-8B depict the fabrication and characterization of hepatic organoids.
Figure 8B:
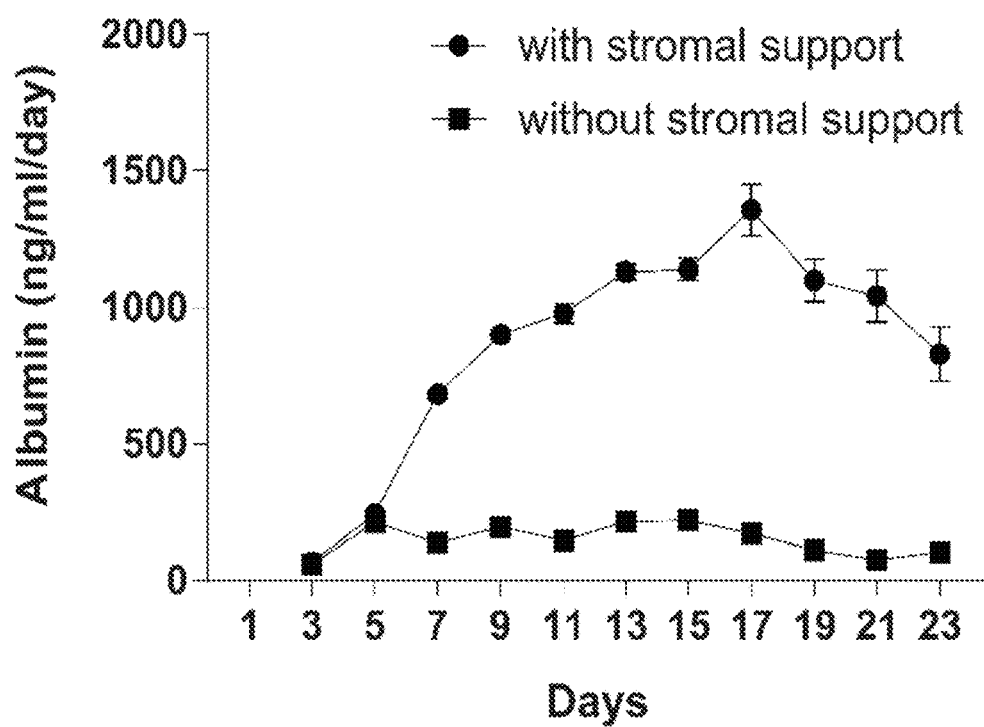

Cryopreserved unmodified PHHs were thawed, spun down at 60×g for 6 mins in DMEM and resuspended in ITS media (DMEM with L-glutamine supplemented with 1% (v/v) ITS Universal Culture Supplement (Corning Life Sciences), 1% (v/v) penicillin/streptomycin, 10% (v/v) fetal bovine serum, 15.4 mM HEPES (Thermo Fisher Scientific), 70 ng/mL glucagon (Sigma Aldrich), and 40 ng/ml dexamethasone (Sigma Aldrich)). Growth-arrested fibroblasts were washed several times with DMEM containing 1% (v/v) penicillin-streptomycin and then dissociated using 0.25% Trypsin (Thermo Fisher). Fibroblasts were spun down at 1000 rpm for 5 minutes and resuspended in ITS media. The two cell populations were added to each well of the polystyrene plate containing pyramidal inserts in the following proportions: 0.6M PHHs and 0.6M fibroblasts in 2 mL of ITS media. The plate was then spun at 60×g for 6 mins and incubated at 37° C., 5% CO2 for two days to allow the cells to aggregate. Over that period of two days, the support cells synthesize extracellular matrix and the two cell populations compact to form an organoid. FIG. 7B shows the resulting liver graft of organoids placed in the fibrin hydrogel, and FIG. 7C is a schematic showing placement of the liver graft into a mouse. FIG. 7D shows the interaction of an engineered stromal support cell in the liver graft with endogenous T cells to protect the parenchymal cells (e.g., hepatocytes) in the graft. FIG. 8A is an image of the organoids formed in the pyramid-shaped microwells. Cell culture supernatants were collected and albumin secretion was measured using a human albumin specific ELISA quantitation kit (Bethyl Laboratories). As shown in FIG. 8B, albumin secretion of PHHs is increased in the presence of unmodified stromal support cells. These results indicate the organoids help stabilize the phenotype of the hepatocytes and are amenable to a variety of downstream configurations.

Figures 9A, 9B:
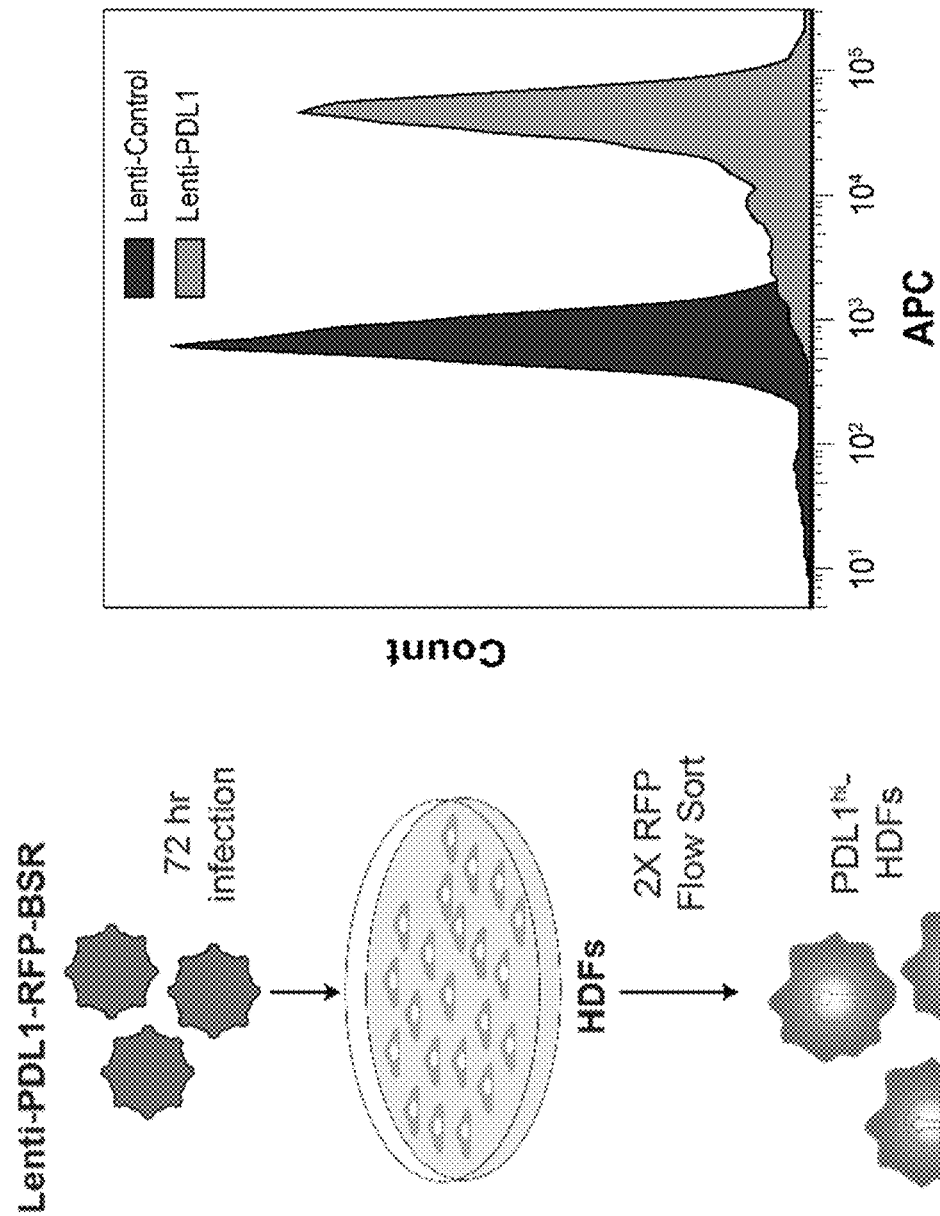
FIGS. 9A-9B depict the genetic engineering of stromal support cells.
Figure 10:
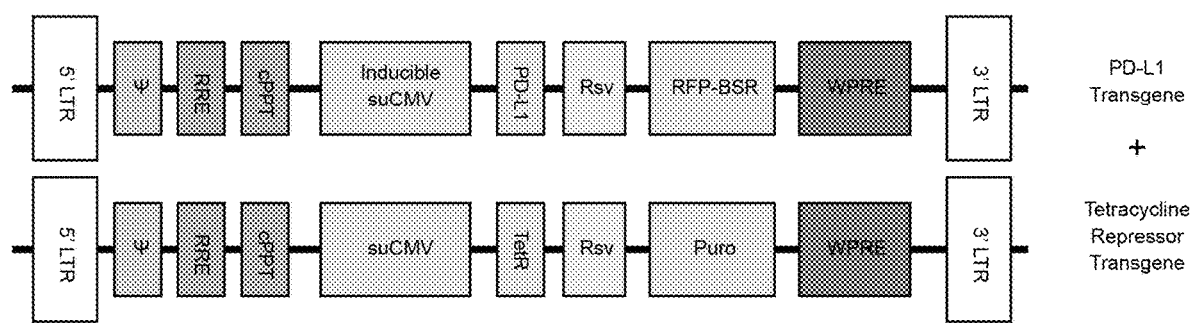
FIG. 10 is a schematic of vectors expressing the PD-L1 transgene under an inducible suCMV promoter and a tetracycline (Tet) repressor transgene under an suCMV promoter to turn the overexpression of PD-L1 on or off.
Figure 11:
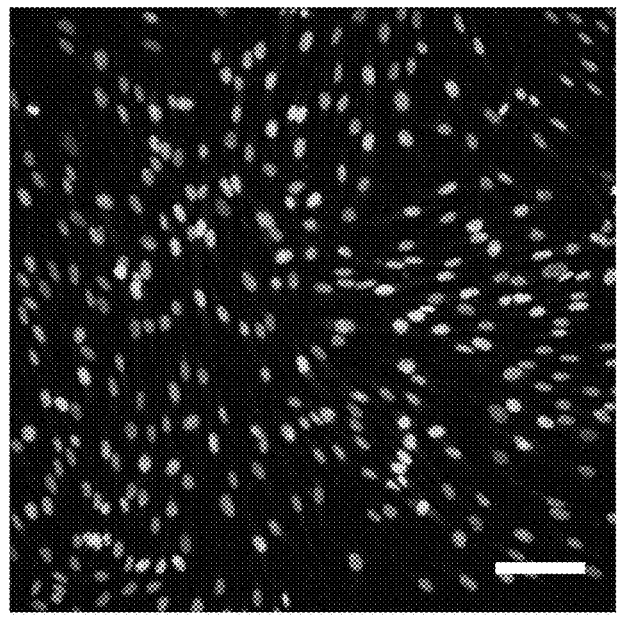
FIG. 11 is an immunofluorescence analysis demonstrating expression of PD-L1 in control and lentiviral transfected cells.
Figure 11:
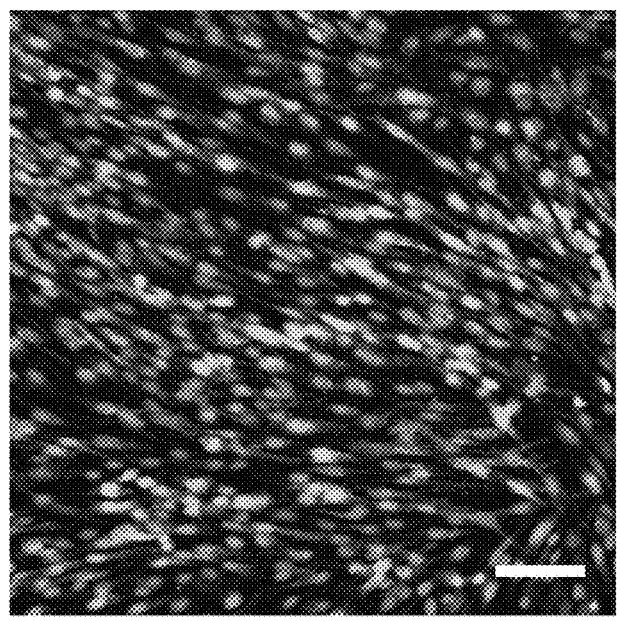

To generate a population of HDFs genetically engineered to overexpress PD-L1, lentiviral vectors with the PD-L1 sequence under an inducible super cytomegalovirus (suCMV) promoter (GenTarget) were utilized to transgenically overexpress the surface protein in HDFs (FIG. 9A). The transduced HDFs were selected using flow cytometry for red fluorescent protein and expanded to isolate a pure population of PD-L1$^{hi}$ HDFs (FIG. 9B). Since PD-L1 was expressed under an inducible version of suCMV promoter, the cells were transduced with a tetracycline repressor vector to create a controllable cell line, whose overexpression of PD-L1 was turned on or off when needed (FIG. 10). FIG. 11 is an immunofluorescence analysis demonstrating expression of PD-L1 in control and lentiviral transfected cells.

Next, implantable grafts were fabricated by embedding the hepatic organoids in a natural biomaterial, specifically fibrin.

Figure 12A:
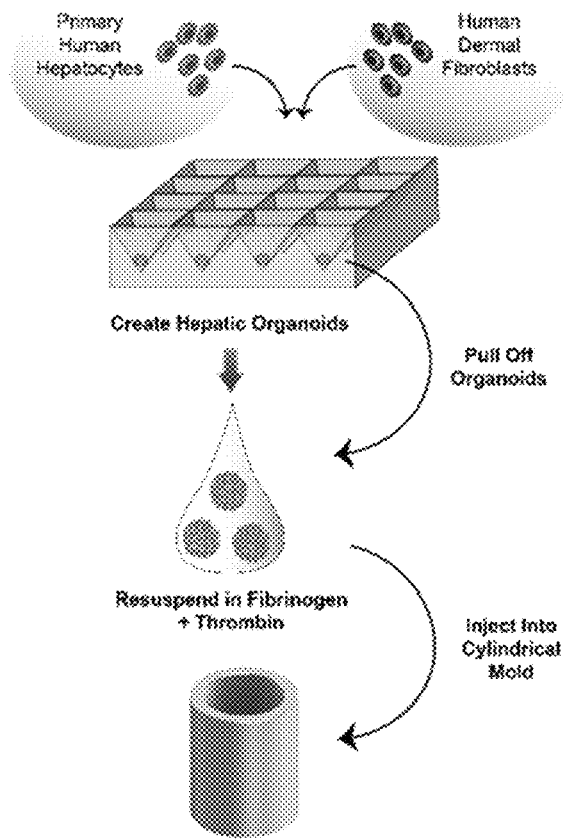
FIGS. 12A-12B depict the fabrication of engineered liver grafts.
Figure 12B:
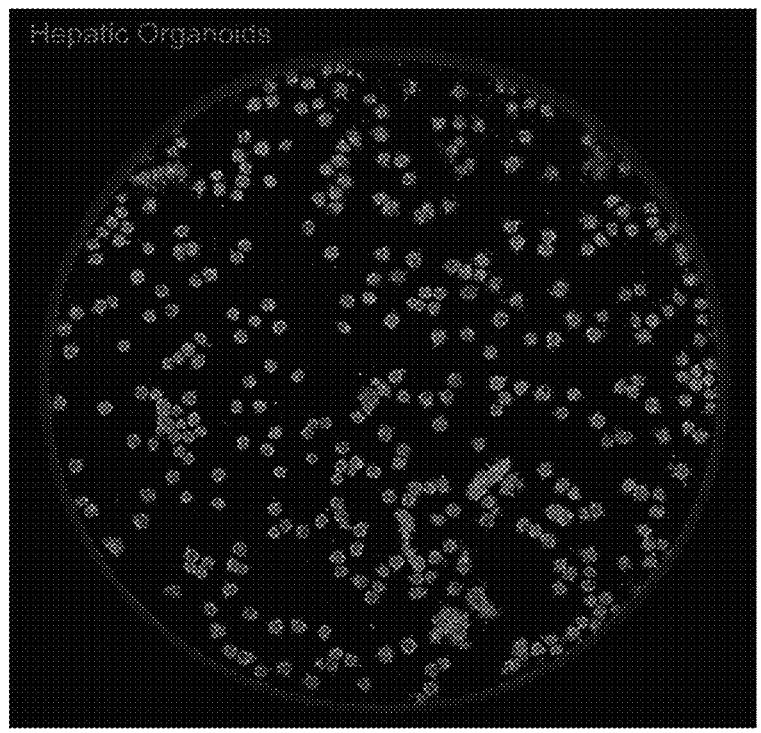

The organoids with PHHs and PD-L1$^{hi}$ HDFs were removed from the microwells and suspended in a solution of 2.5 mg/ml bovine fibrinogen (Sigma Aldrich), 1 U/ml bovine thrombin (Sigma Aldrich), and DPBS added into the mold and was allowed to crosslink at room temperature for 10 minutes before media addition. This solution was deposited in a cylindrical mold (FIG. 12A). After the solution polymerized to form fibrin, the implantable grafts were cut out of the mold using a 1-mm biopsy punch. Each punched out unit represents a liver graft that can be implanted ectopically in an animal and can maintain a host of human liver functions in vivo (FIG. 12B).

A population of stromal support cells that overexpress immunomodulatory proteins such as PD-L1 in an inducible format were engineered. When aggregated and cultured in microwells, these engineered support cells improved the function of parenchymal cells and compacted to form organoids. The organoids can be encapsulated in biomaterials to create implantable grafts that provide inhibitory signals to T cells in vivo. This platform enables localized, controllable immunotolerance in a transplantation setting. It is envisioned this approach will supplement existing implantable allogeneic therapies and provide a universally compatible solution for patients who do not have access to an HLA-matched organ.

Because a versatile and modular platform that can be easily translated for imparting localized immunotolerance to a variety of parenchymal cells was designed, the application of this technology can be expanded to allogeneic transplants for a number of different organs (kidney, pancreas, heart and lung).

Example 3—In Vitro and In Vivo Studies to Characterize Immunosuppression

Cells expressing a multiplex of the rationally selected inhibitory factors are generated by transfecting cells with one or more nucleic acids expressing each factor, for example, PD-L1, CD47, CD39 and CD73. Both stromal and endothelial cell lines harboring one, two, three or all of the modifications simultaneously are challenged in vitro (FIG. 13) or in vivo (FIG. 14) to evaluate the additive benefit of each molecule. Implantable grafts are then created with protector cells harboring the minimum number of modifications necessary to provide adequate immune protection.

Figure 13:
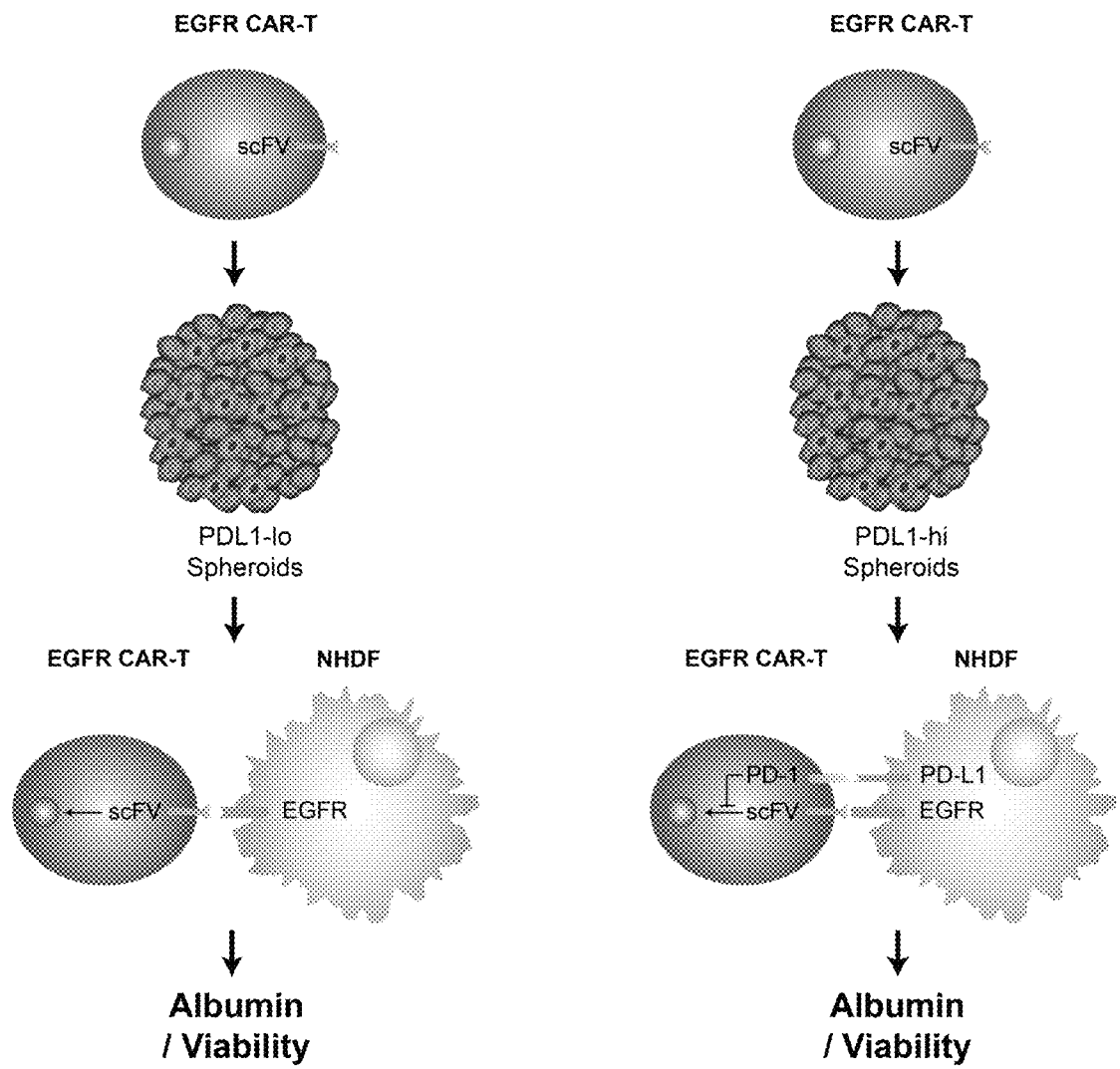
FIG. 13 is a schematic of an in vitro assay to characterize immunosuppression.

In an vitro study, implantable grafts that are either unmodified or modified with selected inhibitory facts are challenged with EGFR CAR-T cells. FIG. 13. The viability and functionality, e.g., albumin secretion, of the implantable grafts are measured at different time points after challenge.

Figure 14:
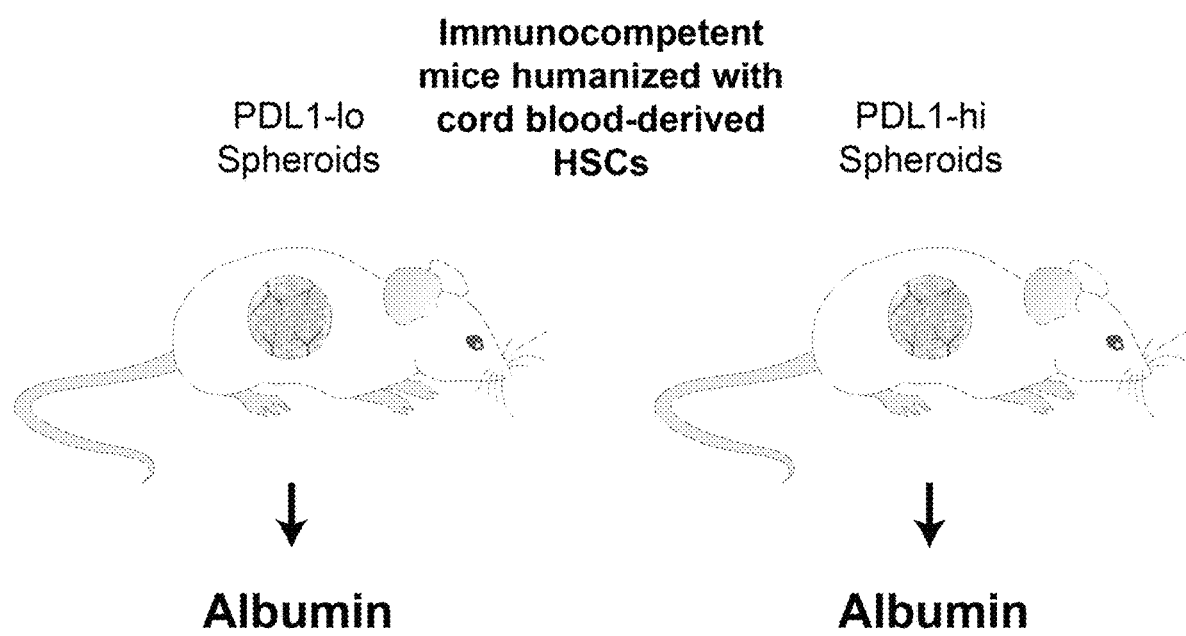
FIG. 14 is a schematic of in vivo characterization of immunosuppression.
Figure 15:
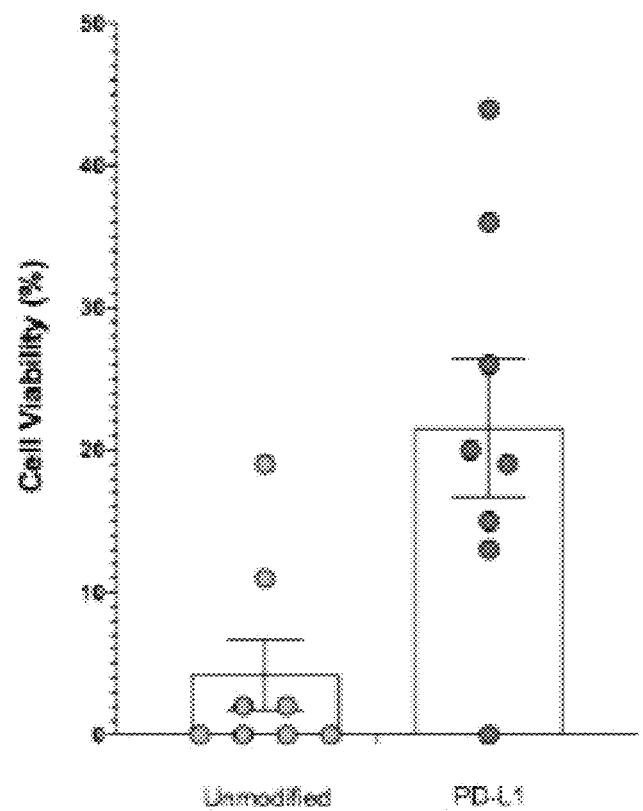
FIG. 15 is a graph depicting cell viability of unmodified and PD-L1 modified HDFs 2 weeks after subcutaneous implantation into immunocompetent C57BL/6 mice. Each circle represents a mice that was implanted with one graft.

In an in vivo study, implantable grafts of HDFs engineered to express PD-L1 as described in the above Examples were implanted into immunocompetent animals, specifically C57BL/6 mice, such that they were challenged by the full repertoire of the animal's immune system (FIG. 14). As a positive control, conditions with administration of systemic immunosuppression (Cyclosporine A) were included. Prior to implantation, the grafts were tagged with firefly luciferase under a CMV promoter. The viability of PD-L1 modified, and unmodified implantable grafts were measured two weeks post-implantation. FIG. 15. D-luciferin (30 mg/mL) was injected directly into the subcutaneous region near the graft and the emitted light was measured using an IVIS bioluminescent imaging system. The data show that PD-L1 modified grafts retained higher cell viability, whereas viability was decreased in unmodified grafts.

These experiments are useful to gauge long-term viability of the implanted grafts in the presence of minimal immunosuppression. Additional studies can be carried out in non-human primate models.

INCORPORATION BY REFERENCE

All documents and references, including patent documents and websites, described herein are individually incorporated by reference to into this document to the same extent as if there were written in this document in full or in part.

EQUIVALENTS

Those skilled in the art will recognize or be able to ascertain, using no more than routine experimentation, many equivalents of the specific embodiments described herein. Such equivalents are intended to be encompassed by the following claims.

The invention claimed is:

1. A composition suitable for implantation into a subject comprising:
   (a) a first cell population comprising parenchymal cells, endothelial cells, or a combination thereof, wherein the first cell population is allogenic to the subject and is not genetically engineered; and
   (b) a second cell population comprising stromal cells genetically engineered to express at least one immune checkpoint protein, which inhibit an immune response to the first cell population following implantation of the composition into the subject, wherein the at least one immune checkpoint protein is PD-L1, and wherein the stromal cells are not genetically engineered to express CTLA4.

2. The composition of claim 1, wherein the genetically engineered cells of the second cell population comprise a vector which expresses the protein.

3. The composition of claim 2, wherein the vector is a viral vector.

4. The composition of claim 2, wherein the second population of cells further comprises a repressor or activator component.

5. The composition of claim 4, wherein the repressor component is a tetracycline or lac repressor.

6. The composition of claim 4, wherein the repressor or activator component is co-transfected into the second population of cells.

7. The composition of claim 1, wherein expression of the protein is under the control of a constitutively active promoter, an inducible promoter, a tissue specific promoter, a cell-type specific promoter or a temporally restricted promoter.

8. The composition of claim 1, wherein the first cell population and the second cell population are in a suspension or an aggregate.

9. The composition of claim 8, wherein the aggregate is encapsulated in an extracellular matrix.

10. The composition of claim 1, wherein
    (a) the first cell population comprises primary hepatocytes or vascular endothelial cells, and
    (b) the stromal cells in the second cell population are genetically engineered dermal fibroblasts (HDFs) and the at least one immune checkpoint protein is controlled by an inducible promoter, wherein the genetically engineered HDFs inhibit an immune response to the first cell population.

11. The composition of claim 1, wherein the first cell population and second cell population each consist essentially of human cells.

12. The composition of claim 1, wherein the stromal cells in the second cell population are genetically engineered to express only one immune checkpoint protein that is PD-L1.

13. A method of making the composition of claim 1, the method comprising, mixing the first cell population and the second cell population in cell culture medium under conditions sufficient to maintain viability of the cells.

14. An implantable graft for implantation into a subject comprising:
    (a) a first cell population comprising parenchymal cells, endothelial cells, or a combination thereof, wherein the first cell population is allogenic to the subject and is not genetically engineered;

(b) a second cell population comprising stromal cells genetically engineered to express at least one immune checkpoint protein, which inhibit an immune response to the first cell population following implantation of the composition into the subject, wherein the at least one immune checkpoint protein is PD-L1, and wherein the stromal cells are not genetically engineered to express CTLA4, wherein the first and second cell populations are encapsulated in an extracellular matrix.

15. A method of making the implantable graft of claim 14, the method comprising, (i) mixing the first cell population and the second cell population in cell culture medium under conditions to maintain viability of the cells, thereby yielding a cell mixture, (ii) co-culturing the cell mixture until extracellular matrix synthesized by the stromal cells encapsulates the cell mixture to form cell aggregates, and (iv) suspending the aggregates in a solution comprising fibrinogen and thrombin under conditions which promote formation of fibrin for a time sufficient to form the implantable graft.

16. A method of inhibiting immune rejection, reducing immune activation, or promoting immune tolerance of a graft in a subject, the method comprising implanting the graft of claim 14 into the subject.

17. The method of claim 16, wherein the second cell population comprises allogeneic cells or xenogeneic cells to the subject.

18. The method of claim 16, wherein the subject has an autoimmune condition.

19. The method of claim 16, wherein the method inhibits fibrosis in the subject.

20. The method of claim 16, wherein the graft is implanted at an orthotopic site.

21. The method of claim 16, wherein the graft is implanted at an ectopic site.

* * * * *